United States Patent
Rivella et al.

(10) Patent No.: US 12,241,079 B2
(45) Date of Patent: Mar. 4, 2025

(54) COMPOSITIONS AND METHODS FOR HEMOGLOBIN PRODUCTION

(71) Applicant: THE CHILDREN'S HOSPITAL OF PHILADELPHIA, Philadelphia, PA (US)

(72) Inventors: Stefano Rivella, Philadelphia, PA (US); Maxwell Chappell, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 952 days.

(21) Appl. No.: 17/272,783

(22) PCT Filed: Sep. 16, 2019

(86) PCT No.: PCT/US2019/051258
§ 371 (c)(1),
(2) Date: Mar. 2, 2021

(87) PCT Pub. No.: WO2020/056400
PCT Pub. Date: Mar. 19, 2020

(65) Prior Publication Data
US 2021/0222200 A1   Jul. 22, 2021

Related U.S. Application Data

(60) Provisional application No. 62/731,508, filed on Sep. 14, 2018.

(51) Int. Cl.
*C12N 15/86*   (2006.01)
*A61P 7/06*   (2006.01)
*C07K 14/805*   (2006.01)

(52) U.S. Cl.
CPC .............. *C12N 15/86* (2013.01); *A61P 7/06* (2018.01); *C07K 14/805* (2013.01); *C12N 2740/15041* (2013.01); *C12N 2740/16043* (2013.01); *C12N 2830/40* (2013.01); *C12N 2830/48* (2013.01)

(58) Field of Classification Search
None
See application file for complete search history.

(56) References Cited

U.S. PATENT DOCUMENTS

| | | |
|---|---|---|
| 7,541,179 B2 | 6/2009 | Sadelain et al. |
| 7,901,671 B2 | 3/2011 | Leboulch et al. |
| 8,058,061 B2 | 11/2011 | Sadelain et al. |
| 9,068,199 B2 | 6/2015 | Leboulch et al. |
| 11,311,632 B2 | 4/2022 | Rivella et al. |
| 2003/0022303 A1* | 1/2003 | Sadelain ........... A61P 7/06 435/235.1 |
| 2009/0124566 A1 | 5/2009 | Chi et al. |
| 2009/0156534 A1* | 6/2009 | Lisowski ........... A61P 7/06 435/320.1 |
| 2009/0274671 A1 | 11/2009 | Sadelain et al. |
| 2012/0009161 A1 | 1/2012 | Leboulch et al. |
| 2012/0039932 A1 | 2/2012 | Allen et al. |
| 2015/0224209 A1 | 8/2015 | Kohn et al. |
| 2017/0157270 A1 | 6/2017 | Kohn et al. |
| 2017/0173185 A1 | 6/2017 | Sadelain et al. |
| 2018/0008725 A1 | 1/2018 | Rivella et al. |
| 2018/0051059 A1 | 2/2018 | Blobel et al. |
| 2018/0363004 A1 | 12/2018 | Heffner et al. |
| 2022/0202958 A1 | 6/2022 | Rivella et al. |
| 2022/0389448 A1 | 12/2022 | Rivella et al. |

FOREIGN PATENT DOCUMENTS

| | | |
|---|---|---|
| WO | 2002/010454 A2 | 2/2002 |
| WO | 2003/002155 A1 | 1/2003 |
| WO | 2004/083383 A2 | 9/2004 |
| WO | 2011/011584 A1 | 1/2011 |
| WO | 2013/184197 A1 | 12/2013 |
| WO | 2014/043131 A1 | 3/2014 |
| WO | 2014/108812 A2 | 7/2014 |
| WO | 2016/118715 A1 | 7/2016 |
| WO | 2017/003792 A1 | 1/2017 |
| WO | 2017/079591 A2 | 5/2017 |
| WO | 2017/191274 A2 | 11/2017 |
| WO | 2019/213011 A1 | 11/2019 |

OTHER PUBLICATIONS

Oh et al., "Lentiviral vector design using alternative RNA export elements", Retrovirology, vol. 4, pp. 1-9, Published Jun. 5, 2007. (Year: 2007).*

Mauro et al., "A critical analysis of codon optimization in human therapeutics", Trends Mol Med, vol. 20, pp. 604-613, Published Nov. 2014. (Year: 2014).*

Han et al., "Fetal gene therapy of alpha-thalassemia in a mouse model", PNAS, vol. 104, pp. 9007-9011, Published May 22, 2007. (Year: 2007).*

Kannengiesser, et al., "Missense SLC25A38 variations play an important role in autosomal recessive Inherited sideroblastic anemia" Haematoloica (2011) 96(6):808-813.

Guernsey, et al., "Mutations in mitochondrial carrier family gene SLC25A38 cause nonsyndromic autosomal recessive congenital sideroblastic anemia" Nat. Genet. (2009) 41(6): 651-653.

Dufay, J.N., "Defining the role of Hem25 in mitochondrial function: implications for congenital sideroblastic anemia" Master of Science Thesis, Dalhousie University, Hailfax, Nova Scotia (2015) Retrieved from the internet: https://dalspace.library.dal.ca/handle/10222/58896.

(Continued)

*Primary Examiner* — Brian Whiteman
*Assistant Examiner* — Stephanie L Sullivan
(74) *Attorney, Agent, or Firm* — Robert C. Netter, Jr.; Dann, Dorfman, Herrell & Skillman

(57) ABSTRACT

Methods and compositions for producing hemoglobin and treating alpha-thalassemia are disclosed.

Figure 1A:
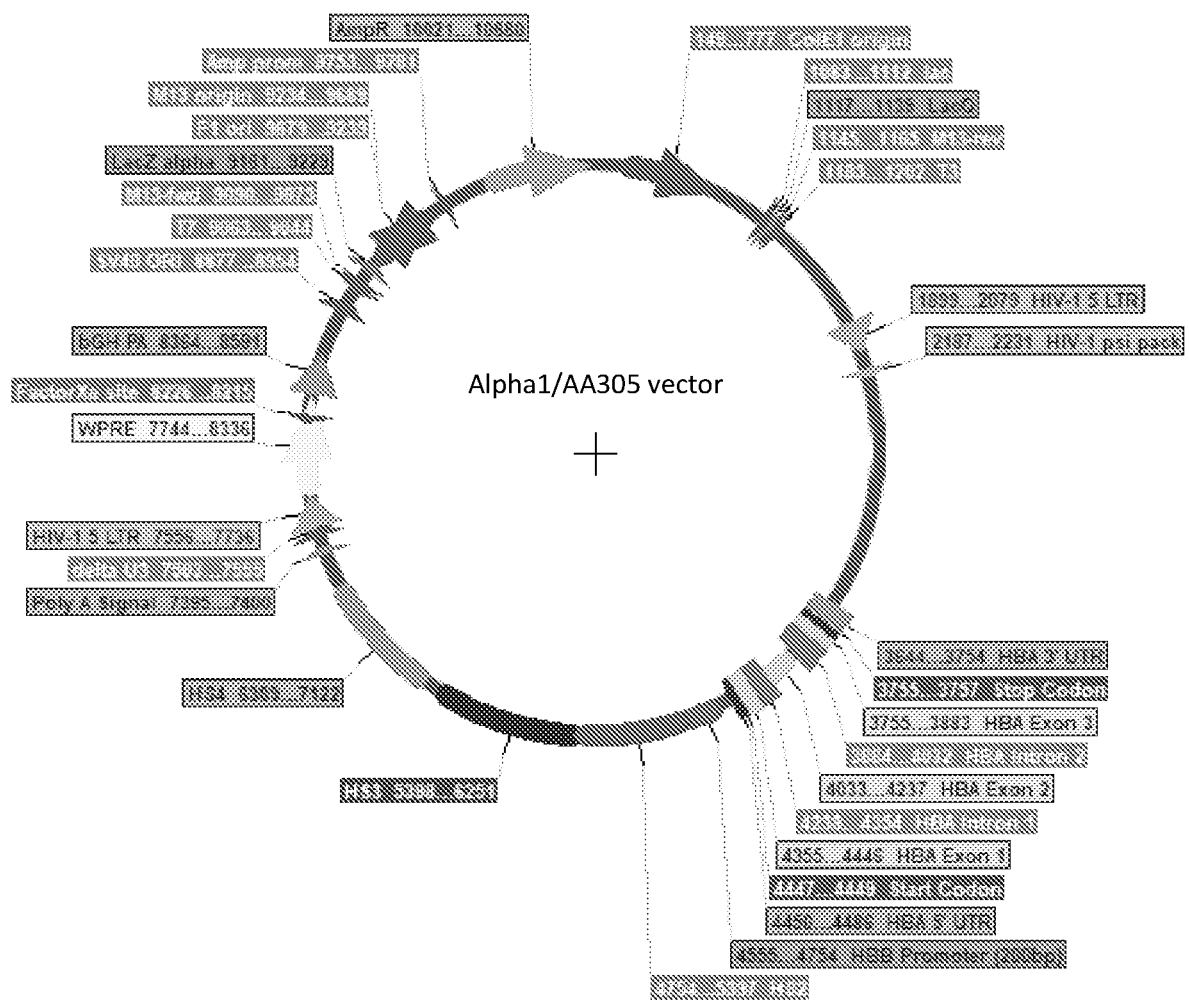

39 Claims, 47 Drawing Sheets
Specification includes a Sequence Listing.

(56) References Cited

OTHER PUBLICATIONS

Chiabrando, et al., "Heme and erythropoieis: more than a structural role" Haematologica (2014) 99(6):973-83.
Musallam, K.M., et al., "Non-transfusion-dependent thalassemias" Haematologica (2013) 98(6):833-44.
Rivella, S., "The role of ineffective erythropoiesis in non-transfusion-dependent thalassemia" Blood Rev. (2012) 26 Suppl 1:S12-5.
Ginzburg, Y., et al., "β-thalassemia: a model for elucidating the dynamic regulation of ineffective erythropoiesis and iron metabolism" Blood (2011) 118(16):4321-30.
May, C., et al., "Successful treatment of murine beta-thalassemia intermedia by transfer of the human beta-globin gene" Blood (2002) 99(6):1902-8.
May, C., et al., "Therapeutic haemoglobin synthesis in beta-thalassaemic mice expressing lentivirus-encoded human beta-globin" Nature (2000) 406(6791):82-6.
Rivella, S., et al., "A novel murine model of Cooley anemia and its rescue by lentiviral-mediated human beta-globin gene transfer" Blood (2003) 101(8):2932-9.
Breda, L., et al., "Therapeutic hemoglobin levels after gene transfer in B-thalassemia mice and in hematopoietic cells of B-thalassemia and sickle cells disease patients" PLoS One (2012) 7(3):e32345.
Pawliuk, R., et al., "Correction of sickle cell disease in transgenic mouse models by gene therapy" Science (2001) 294(5550):2368-71.
Cavazzana-Calvo, M., et al., "Transfusion independence and HMGA2 activation after gene therapy of human β-thalassaemia" Nature (2010) 467(7313):318-22.
Samakoglu, S., et al., "A genetic strategy to treat sickle cell anemia by coregulating globin transgene expression and RNA interference" Nat. Biotechnol. (2006) 24(1):89-94.
Deng, W., et al., "Reactivation of developmentally silenced globin genes by forced chromatin looping" Cell (2014) 158(4):849-860.
Negre, O., et al., "Gene Therapy of the β-Hemoglobinopathies by Lentiviral Transfer of the β(A(T87Q))-Globin Gene" Hum Gene Ther. (2016) 27(2):148-65.
Bokinni, et al., "Producing and evaluating a novel lentiviral vector for beta-thalassaemia gene therapy" BMC Proceedings (2012) 6(Suppl 4):O15.
Leboulch, P., et al., "Mutagenesis of retroviral vectors transducing human beta-globin gene and beta-globin locus control region derivatives results in stable transmission of an active transcriptional structure" Embo J. (1994) 13(13):3065-76.
Arumugam, P., et al., "Genetic Therapy for Beta-Thalassemia: From the Bench to the Bedside" Hematology Am. Soc. Hematol. Educ. Program (2010) 2010(1):445-450.
Antoniou, M., et al., "Efficient 3'-end formation of human beta-globin mRNA in vivo requires sequences within the last intron but occurs independently of the splicing reaction" Nucleic Acids Res. (1998) 26(3):721-9.
El-Rashidi, et al., "The role of the soluble transferrin receptor in iron overload in children with chronic hemolytic anemia" Menoufia Med. J. (2013) 26(2):132-137.
Li, et al., "Trasnferrin therapy ameliorates disease in Beta-thalassemic mice" Nature Med. (2010) 16(2):177-183.
Huebers, et al., "The Physiology of Transferrin and Transferrin Receptors" Physiological Rev. (1987) 67(2):520-582.
Abelson, et al., "tRNA Splicing" J. Biol. Chem. (1998) 273(21):12685-12688.
Molecular Biology Web Book, Chapter 5: Posttranscriptional Processes, A4: RNA Splicing, obtained at https://www.web-books.com/MoBio/Free/Ch5A4.htm (2019) pp. 1-5.
Wikipedia, "Complementary DNA" accessed at https://en.wikipedia.org/wiki/Complentary DNA on Feb. 4, 2019, pp. 1-3.
Drakopoulou, et al., "Towards More Successful Gene Therapy Clinical Trials for Beta-Thalassemia" Current Molecular Med. (2013) 13:1314-1330.
Lisowski, et al., "Current status of globin gene therapy for the treatment of beta-thalassaemia" Br. J. Haematol. (2008) 141(3):335-45.
Guda, et al., "miRNA-embedded shRNAs for Lineage-specific BCL11A Knockdown and Hemoglobin F Induction" Molecular Therapy (2015) 23(9):1465-1474.
Fellmann, et al., "An Optimized microRNA Backbone for Effective Single-Copy RNAi" Cell Reports (2013) 5:1704-1713.
Zaiss, et al., "RNA 3' readthrough of oncoretrovirus and lentivirus: implications for vector safety and efficacy" J Virol. (2002) 76(14):7209-19.
Puthenveetil, et al., "Successful correction of the human beta-thalassemia major phenotype using a lentiviral vector" Blood (2004) 104(12):3445-53.
Wilber, et al., "Therapeutic levels of fetal hemoglobin in erythroid progeny of B-thalassemic CD34+ cells after entiviral vector-mediated gene transfer" Blood (2011) 117(10):2817-26.
Miccio, et al., "The GATA1-HS2 enhancer allows persistent and position-independent expression of a β-globin transgene" PLoS One (2011) 6(12):e27955.
Lourenco, et al., "Screening Vectors for the Treatment of ß-Globinopathies: a Quest for More Efficient Therapies" American Society of Gene & Cell Therapy, Chicago (2018) available at https://plan.core-apps.com/asgct2018/abstract/a87546bc-e7ce-4fb8-9998-d59aa67babb5.
Lourenco, et al., "HbA and HbF Simultaneous Induction by Double-Pronged Lentiviral Vector ATM1.1 Outperforms Beta-Globin-Based Gene Addition and miRNA-Based Gamma-Globin Reactivation in SCD-Derived Erythroblasts" Molecular Therapy (2019) 27(4S1):279.
Ikawa, et al., "High Levels of Transduction in CD34 Positive Cells and Toxicology Studies Using New Lentiviral Vectors for the Cure of Hemoglobinopathies" Molecular Therapy (2019) 27(4S1):285.
Han, et al., "Fetal gene therapy of a-thalassemia in a mouse model" Proc. Natl. Acad. Sci. (2007) 104(21):9007-11.
Lisowski, et al., "Locus control region elements HS1 and HS4 enhance the therapeutic efficacy of globin gene transfer in beta-thalassemic mice" Blood (2007) 110:4175-4178.
Rai, et al., "Gene therapy for hemoglobin disorders—a mini-review" J. Rare Dis. Res. Treat. (2016) 1(2): 25-31.
Dong, et al., "Gene therapy for hemoglobinopathies: progress and challenges" Transl. Res. (2013) 161(4):293-306.
Dutta, et al., "PDB-101: Molecule of the Month: Hemoglobin" (2003) Protein Data Bank, available at http://doi.org/10.2210/rcsb_pdb/mom_2003_5.
Emery, D.W., "The use of chromatin insulators to improve the expression and safety of integrating gene transfer vectors" Hum. Gene Ther. (2011) 22(6):761-74.
Fraser, et al., "Each hypersensitive site of the human beta-globin locus control region confers a different developmental pattern of expression on the globin genes" Genes Dev. (1993) 7(1):106-13.

* cited by examiner

5' ctgtcagaccaagttactcatatatactttagattgatttaaaacttcatttttaattaaaaggatctaggtgaagatcctttt
3' gacagtctggttcaaatgagtatatatgaaatctaactaaattttgaagtaaaaattaaattttcctagatccacttctaggaaa
85 ttgataatctcatgaccaaaatcccttaacgtgagtttttcgttccactgagcgtcagaccccgtagaaaagatcaaaggatcttc
aactattagagtactggttttagggaattgcactcaaaagcaaggtgactcgcagtctggggcatcttttctagttcctagaag
170 ttgagatcctttttttctgcgcgtaatctgctgcttgcaaacaaaaaaccaccgctaccagcggtggtttgtttgccggatcaa
aactctaggaaaaaagacgcgcattagacgacgaacgtttgtttttttggtggcgatggtcgccaccaaacaaacggcctagtt
255 gagctaccaactctttttccgaaggtaactggcttcagcagagcgcagataccaaatactgtccttctagtgtagccgtagttag
ctcgatggttgagaaaaggcttccattgaccgaagtcgtctcgcgtctatggtttatgacaggaagatcacatcggcatcaatc
340 gccaccacttcaagaactctgtagcaccgcctacataccctcgctctgctaatcctgttaccagtggctgctgccagtggcgataa
cggtggtgaagttcttgagacatcgtggcggatgtatgggagcgagacgattaggacaatggtcaccgacgacggtcaccgctatt
425 gtcgtgtcttaccgggttggactcaagacgatagttaccggataaggcgcagcggtcgggctgaacggggggttcgtgcacacag
cagcacagaatggcccaacctgagttctgctatcaatggcctattccgcgtcgccagcccgacttgcccccaagcacgtgtgtc
510 cccagcttggagcgaacgacctacaccgaactgagatacctacagcgtgagctatgagaaagcgccacgcttcccgaagggagaa
gggtcgaacctcgcttgctggatgtggcttgactctatggatgtcgcactcgatactctttcgcggtgcgaagggcttccctctt
595 aggcggacaggtatccggtaagcggcagggtcggaacaggagagcgcacgagggagcttccagggggaaaacgcctggtatctttta
tccgcctgtccataggccattcgccgtccagccttgtcctctcgcgtgctccctcgaaggtccccctttgcggaccatagaaat
680 tagtcctgtcgggtttcgccacctctgacttgagcgtcgatttttgtgatgctcgtcaggggggcggagcctatggaaaacgcc
atcaggacagcccaaagcggtggagactgaactcgcagctaaaaacactacgagcagtccccgcctcggatacctttttgcgg
765

FIG. 8A

FIG. 8C

```
tatataatacagtagcaaccctctattgtgtgcatcaaaggatagagataaaagacaccaaggaagctttagacaagatagagga
++++++++++++++++++++++++++++++++++++++++++++++++++++++++++++++++++++++++++++++++++++
atatattatgtcatcgttgggagataacacacgtagttcctatctctattttctgtggttccttcgaaatctgttctatctcct
```
2550

```
                                                                      MfeI
agagcaaaacaaaagtaagaccaccgcacagcaagcggccgctgatcttcagacctggaggaggagatatgagggacaattggag
++++++++++++++++++++++++++++++++++++++++++++++++++++++++++++++++++++++++++++++++++++
tctcgttttgttttcattctggtggcgtgtcgttcgccggcgactagaagtctggacctcctcctctatactccctgttaacctc
```
2635

```
aagtgaattatataaatataaagtagtaaaaattgaaccattaggagtagcacccaccaaggcaaagagaagagtggtgcagaga
++++++++++++++++++++++++++++++++++++++++++++++++++++++++++++++++++++++++++++++++++++
ttcacttaatatatttatatttcatcatttttaacttggtaatcctcatcgtgggtggtccgtttctcttctcaccacgtctct
```
2720

```
gaaaaaagagcagtgggaataggagctttgttccttgggttcttgggagcagcaggaagcactatgggcgcagcctcaatgacgc
++++++++++++++++++++++++++++++++++++++++++++++++++++++++++++++++++++++++++++++++++++
cttttttctcgtcacccttatcctcgaaacaaggaacccaagaaccctcgtcgtccttcgtgataccgcgtcggagttactgcg
```
2805

```
tgacggtacaggccagacaattattgtctggtatagtgcagcagcagaacaatttgctgagggctattgaggcgcaacagcatct
++++++++++++++++++++++++++++++++++++++++++++++++++++++++++++++++++++++++++++++++++++
actgccatgtccggtctgttaataacagaccatatcacgtcgtcgtcttgttaaacgactcccgataactccgcgttgtcgtaga
```
2890

```
gttgcaactcacagtctggggcatcaagcagctccaggcaagaatcctggctgtggaaagatacctaaaggatcaacagctcctg
++++++++++++++++++++++++++++++++++++++++++++++++++++++++++++++++++++++++++++++++++++
caacgttgagtgtcagacccgtagttcgtcgaggtccgttcttaggaccgacacctttctatggatttcctagttgtcgaggac
```
2975

```
gggatttggggttgctctggaaaactcatttgcaccactgctgtgccttggaatgctagttggagtaataaatctctggaacaga
++++++++++++++++++++++++++++++++++++++++++++++++++++++++++++++++++++++++++++++++++++
ccctaaaccccaacgagaccttttgagtaaacgtggtgacgacacggaacct tacgatcaacctcattatttagagaccttgtct
```
3060

```
tttggaatcacacgacctggatggagtgggacagagaaattaacaattacacaagcttaatacactccttaattgaagaatcgca
++++++++++++++++++++++++++++++++++++++++++++++++++++++++++++++++++++++++++++++++++++
aaaccttagtgtgctggacctacctcacctgtctctttaattgttaatgtgttcgaattatgtgaggaattaacttcttagcgt
```
3145

```
aaaccagcaagaaaagaatgaacaagaattattggaattagataaatgggcaagtttgtggaattggtttaacataacaaattgg
++++++++++++++++++++++++++++++++++++++++++++++++++++++++++++++++++++++++++++++++++++
tttggtcgttcttttcttacttgttcttaataaccttaatctatttacccgttcaaacaccttaaccaaattgtattgtttaacc
```
3230

```
ctgtggtatataaaattattcataatgatagtaggaggcttggtaggtttaagaatagttttgctgtactttctatagtaata
++++++++++++++++++++++++++++++++++++++++++++++++++++++++++++++++++++++++++++++++++++
gacaccatatattttaataagtattactatcatcctccgaaccatccaaattcttatcaaaaacgacatgaaagatatcattat
```
3315

```
gagttaggcagggatattcaccattatcgtttcagacccacctcccaacccgaggggacccgacaggcccgaaggaatagaaga
++++++++++++++++++++++++++++++++++++++++++++++++++++++++++++++++++++++++++++++++++++
ctcaatccgtccctataagtggtaatagcaaagtctgggtggagggttggggctccctgggctgtccgggcttccttatcttct
```
3400

FIG. 8D

```
                                                    HpaI
                                                    |
agaaggtggagagagagacagagacagatccattcgattagtgaacggatctcgacggtatcggttaactttaaaagaaaaggg
++++++++++++++++++++++++++++++++++++++++++++++++++++++++++++++++++++++++++++++++++++     3485
tcttccacctctctctctgtctctgtctaggtaagctaatcacttgcctagagctgccatagccaattgaaaattttcttttccc gggattgggggtacagtgcaggggaaagaatagtagacataatagcaacagacatacaaactaaagaattacaaaaacaaatta
++++++++++++++++++++++++++++++++++++++++++++++++++++++++++++++++++++++++++++++++++++     3570
ccctaaccccccatgtcacgtccccttcttatcatctgtattatcgttgtctgcatgtttgattccttaatgtttttgtttaat ClaI
         BspDI
         |
caaaaattcaaaattttatCCATAAGCTTGGGAGTTCCGCGTGTTGGGGGTGGACCATCCTCTAGGTATTGAATAAGAAAAATGA
++++++++++++++++++++++++++++++++++++++++++++++++++++++++++++++++++++++++++++++++++++     3655
gtttttaagttttaaaataGGTATTCGAACCCTCAAGGCGCACAACCCCCACCTGGTAGGAGATCCATAACTTATTCTTTTTACT AGTTAAGGTGGTTGATGGTAACACTATGCTAATAACTGCAGAGGCAGAAGCACCATAAGGGACATGATAAGGGAGCCAGCAGACG
++++++++++++++++++++++++++++++++++++++++++++++++++++++++++++++++++++++++++++++++++++     3740
TCAATTCCACCAACTACCATTGTGATACGATTATTGACGTCTCCGTCTTCGTGGTATTCCCTGTACTATTCCCTCGGTCGTCTGC TCTGATCTCTTCCTGAATGCTAATCTTAAACATCCTGAGGAAGAATGGGACTTCCATTTGGGGTGGGCCTATGATAGGGTAATAA
++++++++++++++++++++++++++++++++++++++++++++++++++++++++++++++++++++++++++++++++++++     3825
AGACTAGAGAAGGACTTACGATTAGAATTTGTAGGACTCCTTCTTACCCTGAAGGTAAACCCCACCCGGATACTATCCCATTATT GACAGTAGTGAATATCAAGCTACAAAAAGCCCCCTTTCAAATTCTTCTCAGTCCTAACTTTTCATACTAAGCCCAGTCCTTCCAA
++++++++++++++++++++++++++++++++++++++++++++++++++++++++++++++++++++++++++++++++++++     3910
CTGTCATCACTTATAGTTCGATGTTTTTCGGGGGAAAGTTTAAGAAGAGTCAGGATTGAAAAGTATGATTCGGGTCAGGAAGGTT AGCAGACTGTGAAAGAGTGATAGTTCCGGGGAGACTAGCACTGCAGATTCCGGGTCACTGTGAGTGGGGAGGCAGGGAAGAAGGG
++++++++++++++++++++++++++++++++++++++++++++++++++++++++++++++++++++++++++++++++++++     3995
TCGTCTGACACTTTCTCACTATCAAGGCCCTCTGATCGTGACGTCTAAGGCCCAGTGACACTCACCCCCTCCGTCCCTTCTTCCC CTCACAGGACAGTCAAACCATGCCCCCTGTTTTTCCTTCTTCAAGTAGACCTCTATAAGACAACAGAGACAACTAAGGCTGAGTG
++++++++++++++++++++++++++++++++++++++++++++++++++++++++++++++++++++++++++++++++++++     4080
GAGTGTCCTGTCAGTTTGGTACGGGGGACAAAAAGGAAGAAGTTCATCTGGAGATATTCTGTTGTCTCTGTTGATTCCGACTCAC GCCAGGGGAGGAGAAACCATCTCGCCGTAAAACATGGAAGGAACACTTCAGGGGAAAGTGGTATCTCTAAGCAAGAGAACTGAG
++++++++++++++++++++++++++++++++++++++++++++++++++++++++++++++++++++++++++++++++++++     4165
CGGTCCCCTCCTCTTTGGTAGAGCGGCATTTTGTACCTTCCTTGTGAAGTCCCCTTTCCACCATAGAGATTCGTTCTCTTGACTC
```

FIG. 8E

FIG. 8F

```
AAGGCGCCATCTCGCCCCTCGACCCAGATCGCTCCCGGCCCGCCGCTCACCTTGAAGTTGACCGGGTCCACCCGAAGCTTGTGCG
++++++++++++++++++++++++++++++++++++++++++++++++++++++++++++++++++++++++++++++++++++++    4930
TTCCGCGGTAGAGCGGGGAGCTGGGTCTAGCGAGGGCCGGGCGGCGAGTGGAACTTCAACTGGCCCAGGTGGGCTTCGAACACGC
```
HBA Intron 2 | HBA Exon 2

BstXI
```
CGTGCAGGTCGCTCAGGGCGGACAGCGCGTTGGGCATGTCGTCCACGTGCGCCACGGCGTTGGTCAGCGCGTCGGCCACCTTCTT
++++++++++++++++++++++++++++++++++++++++++++++++++++++++++++++++++++++++++++++++++++++    5015
GCACGTCCAGCGAGTCCCGCCTGTCGCGCAACCCGTACAGCAGGTGCACGCGGTGCCGCAACCAGTCGCGCAGCCGGTGGAAGAA
```
HBA Exon 2

```
GCCGTGGCCCTTAACCTGGGCAGAGCCGTGGCTCAGGTCGAAGTGCGGGAAGTAGGTCTTGGTGGTGGGGAAGGACAGGAACATC
++++++++++++++++++++++++++++++++++++++++++++++++++++++++++++++++++++++++++++++++++++++    5100
CGGCACCGGGAATTGGACCCGTCTCGGCACCGAGTCCAGCTTCACGCCCTTCATCCAGAACCACCACCCCTTCCTGTCCTTGTAG
```
HBA Exon 2

```
CTGCGGGGAGAAGCAGAGTGAGGGGTGGGGTTTGGGTCCGGGGCCAGGACGGTTGAGGGTGGCCTGTGGGTCCGGCGGGCGAGG
++++++++++++++++++++++++++++++++++++++++++++++++++++++++++++++++++++++++++++++++++++++    5185
GACGCCCCTCTTCGTCTCACTCCCCACCCCAAACCCAGGCCCCGGTCCTGCCAACTCCCACCGGACACCCAGGCCCGCCCGCTCC
```
HBA Intron 1

```
AGCCCGGGTCGGAGCAGGGGAGGGAGCCTCACCTCTCCAGGGCCTCCGCACCATACTCGCCAGCGTGCGCGCCGACCTTACCCCA
++++++++++++++++++++++++++++++++++++++++++++++++++++++++++++++++++++++++++++++++++++++    5270
TCGGGCCCAGCCTCGTCCCCTCCCTCGGAGTGGAGAGGTCCCGGAGGCGTGGTATGAGCCGTCGCACGCGCGGCTGGAATGGGCT
```
HBA Intron 1 | HBA Exon 1

PshAI
```
GGCGGCCTTGACGTTGGTCTTGTCGGCAGGAGACAGCACCATGGTGGGTTCTCTCTGAGTCTGTGGGGACCAGAAGAGTAAGCAA
++++++++++++++++++++++++++++++++++++++++++++++++++++++++++++++++++++++++++++++++++++++    5355
CCGCCGGAACTGCAACCAGAACAGCCGTCCTCTGTCGTGGTACCACCCAAGAGAGACTCAGACACCCCTGGTCTTCTCATTCGTT
```
HBA Exon 1 | HBA 5 Prime UTR

```
TAGATGGCTCTGCCCTGACTTTTATGCCCAGCCCTGGCTCCTGCCCTCCCTGCTCCTGGGAGTAGATTGGCCAACCCTAGGGTGT
++++++++++++++++++++++++++++++++++++++++++++++++++++++++++++++++++++++++++++++++++++++    5440
ATCTACCGAGACGGGACTGAAAATACGGGTCGGGACCGAGGACGGGAGGGACGAGGACCCTCATCTAACCGGTTGGGATCCCACA
```
Beta Globin Promoter 200bp

```
GGCTCCACAGGGTGAGGTCTAAGTGATGACAGCCGTACCTGTCCTTGGCTCTTCTGGCACTGGCTTAGGAGTTGGACTTCAAACC
++++++++++++++++++++++++++++++++++++++++++++++++++++++++++++++++++++++++++++++++++++++    5525
CCGAGGTGTCCCACTCCAGATTCACTACTGTCGGCATGGACAGGAACCGAGAAGACCGTGACCGAATCCTCAACCTGAAGTTTGG
```
Beta Globin Promoter 200bp

FIG. 8G

```
CTCAGCCCTCCCTCTAAGATATATCTCTTGGCCCCATACCATCAGTACAAATTGCTACTAAAAACATCCTCCTTTGCAAGTGTAT
++++++++++++++++++++++++++++++++++++++++++++++++++++++++++++++++++++++++++++++++++++    5610
GAGTCGGGAGGGAGATTCTATATAGAGAACCGGGGTATGGTAGTCATGTTTAACGATGATTTTTGTAGGAGGAAACGTTCACATA
```
Beta Globin Promoter 200bp

```
         BstZ17I
TTACGTAgtatacctcaagcctcattcagacactagtgtcaccagtctcctcatataccattgtatttcttcttcttgctggt
++++++++++++++++++++++++++++++++++++++++++++++++++++++++++++++++++++++++++++++++++++    5695
AATGCATcatatggagttcggagtaagtctgtgatcacagtggtcagaggagtatatggataacataaagaagaagaacgacca
```

```
ttagtcatgtttctgggagcttagggcttatttatttttgtttgttttctaatcaacagagatgggcaaaccattatttt
++++++++++++++++++++++++++++++++++++++++++++++++++++++++++++++++++++++++++++++++++++    5780
aatcagtacaaaagaccctcgaatcccgaataaaataaaacaaaacaaaagattagttgtctctaccgtttgggtaataaaaa
```

```
ttctttagacttgggatggtgatagctgggcagcgtcagaaactgtgtgtggatatagataagagctcaggactatgctgagctg
++++++++++++++++++++++++++++++++++++++++++++++++++++++++++++++++++++++++++++++++++++    5865
aagaaatctgaaccctaccactatcgacccgtcgcagtctttgacacacacctatatctattctcgagtcctgatacgactcgac
```

```
tgatgaggagggggcctagctaaaggcagtgagagtcagaatgctcctgctattgccttctcagtcccaogcttggtttctaca
++++++++++++++++++++++++++++++++++++++++++++++++++++++++++++++++++++++++++++++++++++    5950
actactcctccccggatcgattccgtcactctcagtcttacgaggacgataacggaagagtcaggggtgcgaaccaaagatgt
```

```
caagtagatacatagaaaaggctataggttagtgtttgagagtcctgcatgattagttgctcagaaatgcccgataaatatgtta
++++++++++++++++++++++++++++++++++++++++++++++++++++++++++++++++++++++++++++++++++++    6035
gttcatctatgtatcttttccgatatccaatcacaaactctcaggacgtactaatcaacgagtctttacgggctatttatacaat
```

```
tgtgtgtttatgtatatatatgtttatatatatatatatgtgtgtgtgtgtgtgtgtgtgttgtgtttacaaatatgtgatt
++++++++++++++++++++++++++++++++++++++++++++++++++++++++++++++++++++++++++++++++++++    6120
acacacaaatacatatatacaaaatatatatatatacacacacacacacacacacacaacacaaatgtttatacactaa
```

```
                                                                    XbaI
atcatcaaaacgtgagggctaaagtgaccagataacttgcaagtcctaggataccaggaaaGtCTAGAATATGTCACATTCTGTC
++++++++++++++++++++++++++++++++++++++++++++++++++++++++++++++++++++++++++++++++++++    6205
tagtagttttgcactcccgatttcactggtctattgaacgttcaggatcctatggtccttrCaGATCTTATACAGTGTAAGACAG
```

FIG. 8H

FIG. 8I

TAGGAAGGCCATAGCTCTGTGCTGAACTGTTAGGCCACTGGTCCAGAGAGTGTGCATCTCCTTTGATCCTCATAATAAGCCTATG
ATCCTTCGGGTATCGAGACAGGACTTGACAATCCGGTGACCAGGTCTCTCACACGTAGAGGAAACTAGGAGTATTATTCGGATAC
7055

AGATAGACACAATTATTACTCTTACTTTATAGATGATGATCCTGAAAACATAGGAGTCAAGGCACTTGCCCCTAGCTGGGGGTAT
TCTATCTGTGTTAATAATGAGAATGAAATATCTACTACTAGGACTTTTGTATCCTCAGTTCCGTGAACGGGGATCGACCCCCATA
7140

AGGGGAGCAGTCGCATGTAGTAGTAGAATGAAAAATGCTGCTATGCTGTGCCTCGCCCACCTTTCCCATGTCTGCCGCTCTACTCA
TCCCCTCGTCAGGGTACATCATCATCTTACTTTTTACGACGATACGACACGGAGGGGGTGGAAAGGGTACAGACGGCGAGATGAGT
7225

TGGTCTATCTCTCCTGGCTCCTGGGAGTCATGGACTCCACCCAGCACCACCAACCTGACCTAACCAGCTATCTGAGCCTGCCAGC
ACCAGATAGAGAGGACCGAGGACCCTCAGTACCTGAGGTGGGTCGTGGTGGTTGGACTGGATTGGTGGATAGACTCGGACGGTCG
7310

CTATAACCCATCTGGGCCCTGATAGCTGGTGGCCAGCCCTGACCCCACCCCACCCTCCCTGGAACCTCTGATAGACACATCTGGC
GATATTGGGTAGACCCGGGACTATCGACCACCGGTCGGGACTGGGGTGGGGTGGGAGGGACCTTGGAGACTATCTGTGTAGACCG
7395

ACACCAGCTCGCAAAGTCACCGTGAGGGTCTTGTGTTTGCTGAGTCAAAATTCCTTGAAATCCAAGTCCTTAGAGACTCCTGCTG
TGTGGTCGAGCGTTTCAGTGGCACTCCCAGAACACAAACGACTCAGTTTTAAGGAACTTTAGGTTCAGGAATCTCTGAGGACGAG
7480

CCAAATTTACAGTCATAGACTTCTTCATGGCTGTCTCCTTTATCCACAGAATGATTCCTTTGCTTCATTGCCCCATCCATCTGAT
GGTTTAAATGTCAGTATCTGAAGAAGTACCGACAGAGGAAATAGGTGTCTTACTAAGGAAACGAAGTAACGGGGTAGGTAGACTA
7565

CCTCCTCATCAGTGCAGCACAGGGCCCATGAGCAGTAGCTGCAGAGTCTCACATAGGTCTGGCACTGCCTCTGACATGTCCGACC
GGAGGAGTAGTCACGTCGTGTCCCGGGTACTCGTCATCGACGTCTCAGAGTGTATCCAGACCGTGACGGAGACTGTACAGGCTGG
7650

AgeI
TTAGGCAAATGCTTGACTCTTCTGAGCTCaccggtactagtgcatgcaaatctgacactcagtgggcctggtgaaggtgagaat
AATCCGTTTACGAACTGAGAAGACTCGAGtggccatgatcacgtacgtttagactgtgagtcacccggaccactt ccactctta
7735

FIG. 8J

```
tttattgctgaatgagagcctctggggacatcttgccagtcaatgagtctcaggttcaatttccttctcagtcttggagtaacag
++++++++++++++++++++++++++++++++++++++++++++++++++++++++++++++++++++++++++++++++++++++    7820
aaataacgacttactctcggagaccctgtagaacggtcagttactcagagtccaagttaaaggaagagtcagaacctcattgtc
```

```
aagctcatgcatttaataaacggaaattttgtattgaaatgagagccattggaaatcatttactccagactcctacttataaaa
++++++++++++++++++++++++++++++++++++++++++++++++++++++++++++++++++++++++++++++++++++++    7905
ttcgagtacgtaaattatttgcctttaaaacataactttactctcggtaaccttagtaaatgaggtctgaggatgaatatttt
```
HS4

```
gagaaactgaggctcagagaagggtggggactttctcagtatgacatggaaatgatcaggcttggattcaaagctcctgactttc
++++++++++++++++++++++++++++++++++++++++++++++++++++++++++++++++++++++++++++++++++++++    7990
ctctttgactccgagtctcttcccacccctgaaagagtcatactgtaccttactagtccgaacctaagttccgaggactgaaag
```
HS4

```
tgtctagtgtatgtgcagtgagcccctttcctctaactgaaagaaggaaaaaaaaatggaacccaaaatattctacatagtttc
++++++++++++++++++++++++++++++++++++++++++++++++++++++++++++++++++++++++++++++++++++++    8075
acagatcacatacacgtcactcggggaaaaggagattgacttcttcctttttttttaccttgggtttataagatgtatcaaag
```
HS4

```
catgtcacagccagggctgggcagtctcctgttatttctttaaaataaatatatcatttaaatgcataaataagcaaaccctgc
++++++++++++++++++++++++++++++++++++++++++++++++++++++++++++++++++++++++++++++++++++++    8160
gtacagtgtcggtcccgacccgtcagaggacaataagaaaattttatttatatagtaaatttacgtattattcgtttgggacg
```
HS4

```
tcgggaatgggagggagagtctctggagtccaccccttctcggccctggctctgcagatagtgctatcaaagccctgacagagcc
++++++++++++++++++++++++++++++++++++++++++++++++++++++++++++++++++++++++++++++++++++++    8245
agcccttaccctccctctcagagacctcaggtggggaagagccgggaccgagacgtctatcacgatagtttcgggactgtctcgg
```
HS4

```
ctgcccattgctgggccttggagtgagtcagcctagtagagaggcagggcaagccatctcatagctgctgagtgggagagagaaa
++++++++++++++++++++++++++++++++++++++++++++++++++++++++++++++++++++++++++++++++++++++    8330
gacgggtaacgacccggaacctcactcagtcggatcatctctccgtcccgttcggtagagtatcgacgactcaccctctctctt
```
HS4

```
agggctcattgtctataaactcaggtcatggctattcttattctcacactaagaaaaagaatgagatgtctacatataccctgcg
++++++++++++++++++++++++++++++++++++++++++++++++++++++++++++++++++++++++++++++++++++++    8415
tcccgagtaacagatatttgagtccagtaccgataagaataagagtgtgattctttttcttactctacagatgtatatgggacgc
```
HS4

```
tccctcttgtgtactggggtccccaagagctctctaaaagtgatggcaaagtcattgcgctagatgccatcccatctattataa
++++++++++++++++++++++++++++++++++++++++++++++++++++++++++++++++++++++++++++++++++++++    8500
agggagaacacatgaccccaggggttctcgagagattttcactaccgtttcagtaacgcgatctacggtagggtagataatatt
```
HS4

FIG. 8K

FIG. 8L

```
                                                                    NheI    BmtI
tgtgcccgtctgttgtgtgactctggtaactagagatccctcagacccttttagtcagtgtggaaaatctctagcagGCTAGCaa
++++++++++++++++++++++++++++++++++++++++++++++++++++++++++++++++++++++++++++++++++++    9350
acacgggcagacaacacactgagaccattgatctctaggagtctgggaaaatcagtcacacctttagagatcgtcCGATCGtt
―――――――――――――――――――――――HIV-1 5 LTR――――――――――――――――――――――>

BsiWI            PacI        SalI
acaaaagaCGTACGagctatgctTTAATTAAagctatgctGTCGACaatcaacctctggattacaaaatttgtgaaagattgact
++++++++++++++++++++++++++++++++++++++++++++++++++++++++++++++++++++++++++++++++++++    9435
tgttttctGCATGCtcgatacgaAATTAATTtcgatacgaCAGCTGttagttggagacctaatgtttaaacacttctaactga
                                         ―――――――――――――WPRE―――――――――――――> ggtattcttaactatgttgctcctttacgctatgtggatacgctgctttaatgcctttgtatcatgctattgcttcccgtatgg
++++++++++++++++++++++++++++++++++++++++++++++++++++++++++++++++++++++++++++++++++++    9520
ccataagaattgatacaacgaggaaaatgcgatacacctatgcgacgaaattacggaaacatagtacgataacgaaggcatacc
―――――――――――――――――――――――WPRE――――――――――――――――――――――> ctttcattttctcctccttgtataaatcctggttgctgtctctttatgaggagttgtggcccgttgtcaggcaacgtggcgtggt
++++++++++++++++++++++++++++++++++++++++++++++++++++++++++++++++++++++++++++++++++++    9605
gaaagtaaaagaggaggaacatatttaggaccaacgacagagaaatactcctcaacaccgggcaacagtccgttgcaccgcacca
―――――――――――――――――――――――WPRE――――――――――――――――――――――>

PflMI
gtgcactgtgtttgctgacgcaacccccactggttggggcattgccaccacctgtcagctcctttccgggactttcgctttcccc
++++++++++++++++++++++++++++++++++++++++++++++++++++++++++++++++++++++++++++++++++++    9690
cacgtgacacaaacgactgcgttgggggtgaccaaccccgtaacggtggtggacagtcgaggaaaggccctgaaagcgaaaggggg
―――――――――――――――――――――――WPRE――――――――――――――――――――――> ctccctattgccacggcggaactcatcgccgcctgccttgcccgctgctggacaggggctcggctgttgggcactgacaattccg
++++++++++++++++++++++++++++++++++++++++++++++++++++++++++++++++++++++++++++++++++++    9775
gagggataacggtgccgccttgagtagcggcggacgaacggcgacgacctgtccccgagccgacaacccgtgactgttaaggc
―――――――――――――――――――――――WPRE――――――――――――――――――――――> tggtgttgtcggggaagctgacgtcctttccatggctgctcgcctgtgttgccacctggattctgcgcgggacgtccttctgcta
++++++++++++++++++++++++++++++++++++++++++++++++++++++++++++++++++++++++++++++++++++    9860
accacaacagccccttcgactgcaggaaaggtaccgacgagcggacacaacggtggacctaagacgcgcctgcaggaagacgat
―――――――――――――――――――――――WPRE――――――――――――――――――――――> cgtcccttcggccctcaatccagcggaccttcctcccgcggcctgctgccggctctgcggcctcttccgcgtcttcgccttgc
++++++++++++++++++++++++++++++++++++++++++++++++++++++++++++++++++++++++++++++++++++    9945
gcagggaagccgggagttaggtcgcctggaagaaggcgccggacgacggccgagacgccggagaagcgcagaagcggaagcg
―――――――――――――――――――――――WPRE――――――――――――――――――――――>

◄―FactorXa site
```

FIG. 8M

FIG. 8N

BsmBI gagctattccagaagtagtgaggaggcttttttggAGGCCTaggcttttgcgtcgagacgtacccaattcgccctatagtgagtc
ctcgataaggtcttcatcactcctccgaaaaaaccTCCGGAtcggaaaacgcagctctgcatgggttaagcgggatatcactcag 10,710 gtattacgcgcgctcactggccgtcgttttacaacgtcgtgactgggaaaaccctggcgttacccaacttaatcgccttgcagca
cataatgcgcgcgagtgaccggcagcaaaatgttgcagcactgaccctttgggaccgcaatgggttgaattagcggaacgtcgt 10,795 catccccttcgccagctggcgtaatagcgaagaggcccgcaccgatcgcccttcccaacagttgcgcagcctgaatggcgaat
gtaggggaaagcggtcgaccgcattatcgcttctccgggcgtggctagcgggaaggggttgtcaacgcgtcggacttaccgctta 10,880 ggcgcgacgcgccctgtagcggcgcattaagcgcggcgggtgtggtggttacgcgcagcgtgaccgctacacttgccagcgccct
ccgcgctgcgcgggacatcgccgcgtaattcgcgccgccacaccaccaatgcgcgtcgcactggcgatgtgaacggtcgcggga 10,965

LacZ alpha agcgcccgctcctttcgctttcttcccttcctttctcgccacgttcgccggctttccccgtcaagctctaaatcggggctccct
tcgcgggcgaggaaagcgaaagaagggaaggaaagagcggtgcaagcggccgaaaggggcagttcgagatttagccccgaggga 11,050 ttagggttccgatttagtgctttacggcacctcgaccccaaaaaacttgattagggtgatggttcacgtagtggccatcgccct
aatcccaaggctaaatcacgaaatgccgtggagctgggggttttttgaactaatcccactaccaagtgcatcacccggtagcggga 11,135 gatagacggtttttcgccctttgacgttggagtccacgttctttaatagtggactcttgttccaaactggaacaacactcaaccc
ctatctgccaaaaagcgggaaactgcaacctcaggtgcaagaaattatcacctgagaacaaggtttgaccttgttgtgagttggg 11,220

FIG. 80

FIG. 8P

ATACCAAACGACGAGCGTGACACCACGATGCCTGTAGCAATGGCAACAACGTTGCGCAAACTATTAACTGGCGAACTACTTACTC
TATGGTTTGCTGCTCGCACTGTGGTGCTACGGACATCGTTACCGTTGTTGCAACGCGTTTGATAATTGACCGCTTGATGAATGAG
AmpR 12,070

TAGCTTCCCGGCAACAATTAATAGACTGGATGGAGGCGGATAAAGTTGCAGGACCACTTCTGCGCTCGGCCCTTCCGGCTGGCTG
ATCGAAGGGCCGTTGTTAATTATCTGACCTACCTCCGCCTATTTCAACGTCCTGGTGAAGACGCGAGCCGGGAAGGCCGACCGAC
AmpR 12,155

GTTTATTGCTGATAAATCTGGAGCCGGTGAGCGTGGGTCTCGCGGTATCATTGCAGCACTGGGGCCAGATGGTAAGCCCTCCCGT
CAAATAACGACTATTTAGACCTCGGCCACTCGCACCCAGAGCGCCATAGTAACGTCGTGACCCCGGTCTACCATTCGGGAGGGCA
AmpR 12,240

ATCGTAGTTATCTACACgacgggagtcaggcaactatggatgaacgaaatagacagatcgctgagataggtgcctcactgatta
TAGCATCAATAGATGTGctgccctcagtccgttgataccactgctttatctgtctagcgactctatccacggagtgactaat
AmpR 12,325 agcattggtaa 3'
+++++++++ ... 12,335
tcgtaaccatt 5'

FIG. 8Q

```
5'  ctgtcagaccaagttactcatatataacttagattgatttaaaacttcattttaatttaaaaggatctaggtgaagatcctttt
    ++++++++++++++++++++++++++++++++++++++++++++++++++++++++++++++++++++++++++++++++++++  85
3'  gacagtctggttcaatgagtatatatgaatctaactaaattttgaagtaaaaattaaatttcctagatccacttctaggaaaa ttgataatctcatgaccaaaatcccttaacgtgagttttcgttccactgagcgtcagaccccgtagaaaagatcaaaggatcttc
    ++++++++++++++++++++++++++++++++++++++++++++++++++++++++++++++++++++++++++++++++++++  170
    aactattagagtactggttttagggaattgcactcaaaagcaaggtgactcgcagtctggggcatcttttctagtttcctagaag
                                                                        [CDS_0000]  > ttgagatcctttttttctgcgcgtaatctgctgcttgcaaacaaaaaaaccaccgctaccagcggtggtttgtttgccggatcaa
    ++++++++++++++++++++++++++++++++++++++++++++++++++++++++++++++++++++++++++++++++++++  255
    aactctaggaaaaaagacgcgcattagacgacgaacgtttgttttttttggtggcgatggtcgccaccaaacaaacggcctagtt
    [CDS_0000]                                                                       > gagctaccaactctttttccgaaggtaactggcttcagcagagcgcagataccaaatactgtccttctagtgtagccgtagttag
    ++++++++++++++++++++++++++++++++++++++++++++++++++++++++++++++++++++++++++++++++++++  340
    ctcgatggttgagaaaaggcttccattgaccgaagtcgtctcgcgtctatggtttatgacaggaagatcacatcggcatcaatc
    [CDS_0000]                                                                       > gccaccacttcaagaactctgtagcaccgcctacatacctcgctctgctaatcctgttaccagtggctgctgccagtggcgataa
    ++++++++++++++++++++++++++++++++++++++++++++++++++++++++++++++++++++++++++++++++++++  425
    cggtggtgaagttcttgagacatcgtggcggatgtatggagcgagacgattaggacaatggtcaccgacgacggtcaccgctatt
    [CDS_0000]                                                                       > gtcgtgtcttaccgggttggactcaagacgatagttaccggataaggcgcagcggtcgggctgaacggggggttcgtgcacacag
    ++++++++++++++++++++++++++++++++++++++++++++++++++++++++++++++++++++++++++++++++++++  510
    cagcacagaatggccccacctgagttctgctatcaatggcctattccgcgtcgccagcccgacttgcccccaagcacgtgtgtc
    [CDS_0000]                                                                       > cccagcttggagcgaacgacctacaccgaactgagatacctacagcgtgagctatgagaaagcgccacgcttcccgaagggagaa
    ++++++++++++++++++++++++++++++++++++++++++++++++++++++++++++++++++++++++++++++++++++  595
    gggtcgaaccctcgcttgctggatgtggcttgactctatggatgtcgcactcgatactctttcgcggtgcgaagggcttccctctt
    [CDS_0000]                                                                       > aggcggacaggtatccggtaagcggcagggtcggaacaggagagcgcacgagggagcttccagggggaaacgcctggtatcttta
    ++++++++++++++++++++++++++++++++++++++++++++++++++++++++++++++++++++++++++++++++++++  680
    tccgcctgtccataggccattcgccgtcccagccttgtcctctcgcgtgctccctcgaaggtcccccttttgcggaccatagaaat
    [CDS_0000]                                                                       > tagtcctgtcgggtttcgccacctctgacttgagcgtcgatttttgtgatgctcgtcaggggggcggagcctatggaaaaacgcc
    ++++++++++++++++++++++++++++++++++++++++++++++++++++++++++++++++++++++++++++++++++++  765
    atcaggacagcccaaagcggtggagactgaactcgcagctaaaaacactacgagcagtcccccgcctcggatacctttttgcgg
    [CDS_0000]                                                                       >
```

FIG. 9A

FIG. 9C

```
tatataatacagtagcaaccctctattgtgtgcatcaaaggatagagataaaagacaccaaggaagctttagacaagatagagga
++++++++++++++++++++++++++++++++++++++++++++++++++++++++++++++++++++++++++++++++++++   2550
atatattatgtcatcgttgggagataacacacgtagtttcctatctctatttctgtggttccttcgaaatctgttctatctcct
```

Mfel
```
agagcaaaacaaaagtaagaccaccgcacagcaagcggccgctgatcttcagacctggaggaggagatatgagggacaattggag
++++++++++++++++++++++++++++++++++++++++++++++++++++++++++++++++++++++++++++++++++++   2635
tctcgttttgttttcattctggtggcgtgtcgttcgccggcgactagaagtctggacctcctcctctataccctgttaacctc
```

```
aagtgaattatataaatataaagtagtaaaaattgaaccattaggagtagcacccaccaaggcaaagagaagagtggtgcagaga
++++++++++++++++++++++++++++++++++++++++++++++++++++++++++++++++++++++++++++++++++++   2720
ttcacttaatatatttatatttcatcatttttaacttggtaatcctcatcgtgggtggttccgtttctcttctcaccacgtctct
```

```
gaaaaagagcagtgggaataggagcttgttccttgggttcttgggagcagcaggaagcactatgggcgcagcctcaatgacgc
++++++++++++++++++++++++++++++++++++++++++++++++++++++++++++++++++++++++++++++++++++   2805
cttttttctcgtcacccttatcctcgaaacaaggaacccaagaaccctcgtcgtccttcgtgatacccgcgtcggagttactgcg
```

```
tgacggtacaggccagacaattattgtctggtatagtgcagcagcagaacaattgctgagggctattgaggcgcaacagcatct
++++++++++++++++++++++++++++++++++++++++++++++++++++++++++++++++++++++++++++++++++++   2890
actgccatgtccggtctgttaataacagaccatatcacgtcgtcgtcttgttaaacgactcccgataactccgcgttgtcgtaga
```

```
gttgcaactcacagtctggggcatcaagcagctccagcaagaatcctggctgtggaaagatacctaaaggatcaacagctcctg
++++++++++++++++++++++++++++++++++++++++++++++++++++++++++++++++++++++++++++++++++++   2975
caacgttgagtgtcagacccgtagttcgtcgaggtccgttcttaggaccgacacctttctatggatttcctagttgtcgaggac
```

```
gggatttggggttgctctggaaaactcatttgcaccactgctgtgccttggaatgctagttggagtaataaatctctggaacaga
++++++++++++++++++++++++++++++++++++++++++++++++++++++++++++++++++++++++++++++++++++   3060
ccctaaacccccaacgagacctttgagtaaacgtggtgacgacacggaaccttacgatcaacctcattatttagagaccttgtct
```

```
tttggaatcacacgacctggatggagtgggacagagaaattaacaattacacaagcttaatacactccttaattgaagaatcgca
++++++++++++++++++++++++++++++++++++++++++++++++++++++++++++++++++++++++++++++++++++   3145
aaaccttagtgtgctggacctacctcaccctgtctctttaattgttaatgtgttcgaattatgtgaggaattaacttcttagcgt
```

```
aaaccagcaagaaaagaatgaacaagaattattggaattagataaatgggcaagtttgtggaattggtttaacataacaaattgg
++++++++++++++++++++++++++++++++++++++++++++++++++++++++++++++++++++++++++++++++++++   3230
tttggtcgttcttttcttacttgttcttaataaccttaatctatttacccgttcaaacaccttaaccaaattgtattgtttaacc
```

```
ctgtggtatataaaattattcataatgatagtaggaggcttggtaggtttaagaatagtttttgctgtactttctatagtgaata
++++++++++++++++++++++++++++++++++++++++++++++++++++++++++++++++++++++++++++++++++++   3315
gacaccatatattttaataagtattactatcatcctccgaaccatccaaattcttatcaaaaacgacatgaaagatatcacttat
```

```
gagttaggcagggatatttcaccattatcgtttcagacccacctcccaaccccgaggggacccgacaggcccgaaggaatagaaga
++++++++++++++++++++++++++++++++++++++++++++++++++++++++++++++++++++++++++++++++++++   3400
ctcaatccgtccctataagtggtaatagcaaagtctgggtggaggggttggggctcccctgggctgtccgggcttccttatcttct
```

FIG. 9D

```
                                              HpaI
agaaggtggagagagagacagagacagatccattcgattagtgaacggatctcgacggtatcggttaacttttaaagaaaaggg
++++++++++++++++++++++++++++++++++++++++++++++++++++++++++++++++++++++++++++++++++++  3485
tcttccacctctctctctgtctctgtctaggtaagctaatcacttgcctagagctgccatagccaattgaaaattttcttttccc gggattgggggtacagtgcaggggaaagaatagtagacataatagcaacagacatacaaactaaagaattacaaaaacaaatta
++++++++++++++++++++++++++++++++++++++++++++++++++++++++++++++++++++++++++++++++++++  3570
ccctaaccccccatgtcacgtcccctttcttatcatctgtattatcgttgtctgtatgtttgatttcttaatgttttgtttaat ClaI
       BspDI
caaaaattcaaaattttatCGATAAGCTTGGGACTTCCGCGTGTTGGGGGTGGACCATCCTCTAGGTATTGAATAAGAAAATGA
++++++++++++++++++++++++++++++++++++++++++++++++++++++++++++++++++++++++++++++++++++  3655
gttttttaagttttaaaataGCTATTCGAACCCTCAAGGCGCACAACCCCCACCTGGTAGGAGATCCATAACTTATTCTTTTACT AGTTAAGGTGGTTCATGGTAACACTATGCTAATAACTGCAGAGCCAGAAGCACCATAAGGGACATGATAAGGGAGCCAGCAGACC
++++++++++++++++++++++++++++++++++++++++++++++++++++++++++++++++++++++++++++++++++++  3740
TCAATTCCACCAACTACCATTGTGATACGATTATTGACGTCTCGGTCTTCGTGGTATTCCCTGTACTATTCCCTCGGTCGTCTGG TCTGATCTCTTCCTGAATGCTAATCTTAAACATCCTGAGGAAGAATGGGACTTCCATTTGGGGTGGGCCTATGATAGGGTAATAA
++++++++++++++++++++++++++++++++++++++++++++++++++++++++++++++++++++++++++++++++++++  3825
AGACTAGAGAAGGACTTACGATTAGAATTTGTAGGACTCCTTCTTACCCTGAAGGTAAACCCCACCCGGATACTATCCCATTATT GACAGTAGTGAATATCAAGCTACAAAAAGCCCCCTTTCAAATTCTTCTCAGTCCTAACTTTTCATACTAAGCCCAGTCCTTCCAA
++++++++++++++++++++++++++++++++++++++++++++++++++++++++++++++++++++++++++++++++++++  3910
CTGTCATCACTTATAGTTCGATGTTTTTCGGGGGAAAGTTTAAGAAGAGTCAGGATTGAAAAGTATGATTCGGGTCAGGAAGGTT AGCAGACTGTGAAAGAGTGATAGTTCCGGGAGACTAGCACTGCAGATTCCGGGTCACTGTGAGTGGGGGAGGCAGGGAAGAAGGG
++++++++++++++++++++++++++++++++++++++++++++++++++++++++++++++++++++++++++++++++++++  3995
TCGTCTGACACTTTCTCACTATCAAGGCCCTCTGATCGTGACGTCTAAGGCCCAGTGACACTCACCCCCTCCGTCCCTTCTTCCC CTCACAGGACAGTCAAACCATGCCCCCTGTTTTTCCTTCTTCAAGTAGACCTCTATAAGACAACAGAGACAACTAAGGCTGAGTG
++++++++++++++++++++++++++++++++++++++++++++++++++++++++++++++++++++++++++++++++++++  4080
GAGTGTCCTGTCAGTTTGGTACGGGGGACAAAAAGGAAGAAGTTCATCTGGAGATATTCTGTTGTCTCTGTTGATTCCGACTCAC GCCAGGCGAGGAGAAACCATCTCGCCGTAAAACATGGAAGGAACACTTCAGGGGAAAGGTGGTATCTCTAAGCAAGAGAACTGAG
++++++++++++++++++++++++++++++++++++++++++++++++++++++++++++++++++++++++++++++++++++  4165
CGGTCCGCTCCTCTTTGGTAGAGCGGCATTTTGTACCTTCCTTGTGAAGTCCCCTTTCCACCATAGAGATTCGTTCTCTTGACTC
```

FIG. 9E

```
AAGGCGCCATCTCGCCCCTCGACCCAGATCGCTCCCGGCCCGCGCTCACCTTGAAGTTGACCGGGTCCAGCCGAAGCTTGTGCG
++++++++++++++++++++++++++++++++++++++++++++++++++++++++++++++++++++++++++++++++++++   4930
TTCCGCGGTAGAGCGGGGAGCTGGGTCTAGCGAGGGCCGGGCGGCGAGTGGAACTTCAACTGGCCCAGGTGGGCTTCGAACACGC
```

```
                                                                BstXI
CGTGCAGGTCGCTCAGGGCGGACAGCGCGTTGGGCATGTCGTCCACGTGCGCCACGGCGTTGGTCAGCGCGTCGGCCACCTTCTT
++++++++++++++++++++++++++++++++++++++++++++++++++++++++++++++++++++++++++++++++++++   5015
GCACGTCCAGCGAGTCCCGCCTGTCGCGCAACCCGTACAGCAGGTGCACGCGGTGCCGCAACCAGTCGCGCAGCCGGTGGAAGAA
```

```
GCCGTGGCCCTTAACCTGGGCAGAGCCGTGGCTCAGGTCGAAGTGCGGGAAGTAGGTCTTGGTGGTGGGGAAGGACAGGAACATC
++++++++++++++++++++++++++++++++++++++++++++++++++++++++++++++++++++++++++++++++++++   5100
CGGCACCGGGAATTGGACCCGTCTCGGCACCGAGTCCAGCTTCACGCCCTTCATCCAGAACCACCACCCCTTCCTGTCCTTGTAG
```

```
CTGCGGGGAGAAGCAGAGTGAGGGGTGGGGTTTGGGTCCGGGGCCAGGACGGTTGAGGGTGGCCTGTGGGTCCGGCCGGGCCAGG
++++++++++++++++++++++++++++++++++++++++++++++++++++++++++++++++++++++++++++++++++++   5185
GACGCCCCTCTTCGTCTCACTCCCCACCCCAAACCCAGGCCCCGGTCCTGCCAACTCCCACCGGACACCCAGGCCCGCCCGCTCC
```

```
AGCCCGGGTCGGAGCAGGGGAGGGAGCCCTCACCTCTCCAGGGCCTCGGCGCCATACTCGCCAGCGTGCGCGCCGACCTTACCCCA
++++++++++++++++++++++++++++++++++++++++++++++++++++++++++++++++++++++++++++++++++++   5270
TCGGGCCCAGCCTCCTCCCCTCCCTCGGAGTGGAGAGGTCGCGGAGCCGCGGTATGAGCGGTCGCACGCGCGGCTGGAATGGGGT
```

```
               PshAI
GGCGGCCTTGACGTTGGTCTTGTCGGCAGGAGACAGCACCATGGTGGTTCTCTCTGAGTCTGTGGGGACCAGAAGAGTAAGCAA
++++++++++++++++++++++++++++++++++++++++++++++++++++++++++++++++++++++++++++++++++++   5355
CCGCCGGAACTGCAACCAGAACAGCCGTCCTCTGTCGTGGTACCACCAAGAGAGACTCAGACACCCCTGGTCTTCTCATTCGTT
                                    Start Codon
```

```
TAGATGGCTCTGCCCTGACTTTTATGCCCAGCCCTGGCTCCTGCCCTCCCTGCTCCTGGGAGTAGATTGGCCAACCCTAGGGTGT
++++++++++++++++++++++++++++++++++++++++++++++++++++++++++++++++++++++++++++++++++++   5440
ATCTACCGAGACGGGACTGAAAATACGGGTCGGGACCGAGGACGGGAGGGACGAGGACCCTCATCTAACCGGTTGGGATCCCACA
                                                              Beta Globin Promoter 200bp
```

```
GGCTCCACAGGGTGAGGTCTAAGTGATGACAGCCGTACCTGTCCTTGGCTCTTCTGGCACTGGCTTAGGAGTTGGACTTCAAACC
++++++++++++++++++++++++++++++++++++++++++++++++++++++++++++++++++++++++++++++++++++   5525
CCGAGGTGTCCCACTCCAGATTCACTACTGTCGGCATGGACAGGAACCGAGAAGACCGTGACCGAATCCTCAACCTGAAGTTTGG
```

FIG. 9G

```
CTCAGCCCTCCCTCTAAGATATATCTCTTGGCCCGATACCATCAGTACAAATTGCTACTAAAAACATCCTCCTTTGCAAGTGTAT
++++++++++++++++++++++++++++++++++++++++++++++++++++++++++++++++++++++++++++++++++++
GAGTCGGGAGGGAGATTCTATATAGAGAACCGGGCTATGGTAGTCATGTTTAACGATGATTTTTGTAGGAGGAAACGTTCACATA
                          Beta Globin Promoter 200bp
```
5610

BstZ17I

```
TTACGTAgtataacctcaagcctcattcagacactagtgtcaccagtctcctcatataccctattgtatttctttcttcttgctggt
++++++++++++++++++++++++++++++++++++++++++++++++++++++++++++++++++++++++++++++++++++
AATGCATcatatggagttcggagtaagtctgtgatcacagtggtcagaggagtatatggataacataaaagaagaagaacgacca
   Bgr                       HS1
```
5695

```
ttagtcatgtttctgggagcttaggggcttattttatttttgtttttgtttttctaatcaacagagatggcaaaccccattattttt
++++++++++++++++++++++++++++++++++++++++++++++++++++++++++++++++++++++++++++++++++++
aatcagtacaaaagaccctcgaatccccgaataaaataaaacaaaacaaagattagttgtctctacccgtttgggtaataaaaa
                                   HS1
```
5780

```
ttctttagacttgggatggtgatagctgggcagcgtcagaaactgtgtgtggatatagataagagctcaggactatgctgagctg
++++++++++++++++++++++++++++++++++++++++++++++++++++++++++++++++++++++++++++++++++++
aagaaatctgaaccctaccactatcgaccgtcgcagtctttgacacacacctatatctattctcgagtcctgatacgactcgac
                                   HS1
```
5865

```
tgatgagggaggggcctagctaaaggcagtgagagtcagaatgctcctgctattgccttctcagtccccacgcttggttttctaca
++++++++++++++++++++++++++++++++++++++++++++++++++++++++++++++++++++++++++++++++++++
actactccctccccggatcgattttccgtcactctcagtcttacgaggacgataacggaagagtcaggggtgcgaaccaaagatgt
                                   HS1
```
5950

```
caagtagatacatagaaaaggctataggttagtgtttgagagtcctgcatgattagttgctcagaaatgcccgataaatatgtta
++++++++++++++++++++++++++++++++++++++++++++++++++++++++++++++++++++++++++++++++++++
gttcatctatgtatcttttccgatatccaatcacaaactctcaggacgtactaatcaacgagtctttacgggctatttatacaat
                                   HS1
```
6035

```
tgtgtgttatgtatatatatgttttatatatatatatatgtgtgtgtgtgtgtgtgtgtgttgtgtttacaaatatgtgatt
++++++++++++++++++++++++++++++++++++++++++++++++++++++++++++++++++++++++++++++++++++
acacacaatacatatatataaaaatatatatatatatacacacacacacacacacacacaacacaaatgttttatacactaa
                                   HS1
```
6120

XbaI

```
atcatcaaaaacgtgagggctaaagtgaccagataaccttgcaagtcctaggataccaggaaaGtCTAGAATATGTCACATTCTGTC
++++++++++++++++++++++++++++++++++++++++++++++++++++++++++++++++++++++++++++++++++++
tagtagttttgcactcccgatttcactggtctattgaacgttcaggatcctatggtcctttCaGATCTTATACAGTGTAAGACAG
                         HS1                                   HS2
```
6205

FIG. 9H

```
TCAGGCATCCATTTTCTTTATGATGCCGTTTGAGGTGGAGTTTTAGTCAGGTGGTCAGCTTCTCCTTTTTTTTGCCATCTGCCCT
++++++++++++++++++++++++++++++++++++++++++++++++++++++++++++++++++++++++++++++++++++
AGTCCGTAGGTAAAAGAAATACTACGGCAAACTCCACCTCAAAATCAGTCCACCAGTCGAAGAGGAAAAAAAACGGTAGACGGGA
                                                          HS3
```
6290

```
GTAAGCATCCTGCTGGGGACCCAGATAGGAGTCATCACTCTAGGCTGAGAACATCTGGGCACACACCCTAAGCCTCAGCATGACT
++++++++++++++++++++++++++++++++++++++++++++++++++++++++++++++++++++++++++++++++++++
CATTCGTAGGACGACCCCTGGGTCTATCCTCAGTAGTGAGATCCGACTCTTGTAGACCCGTGTGTGGGATTCGGAGTCGTACTGA
                                                          HS3
```
6375

```
CATCATGACTCAGCATTGCTGTGCTTGAGCCAGAAGGTTTGCTTAGAAGGTTACACAGAACCAGAAGGCGGGGGTGGGGCACTGA
++++++++++++++++++++++++++++++++++++++++++++++++++++++++++++++++++++++++++++++++++++
GTAGTACTGAGTCGTAACGACACGAACTCGGTCTTCCAAACGAATCTTCCAATGTGTCTTGGTCTTCCGCCCCACCCCGTGACT
                                                          HS3
```
6460

```
CCCCGACAGGGGCCTGGCCAGAACTGCTCATGCTTGGACTATGGGAGGTCACTAATGGAGACACACAGAAATGTAACAGGAACTA
++++++++++++++++++++++++++++++++++++++++++++++++++++++++++++++++++++++++++++++++++++
GGGGCTGTCCCCGGACCGGTCTTGACGAGTACGAACCTGATACCCTCCAGTGATTACCTCTGTGTGTCTTTACATTGTCCTTGAT
                                                          HS3
```
6545

```
AGGAAAAACTGAAGCTTATTTAATCAGAGATGAGATGCTGGAAGGGATAGAGGGAGCTGAGCTTGTAAAAAGTATAGTAATCATT
++++++++++++++++++++++++++++++++++++++++++++++++++++++++++++++++++++++++++++++++++++
TCCTTTTTGACTTCGAATAAATTAGTCTCTACTCTACGACCTTCCCTATCTCCCTCGACTCGAACATTTTTCATATCATTAGTAA
                                                          HS3
```
6630

```
CAGCAAATGGTTTTGAAGCACCTGCTGGATGCTAAACACTATTTTCAGTGCTTGAATCATAAATAAGAATAAAACATGTATCTTA
++++++++++++++++++++++++++++++++++++++++++++++++++++++++++++++++++++++++++++++++++++
GTCGTTTACCAAAACTTCGTGGACGACCTACGATTTGTGATAAAAGTCACGAACTTAGTATTTATTCTTATTTTGTACATAGAAT
                                                          HS3
```
6715

```
TTCCCCACAAGAGTCCAAGTAAAAAATAACAGTTAATTATAATGTGCTCTGTCCGCCAGGCTGGAGTGCAGTGGCACGATCTCAG
++++++++++++++++++++++++++++++++++++++++++++++++++++++++++++++++++++++++++++++++++++
AAGGGGTGTTCTCAGGTTCATTTTTTATTGTCAATTAATATTACACGAGACAGGGGGTCCGACCTCACGTCACCGTGCTAGAGTC
                                                          HS3
```
6800

```
CTCACTGCAACCTCCGCCTCCCGGGCAGCTGGTTAGAAGGTTCTACTGGAGGAGGGTCCCAGCCCATTGCTAAATTAACATCAGG
++++++++++++++++++++++++++++++++++++++++++++++++++++++++++++++++++++++++++++++++++++
GAGTGACGTTGGAGGCGGAGGGCCCGTCGACCAATCTTCCAAGATGACCTCCTCCCAGGGTCGGGTAACGATTTAATTGTAGTCC
                                    HS3                           HS3
```
6885

```
CTCTGAGACTGGCAGTATATCTCTAACAGTGGTTGATGCTATCTTCTGGAACTTGCCTGCTACATTGAGACCACTGACCCATACA
++++++++++++++++++++++++++++++++++++++++++++++++++++++++++++++++++++++++++++++++++++
GAGACTCTGACCGTCATATAGAGATTGTCACCAACTACGATAGAAGACCTTGAACGGACGATGTAACTCTGGTGACTGGGTATGT
                                                          HS3
```
6970

FIG. 9I

FIG. 9J

```
tttattgctgaatgagagcctctgggacatcttgccagtcaatgagtctcaggttcaatttccttctcagtcttggagtaacag
++++++++++++++++++++++++++++++++++++++++++++++++++++++++++++++++++++++++++++++++++++++
aaataacgacttactctcggagacccctgtagaacggtcagttactcagagtccaagttaaaggaagagtcagaacctcattgtc
```
7820

```
aagctcatgcatttaataaacggaaatttgtattgaaatgagagccattggaaatcatttactccagactcctacttataaaaa
++++++++++++++++++++++++++++++++++++++++++++++++++++++++++++++++++++++++++++++++++++++
ttcgagtacgtaaattatttgcctttaaaacataactttactctcggtaacctttagtaaatgaggtctgaggatgaatatttt
```
7905

```
gagaaactgaggctcagagaagggtggggactttctcagtatgacatggaaatgatcaggcttggattcaaagctcctgactttc
++++++++++++++++++++++++++++++++++++++++++++++++++++++++++++++++++++++++++++++++++++++
ctctttgactccgagtctcttccccaccctgaaagagtcatactgtacctttactagtccgaacctaagtttcgaggactgaaag
```
7990

```
tgtctagtgtatgtgcagtgagccccttttcctctaactgaaagaaggaaaaaaaaatggaacccaaaatatatctacatagtttc
++++++++++++++++++++++++++++++++++++++++++++++++++++++++++++++++++++++++++++++++++++++
acagatcacatacacgtcactcggggaaaaggagattgacttcttccttttttttttaccttgggttttataagatgtatcaaag
```
8075

```
catgtcacagccagggctgggcagtctcctgttattctttaaaataaatatatcatttaaatgcataaataagcaaaccctgc
++++++++++++++++++++++++++++++++++++++++++++++++++++++++++++++++++++++++++++++++++++
gtacagtgtcggtcccgacccgtcagaggacaataaagaaaattttatttatatagtaaattacgtatttattcgtttgggacg
```
8160

```
tcgggaatgggagggagagtctctggagtccaccccttctcggccctggctctgcagatagtgctatcaaagcctgacagagcc
++++++++++++++++++++++++++++++++++++++++++++++++++++++++++++++++++++++++++++++++++++++
agcccttaccctccctctcagagacctcaggtggggaagagccgggaccgagacgtctatcacgatagtttcgggactgtctcgg
```
8245

```
ctgcccattgctgggccttggagtgagtcagcctagtagagaggcagggcaagccatctcatagctgctgagtgggagagagaaa
++++++++++++++++++++++++++++++++++++++++++++++++++++++++++++++++++++++++++++++++++++++
gacgggtaacgacccggaacctcactcagtcggatcatctctccgtcccgttcggtagagtatcgacgactcaccctctctcttt
```
8330

```
agggctcattgtctataaactcaggtcatggctattcttattctcacactaagaaaaagaatgagatgtctacatataccctgcg
++++++++++++++++++++++++++++++++++++++++++++++++++++++++++++++++++++++++++++++++++++++
tcccgagtaacagatatttgagtccagtaccgataagaataagagtgtgattcttttctactctacagatgtatatgggacgc
```
8415

```
tcccctcttgtgtactggggtccccaagagctctctaaaagtgatggcaaagtcattgcgctagatgccatcccatctattataa
++++++++++++++++++++++++++++++++++++++++++++++++++++++++++++++++++++++++++++++++++++++
agggagaacacatgaccccagggttctcgagagattttcactaccgtttcagtaacgcgatctacggtagggtagataatatt
```
8500

FIG. 9K

FIG. 9L

```
                                                                    NheI    BmtI
tgtgcccgtctgttgtgtgactctggtaactagagatccctcagaccctttttagtcagtgtggaaaatctctagcagGCTAGCaa
++++++++++++++++++++++++++++++++++++++++++++++++++++++++++++++++++++++++++++++++++++++  9350
acacgggcagacaacacactgagaccattgatctctagggagtctgggaaaatcagtcacaccttttagagatcgtcCGATCGtt
                          HIV-1 LTR
```

```
    BsiWI            PacI        SalI
acaaaagaCGTACGagctatgctTTAATTAAagctatgctGTCGACaatcaacctctggattacaaaatttgtgaaagattgact
++++++++++++++++++++++++++++++++++++++++++++++++++++++++++++++++++++++++++++++++++++++  9435
tgttttctGCATGCtcgatacgaAATTAATTtcgatacgaCAGCTGttagttggagacctaatgttttaaacacttttctaactga
                                                      WPRE
```

```
ggtattcttaactatgttgctccttttacgctatgtggatacgctgctttaatgcctttgtatcatgctattgcttcccgtatgg
++++++++++++++++++++++++++++++++++++++++++++++++++++++++++++++++++++++++++++++++++++++  9520
ccataagaattgatacaacgaggaaaatgcgatacaccctatgcgacgaaattacggaaacatagtacgataacgaagggcatacc
                                        WPRE
```

```
ctttcatttctcctccttgtataaatcctggttgctgtctctttatgaggagttgtggcccgttgtcaggcaacgtggcgtggt
++++++++++++++++++++++++++++++++++++++++++++++++++++++++++++++++++++++++++++++++++++++  9605
gaaagtaaaagaggaggaacatatttaggaccaacgacagagaaatactcctcaacaccgggcaacagtccgttgcaccgcacca
                                        WPRE
```

```
                      PflMI
gtgcactgtgtttgctgacgcaaccccactgttggggcattgccaccacctgtcagctcctttccgggactttcgctttcccc
++++++++++++++++++++++++++++++++++++++++++++++++++++++++++++++++++++++++++++++++++++++  9690
cacgtgacacaaacgactgcgttgggggtgaccaaccccgtaacggtggtggacagtcgaggaaaggccctgaaagcgaaagggg
                                        WPRE
```

```
ctccctattgccacggcggaactcatcgccgcctgccttgcccgctgctggacaggggctcggctgttgggcactgacaattccg
++++++++++++++++++++++++++++++++++++++++++++++++++++++++++++++++++++++++++++++++++++++  9775
gagggataacggtgccgccttgagtagcggcggacggaacgggcgacgacctgtccccgagccgacaacccgtgactgttaaggc
                                        WPRE
```

```
tggtgttgtcggggaagctgacgtcctttccatggctgctcgcctgtgttgccacctggattctgcgcgggacgtccttctgcta
++++++++++++++++++++++++++++++++++++++++++++++++++++++++++++++++++++++++++++++++++++++  9860
accacaacagcccctcgactgcaggaaaggtaccgacgagcggacacaacggtggacctaagacgcgccctgcaggaagacgat
                                        WPRE
```

```
cgtccctttcggccctcaatccagcggaccttcctttcccgcggcctgctgccggctctgcggcctcttccgcgtcttcgccttcgc
++++++++++++++++++++++++++++++++++++++++++++++++++++++++++++++++++++++++++++++++++++++  9945
gcagggaagccggggagttaggtcgcctggaaggaaggggcgccggacgacggccgagacgccggagaagcgcagaagcggaagcg
                                        WPRE
```

FactorXa site

FIG. 9M

EcoRI cctcagacgagtcggatctcccttttgggccgcctccccgcctggaattcgagctcGGTACCTGATCAGCCTCGACTGTGCCTTCT
ggagtctgctcagcctagagggaaaccggcggagggcggaccttaagctcgagCCATGGACTAGTCGGAGCTGACACGGAAGA

WPRE ⟶      BGH PA ⟩    10,030

AGTTGCCAGCCATCTGTTGTTTGCCCCTCCCCCGTGCCTTCCTTGACCCTGGAAGGTGCCACTCCCACTGTCCTTTCCTAATAAA
TCAACGGTCGGTAGACAACAAACGGGGAGGGGCACGGAAGGAACTGGGACCTTCCACGGTGAGGGTGACAGGAAAGGATTATTT

BGH PA    10,115

ATGAGGAAATTGCATCGCATTGTCTGAGTAGGTGTCATTCTATTCTGGGGGGTGGGGTGGGGCAGGACAGCAAGGGGGAGGATTG
TACTCCTTTAACGTAGCGTAACAGACTCATCCACAGTAAGATAAGACCCCCCACCCCACCCCGTCCTGTCGTTCCCGCTCCTAAC

BGH PA    10,200

GGAAGACAATAGCAGGCATGCTGGGGATGCGGTGGGCTCTATGGCTTCTGAGGAAAGAACCAGCTGGGGCTCGAGATCCACTAGT
CCTTCTGTTATCGTCCGTACGACCCCTACGCCACCCGAGATACCGAAGACTCCTTTCTTGGTCGACCCCGAGCTCTAGGTGATCA

BGH PA    10,285

AbsI
PspXI

TCTAGCCTCGAGGCTAGAGCGGCCGCCACCGCGGtagtagttcatgtcatcttattattcagtatttataacttgcaaagaaatg
AGATCGGAGCTCCGATCTCGCCGGCGGTGGCGCCatcatcaagtacagtagaataataagtcataaatattgaacgtttctttac 10,370 aatatcagagagtgagaggaacttgttttattgcagcttataatggttacaaataaagcaatagcatcacaaatttcacaaataaa
ttatagtctctcactctccttgaacaaataacgtcgaatattaccaatgtttatttcgttatcgtagtgtttaaagtgtttattt 10,455 gcattttttttcactgcattctagttgtggtttgtccaaactcatcaatgtatcttatcatgtctggctctagctatccgccct
cgtaaaaaaagtgacgtaagatcaacaccaaacaggtttgagtagttacatagaatagtacagaccgagatcgataggcgggga SV40 ori ⟩    10,540 aactccgcccagttccgcccattctccgccccatggctgactaatttttttatttatgcagaggccgaggccgcctcggcctct
ttgaggcgggtcaaggcgggtaagaggcgggtaccgactgattaaaaaaataaatacgtctccggctccggcggagccggaga SV40 ori    10,625

FIG. 9N

BsmBI gagctattccagaagtagtgaggaggctttttggAGGCCTaggcttttgcgtcgagacgtacccaattcgccctatagtgagtc 10,710
ctcgataaggtcttcatcactcctccgaaaaaaccTCCGGAtccgaaaacgcagctctgcatgggttaagcgggatatcactcag gtattacgcgcgctcactggccgtcgttttacaacgtcgtgactgggaaaaccctggcgttacccaacttaatcgccttgcagca 10,795
cataatgcgcgcgagtgaccggcagcaaaatgttgcagcactgacccttttgggaccgcaatggttgaattagcggaacgtcgt catcccctttcgccagctggcgtaatagcgaagaggcccgcaccgatcgcccttcccaacagttgcgcagcctgaatggcgaat 10,880
gtaggggaaagcggtcgaccgcattatgcttctccggcgtggctagcgggaagggttgtcaacgcgtcggacttaccgctta ggcgcgacgcgccctgtagcggcgcattaagcgcggcgggtgtggtggttacgcgcagcgtgaccgctacacttgccagcgccct 10,965
ccgcgctgcgcggacatcgccgcgtaattcgcgccgcccacaccaccaatgcgcgtcgcactggcgatgtgaacggtcgcggga LacZ alpha agcgcccgctcctttcgctttcttcccttcctttctcgccacgttcgccggcttcccgtcaagctctaaatcggggctcct 11,050
tcgcgggcgaggaaagcgaaagaaggaaggaaagagcggtgcaagcggccgaaaggggcagttcgagatttagccccgaggga ttagggttccgatttagtgctttacggcacctcgaccccaaaaaacttgattagggtgatggttcacgtagtgggccatcgcct 11,135
aatcccaaggctaaatcacgaaatgccgtggagctgggttttttgaactaatcccactaccaagtgcatcacccggtagcggga gatagacggtttttcgcctttgacgttggagtccacgttctttaatagtggactcttgttccaaactggaacaacactcaacc 11,220
ctatctgccaaaaagcgggaaactgcaacctcaggtgcaagaaattatcacctgagaacaaggtttgaccttgttgtgagttggg

FIG. 9O

FIG. 9P

```
ATACCAAACGACGAGCGTGACACCACGATGCCTGTAGCAATGGCAACAACGTTGCGCAAACTATTAACTGGCGAACTACTTACTC
++++++++++++++++++++++++++++++++++++++++++++++++++++++++++++++++++++++++++++++++++++    12,070
TATGGTTTGCTGCTCGCACTGTGGTGCTACGGACATCGTTACCGTTGTTGCAACGCGTTTGATAATTGACCGCTTGATGAATGAG
                                        AmpR                                        >
```

```
TAGCTTCCCGGCAACAATTAATAGACTGGATGGAGGCGGATAAAGTTGCAGGACCACTTCTGCGCTCGGCCCTTCCGGCTGGCTG
++++++++++++++++++++++++++++++++++++++++++++++++++++++++++++++++++++++++++++++++++++    12,155
ATCGAAGGGCCGTTGTTAATTATCTGACCTACCTCCGCCTATTTCAACGTCCTGGTGAAGACGCGAGCCGGGAAGGCCGACCGAC
                                        AmpR                                        >
```

```
GTTTATTGCTGATAAATCTGGAGCCGGTGAGCGTGGGTCTCGCGGTATCATTGCAGCACTGGGGCCAGATGGTAAGCCCTCCCGT
++++++++++++++++++++++++++++++++++++++++++++++++++++++++++++++++++++++++++++++++++++    12,240
CAAATAACGACTATTTAGACCTCGGCCACTCGCACCCAGAGCGCCATAGTAACGTCGTGACCCCGGTCTACCATTCGGGAGGGCA
                                        AmpR                                        >
```

```
ATCGTAGTTATCTACACgacggggagtcaggcaactatggatgaacgaaatagacagatcgctgagataggtgcctcactgatta
++++++++++++++++++++++++++++++++++++++++++++++++++++++++++++++++++++++++++++++++++++    12,325
TAGCATCAATAGATGTGctgccctcagtccgttgatacctacttgctttatctgtctagcgactctatccacggagtgactaat
                                        AmpR                                        >
```

```
agcattggtaa  3'
++++++++++ ... 12,336
tcgtaaccatt 5'
▶
AmpR
```

FIG. 9Q

```
                            SEQUENCE LISTING

<160> NUMBER OF SEQ ID NOS: 2

<210> SEQ ID NO 1
<211> LENGTH: 12336
<212> TYPE: DNA
<213> ORGANISM: Artificial Sequence
<220> FEATURE:
<223> OTHER INFORMATION: ALS20 alpha

<400> SEQUENCE: 1
ctgtcagacc aagtttactc atatatactt tagattgatt taaaacttca tttttaattt      60
aaaaggatct aggtgaagat cctttttgat aatctcatga ccaaaatccc ttaacgtgag     120
ttttcgttcc actgagcgtc agaccccgta gaaaagatca aaggatcttc ttgagatcct     180 tttttctgc gcgtaatctg ctgcttgcaa acaaaaaaac caccgctacc agcggtggtt      240
tgtttgccgg atcaagagct accaactctt tttccgaagg taactggctt cagcagagcg     300
cagataccaa atactgtcct tctagtgtag ccgtagttag gccaccactt caagaactct     360
gtagcaccgc ctacatacct cgctctgcta atcctgttac cagtggctgc tgccagtggc     420
gataagtcgt gtcttaccgg gttggactca agacgatagt taccggataa ggcgcagcgg     480
tcgggctgaa cggggggttc gtgcacacag cccagcttgg agcgaacgac ctacaccgaa     540
ctgagatacc tacagcgtga gctatgagaa agcgccacgc ttcccgaagg gagaaaggcg     600
gacaggtatc cggtaagcgg cagggtcgga acaggagagc gcacgaggga gcttccaggg     660
ggaaacgcct ggtatcttta tagtcctgtc gggtttcgcc acctctgact tgagcgtcga     720
tttttgtgat gctcgtcagg ggcggagc ctatggaaaa acgccagcaa cgcggccttt      780
ttacggttcc tggccttttg ctggcctttt gctcacatgt tctttcctgc gttatcccct     840
gattctgtgg ataaccgtat taccgccttt gagtgagctg ataccgctcg ccgcagccga     900
acgaccgagc gcagcgagtc agtgagcgag gaagcggaag agcgcccaat acgcaaaccg     960
cctctccccg cgcgttggcc gattcattaa tgcagctggc acgacaggtt tcccgactgg    1020
aaagcgggca gtgagcgcaa cgcaattaat gtgagttagc tcactcatta ggcaccccag    1080
gctttacact ttatgcttcc ggctcgtatg ttgtgtggaa ttgtgagcgg ataacaattt    1140
cacacaggaa acagctatga ccatgattac gccaagcgcg caattaaccc tcactaaagg    1200
gaacaaaagc tggagctgca agcttggcca ttgcatacgt tgtatccata tcataatatg    1260
tacatttata ttggctcatg tccaacatta ccgccatgtt gacattgatt attgactagt    1320
tattaatagt aatcaattac ggggtcatta gttcatagcc catatatgga gttccgcgtt    1380
acataactta cggtaaatgg cccgcctggc tgaccgccca acgaccccgc cccattgacg    1440
tcaataatga cgtatgttcc catagtaacg ccaatagga ctttccattg acgtcaatgg     1500
```

-continued

```
gtggagtatt tacggtaaac tgcccacttg gcagtacatc aagtgtatca tatgccaagt     1560
acgcccccta ttgacgtcaa tgacggtaaa tggcccgcct ggcattatgc ccagtacatg     1620
accttatggg actttcctac ttggcagtac atctacgtat tagtcatcgc tattaccatg     1680
gtgatgcggt tttggcagta catcaatggg cgtggatagc ggtttgactc acggggattt     1740
ccaagtctcc accccattga cgtcaatggg agtttgtttt ggcaccaaaa tcaacgggac     1800
tttccaaaat gtcgtaacaa ctccgcccca ttgacgcaaa tgggcggtag gcgtgtacgg     1860
tgggaggtct atataagcag agctcgttta gtgaaccggg gtctctctgg ttagaccaga     1920
tctgagcctg ggagctctct ggctaactag ggaacccact gcttaagcct caataaagct     1980
tgccttgagt gcttcaagta gtgtgtgccc gtctgttgtg tgactctggt aactagagat     2040
ccctcagacc cttttagtca gtgtggaaaa tctctagcag tggcgcccga acagggacct     2100
gaaagcgaaa gggaaaccag agctctctcg acgcaggact cggcttgctg aagcgcgcac     2160
ggcaagaggc gaggggcggc gactggtgag tacgccaaaa attttgacta gcggaggcta     2220
gaaggagaga gatgggtgcg agagcgtcag tattaagcgg gggagaatta gatcgcgatg     2280
ggaaaaaatt cggttaaggc cagggggaaa gaaaaaatat aaattaaaac atatagtatg     2340
ggcaagcagg gagctagaac gattcgcagt taatcctggc ctgttagaaa catcagaagg     2400
ctgtagacaa atactgggac agctacaacc atcccttcag acaggatcag aagaacttag     2460
atcattatat aatacagtag caaccctcta ttgtgtgcat caaaggatag agataaaaga     2520
caccaaggaa gctttagaca agatagagga agagcaaaac aaaagtaaga ccaccgcaca     2580
gcaagcggcc gctgatcttc agacctggag gaggagatat gagggacaat ggagaagtg     2640 aattatataa atataaagta gtaaaaattg aaccattagg agtagcaccc accaaggcaa     2700
agagaagagt ggtgcagaga gaaaaaagag cagtgggaat aggagctttg ttccttgggt     2760
tcttgggagc agcaggaagc actatgggcg cagcctcaat gacgctgacg gtacaggcca     2820
gacaattatt gtctggtata gtgcagcagc agaacaattt gctgagggct attgaggcgc     2880
aacagcatct gttgcaactc acagtctggg gcatcaagca gctccaggca agaatcctgg     2940
ctgtggaaag atacctaaag gatcaacagc tcctggggat ttggggttgc tctggaaaac     3000
tcatttgcac cactgctgtg ccttggaatg ctagttggag taataaatct ctggaacaga     3060
tttggaatca cacgacctgg atggagtggg acagagaaat taacaattac acaagcttaa     3120
tacactcctt aattgaagaa tcgcaaaacc agcaagaaaa gaatgaacaa gaattattgg     3180
aattagataa atgggcaagt ttgtggaatt ggtttaacat aacaaattgg ctgtggtata     3240
taaaattatt cataatgata gtaggaggct tggtaggttt aagaatagtt tttgctgtac     3300
tttctatagt gaatagagtt aggcaggat attcaccatt atcgtttcag acccacctcc     3360
caaccccgag gggacccgac aggcccgaag gaatagaaga agaaggtgga gagagagaca     3420
gagacagatc cattcgatta gtgaacggat ctcgacggta tcggttaact tttaaaagaa     3480
aaggggggat tggggggtac agtgcagggg aagaatagt agacataata gcaacagaca     3540
tacaaactaa agaattacaa aaacaaatta caaaaattca aaattttatc gataagcttg     3600
ggagttccgc gtgttggggg tggaccatcc tctaggtatt gaataagaaa aatgaagtta     3660
aggtggttga tggtaacact atgctaataa ctgcagagcc agaagcacca taagggacat     3720
gataagggag ccagcagacc tctgatctct tcctgaatgc taatcttaaa catcctgagg     3780
aagaatggga cttccatttg gggtgggcct atgatagggt aataagacag tagtgaatat     3840
caagctacaa aaagccccct ttcaaattct tctcagtcct aacttttcat actaagccca     3900
```

```
gtccttccaa agcagactgt gaaagagtga tagttccggg agactagcac tgcagattcc    3960
gggtcactgt gagtgggggga ggcagggaag aagggctcac aggacagtca aaccatgccc    4020 cctgttttc cttcttcaag tagacctcta taagacaaca gagacaacta aggctgagtg    4080
gccaggcgag gagaaaccat ctcgccgtaa aacatggaag gaacacttca ggggaaaggt    4140
ggtatctcta agcaagagaa ctgagtggag tcaaggctga gagatgcagg ataagcaaat    4200
gggtagtgaa aagacattca tgaggacagc taaaacaata agtaatgtaa aatacagcat    4260
agcaaaactt taacctccaa atcaagcctc tacttgaatc cttttctgag ggatgaataa    4320
ggcataggca tcaggggctg ttgccaatgt gcattagctg tttgcagcct caccttcttt    4380
catggagttt aagatatagt gtattttccc aaggtttgaa ctagctcttc atttctttat    4440
gttttaaatg cactgacctc ccacattccc ttttagtaa aatattcaga aataatttaa    4500
atacatcaag cgcttgctgc ccactcagac tttattcaaa gaccaggaag ggccggtgca    4560
aggaggggag gagggcccgt tgggaggccc agcgggcagg aggaacggct accgaggctc    4620
cagcttaacg gtatttggag gtcagcacgg tgctcacaga agccaggaac ttgtccaggg    4680
aggcgtgcac cgcaggggtg aactcggcgg ggaggtgggc ggccagggtc accagcaggc    4740
agtggcttag gagctgtgca gagaagaggg tcagtgcggc ccaggcccgc agccgccgcc    4800
tgcgctacac ctcccgcaac ccgcgtgatc ctctgccctg agaggaaggc gccatctcgc    4860
ccctcgaccc agatcgctcc cggcccgccg ctcaccttga agttgaccgg gtccacccga    4920
agcttgtgcg cgtgcaggtc gctcaggcg gacagcgcgt tgggcatgtc gtccacgtgc    4980
gccacggcgt tggtcagcgc gtcggccacc ttcttgccgt ggcccttaac ctgggcagag    5040
ccgtggctca ggtcgaagtg cgggaagtag gtcttggtgg tggggaagga caggaacatc    5100
ctgcggggag aagcagagtg aggggtgggg tttgggtccg gggccaggac ggttgagggt    5160
ggcctgtggg tccgggcggg cgaggagccc gggtcggagc aggggaggga gcctcacctc    5220
tccagggcct ccgcaccata ctcgccagcg tgcgcgccga ccttaccca gcggccttg    5280 acgttggtct tgtcggcagg agacagcacc atggtgggtt ctctctgagt ctgtggggac    5340
cagaagagta agcaatagat ggctctgccc tgactttat gcccagccct ggctcctgcc    5400
ctccctgctc ctgggagtag attggccaac cctagggtgt ggctccacag ggtgaggtct    5460
aagtgatgac agccgtacct gtccttggct cttctggcac tggcttagga gttggacttc    5520
aaaccctcag ccctccctct aagatatatc tcttggcccc ataccatcag tacaaattgc    5580
tactaaaaac atcctccttt gcaagtgtat ttacgtagta tacctcaagc ctcattcaga    5640
cactagtgtc accagtctcc tcatatacct attgtatttt cttcttcttg ctggtttagt    5700 catgtttct gggagcttag gggcttattt tattttgttt tgttttctaa tcaacagaga    5760
tgggcaaacc cattatttt ttcttagac ttgggatggt gatagctggg cagcgtcaga    5820
aactgtgtgt ggatatagat aagagctcag gactatgctg agctgtgatg agggaggggc    5880
ctagctaaag gcagtgagag tcagaatgct cctgctattg ccttctcagt ccccacgctt    5940
ggtttctaca caagtagata catagaaaag gctataggtt agtgtttgag agtcctgcat    6000
gattagttgc tcagaaatgc ccgataaata tgttatgtgt gtttatgtat atatatgttt    6060
tatatatata tatatgtgtg tgtgtgtgtg tgtgtgtgtt gtgtttacaa atatgtgatt    6120
atcatcaaaa cgtgagggct aaagtgacca gataacttgc aagtcctagg ataccaggaa    6180
agtctagaat atgtcacatt ctgtctcagg catccatttt ctttatgatg ccgtttgagg    6240
```

-continued

```
tggagtttta gtcaggtggt cagcttctcc ttttttttgc catctgccct gtaagcatcc    6300
tgctggggac ccagatagga gtcatcactc taggctgaga acatctgggc acacaccctc    6360
agcctcagca tgactcatca tgactcagca ttgctgtgct tgagccagaa ggtttgctta    6420
gaaggttaca cagaaccaga aggcggggt ggggcactga ccccgacagg ggcctggcca     6480
gaactgctca tgcttggact atgggaggtc actaatggag acacacagaa atgtaacagg    6540
aactaaggaa aaactgaagc ttatttaatc agagatgaga tgctggaagg gatagaggga    6600
gctgagcttg taaaaagtat agtaatcatt cagcaaatgg ttttgaagca cctgctggat    6660
gctaaacact atttcagtg cttgaatcat aaataagaat aaaacatgta tcttattccc     6720
cacaagagtc caagtaaaaa ataacagtta attataatgt gctctgtccc ccaggctgga    6780
gtgcagtggc acgatctcag ctcactgcaa cctccgcctc ccgggcagct ggttagaagg    6840
ttctactgga ggagggtccc agcccattgc taaattaaca tcaggctctg agactggcag    6900
tatatctcta acagtggttg atgctatctt ctggaacttg cctgctacat tgagaccact    6960
gacccataca taggaagccc atagctctgt cctgaactgt taggccactg gtccagagag    7020
tgtgcatctc ctttgatcct cataataacc ctatgagata dacacaatta ttactcttac    7080
tttatagatg atgatcctga aaacatagga gtcaaggcac ttgcccctag ctgggggtat    7140
aggggagcag tcccatgtag tagtagaatg aaaaatgctg ctatgctgtg cctccccac    7200 cttcccatg tctgccctct actcatggtc tatctctcct ggctcctggg agtcatggac     7260
tccacccagc accaccaacc tgacctaacc acctatctga gcctgccagc ctataaccca    7320
tctgggccct gatagctggt ggccagccct gaccccaccc caccctccct ggaacctctg    7380
atagacacat ctggcacacc agctcgcaaa gtcaccgtga gggtcttgtg tttgctgagt    7440
caaaattcct tgaaatccaa gtccttagag actcctgctc ccaaatttac agtcatagac    7500
ttcttcatgg ctgtctcctt tatccacaga atgattcctt tgcttcattg ccccatccat    7560
ctgatcctcc tcatcagtgc agcacagggc ccatgagcag tagctgcaga gtctcacata    7620
ggtctggcac tgcctctgac atgtccgacc ttaggcaaat gcttgactct tctgagctca    7680
ccggtactag tgcatgcaaa tctgacactc agtgggcctg ggtgaaggtg agaattttat    7740
tgctgaatga gagcctctgg ggacatcttg ccagtcaatg agtctcaggt tcaatttcct    7800
tctcagtctt ggagtaacag aagctcatgc atttaataaa cggaaatttt gtattgaaat    7860
gagagccatt ggaaatcatt tactccagac tcctacttat aaaaagagaa actgaggctc    7920
agagaagggt ggggactttc tcagtatgac atggaaatga tcaggcttgg attcaaagct    7980
cctgactttc tgtctagtgt atgtgcagtg agccccttt cctctaactg aaagaaggaa     8040
aaaaaaatgg aacccaaaat attctacata gtttccatgt cacagccagg gctgggcagt    8100
ctcctgttat ttcttttaaa ataaatatat catttaaatg cataaataag caaaccctgc    8160 tcggaatgg gagggagagt ctctggagtc caccccttct cggccctggc tctgcagata     8220
gtgctatcaa agccctgaca gagccctgcc cattgctggg ccttggagtg agtcagccta    8280
gtagagaggc agggcaagcc atctcatagc tgctgagtgg gagagagaaa agggctcatt    8340
gtctataaac tcaggtcatg gctattctta ttctcacact aagaaaaaga atgagatgtc    8400
tacatatacc ctgcgtcccc tcttgtgtac tggggtcccc aagagctctc taaaagtgat    8460
ggcaaagtca ttgcgctaga tgccatccca tctattataa acctgcattt gtctccacac    8520
accagtcatg gacaataacc ctcctcccag gtccacgtgc ttgtctttgt ataatactca    8580
agtaatttcg gaaaatgtat tctttcaatc ttgttctgtt attcctgttt caatggctta    8640
```

```
gtagaaaaag tacatacttg ttttcccata aattgacaat agacaatttc acatcaatgt    8700
ctatatgggt cgttgtgttt gctgtgtttg caaaaactca caataacttt atattgttac    8760
tactctaaga aagttacaac atggtgaata caagagaaag ctattacaag tccagaaaat    8820
aaaagttatc atcttgaggc ctcctgcagg gtacctttaa gaccaatgac ttacaaggca    8880
gctgtagatc ttagccactt tttaaaagaa aaggggggac tggaagggct aattcactcc    8940
caacgaagac aagatctgct ttttgctgtg cgggccaggc ccccgagggc cttatcggcc    9000
ccagaggcgc ttgctgtcgg gccgggcgct cccggcacgg gcgggcggag gggtggcgcc    9060
cgcctgggga ccgcagatta caagagcacc tcctccccca accccaggag gccccgctcc    9120
ccaggcctcg gccggcgcgg acccctggtt gccccggact gggtctctct ggttagacca    9180
gatctgagcc tgggagctct ctggctaact agggaaccca ctgcttaagc ctcaataaag    9240
cttgccttga gtgcttcaag tagtgtgtgc ccgtctgttg tgtgactctg gtaactagag    9300
atccctcaga ccctttagt cagtgtggaa aatctctagc aggctagcaa acaaaagacg    9360
tacgagctat gctttaatta aagctatgct gtcgacaatc aacctctgga ttacaaaatt    9420
tgtgaaagat tgactggtat tcttaactat gttgctcctt ttacgctatg tggatacgct    9480
gctttaatgc ctttgtatca tgctattgct tcccgtatgg ctttcatttt ctcctccttg    9540
tataaatcct ggttgctgtc tctttatgag gagttgtggc ccgttgtcag caacgtggc    9600
gtggtgtgca ctgtgtttgc tgacgcaacc cccactggtt ggggcattgc caccacctgt    9660
cagctccttt ccgggacttt cgcttccc ctccctattg ccacggcgga actcatcgcc    9720
gcctgccttg cccgctgctg gacaggggct cggctgttgg gcactgacaa ttccgtggtg    9780
ttgtcgggga agctgacgtc ctttccatgg ctgctcgcct gtgttgccac ctggattctg    9840
cgcgggacgt ccttctgcta cgtccccttcg gccctcaatc cagcggacct tccttcccgc    9900
ggcctgctgc cggctctgcg gcctcttccg cgtcttcgcc ttcgccctca gacgagtcgg    9960
atctcccttt gggccgcctc cccgcctgga attcgagctc ggtacctgat cagcctcgac   10020
tgtgccttct agttgccagc catctgttgt ttgcccctcc ccgtgccttt ccttgaccct   10080
ggaaggtgcc actcccactg tcctttccta ataaaatgag gaaattgcat cgcattgtct   10140
gagtaggtgt cattctattc tggggggtgg ggtggggcag gacagcaagg gggaggattg   10200
ggaagacaat agcaggcatg ctggggatgc ggtgggctct atggcttctg aggaaagaac   10260
cagctggggc tcgagatcca ctagttctag cctcgaggct agagcggccg ccaccgcggt   10320
agtagttcat gtcatcttat tattcagtat ttataacttg caaagaaatg aatatcagag   10380
agtgagagga acttgtttat tgcagcttat aatggttaca aataaagcaa tagcatcaca   10440
aatttcacaa ataaagcatt ttttcactg cattctagtt gtggtttgtc caaactcatc   10500
aatgtatctt atcatgtctg gctctagcta tcccgcccct aactccgccc agttccgccc   10560
attctccgcc ccatggctga ctaatttttt ttatttatgc agaggccgag gccgcctcgg   10620
cctctgagct attccagaag tagtgaggag gcttttttgg aggcctaggc ttttgcgtcg   10680
agacgtaccc aattcgccct atagtgagtc gtattacgcg cgctcactgg ccgtcgtttt   10740
acaacgtcgt gactgggaaa accctggcgt taccaactt aatcgccttg cagcacatcc   10800
cccttttcgcc agctggcgta atagcgaaga ggcccgcacc gatcgccctt cccaacagtt   10860
gcgcagcctg aatggcgaat ggcgcgacgc gccctgtagc ggcgcattaa gcgcggcggg   10920
tgtggtggtt acgcgcagcg tgaccgctac acttgccagc gccctagcgc ccgctccttt   10980
```

```
cgctttcttc ccttcctttc tcgccacgtt cgccggcttt ccccgtcaag ctctaaatcg    11040
ggggctccct ttagggttcc gatttagtgc tttacggcac ctcgacccca aaaaacttga    11100
ttagggtgat ggttcacgta gtgggccatc gccctgatag acggttttc gccctttgac     11160
gttggagtcc acgttcttta atagtggact cttgttccaa actggaacaa cactcaaccc    11220
tatctcggtc tattcttttg atttataagg gattttgccg atttcggcct attggttaaa    11280
aaatgagctg atttaacaaa aatttaacgc gaattttaac aaaatattaa cgtttacaat    11340
ttcccaggtg gcacttttcg gggaaatgtg cgcggaaccc ctatttgttt attttttctaa   11400
atacattcaa atatgtatcc gctcatgaga caataaccct gataaatgct tcaataatat    11460
tgaaaaagga agagtatgag tattcaacat ttccgtgtcg cccttattcc cttttttgcg    11520
gcatttgcc ttcctgtttt tgctcaccca gaaacgctgg tgaaagtaaa agatgctgaa      11580
gatcagttgg gtgcacgagt gggttacatc gaactggatc tcaacagcgg taagatcctt    11640
gagagttttc gccccgaaga acgttttcca atgatgagca cttttaaagt tctgctatgt    11700
ggcgcggtat tatcccgtat tgacgccggg caagagcaac tcggtcgccg catacactat    11760
tctcagaatg acttggttga gtactcacca gtcacagaaa agcatcttac ggatggcatg    11820
acagtaagag aattatgcag tgctgccata accatgagtg ataacactgc ggccaactta    11880
cttctgacaa cgatcggagg accgaaggag ctaaccgctt ttttgcacaa catgggggat    11940
catgtaactc gccttgatcg ttgggaaccg gagctgaatg aagccatacc aaacgacgag    12000
cgtgacacca cgatgcctgt agcaatggca acaacgttgc gcaaactatt aactggcgaa    12060
ctacttactc tagcttcccg gcaacaatta atagactgga tggaggcgga taaagttgca    12120
ggaccacttc tgcgctcggc ccttccggct ggctggttta ttgctgataa atctggagcc    12180
ggtgagcgtg gtctcgcgg tatcattgca gcactgggc cagatggtaa gccctcccgt       12240
atcgtagtta tctacacgac ggggagtcag gcaactatgg atgaacgaaa tagacagatc    12300
gctgagatag gtgcctcact gattaagcat tggtaa                               12336
```

<210> SEQ ID NO 2
<211> LENGTH: 12336
<212> TYPE: DNA
<213> ORGANISM: Artificial Sequence
<220> FEATURE:
<223> OTHER INFORMATION: codon optimized ALS20 alpha

<400> SEQUENCE: 2

```
ctgtcagacc aagtttactc atatatactt tagattgatt taaaacttca tttttaattt      60
aaaaggatct aggtgaagat cctttttgat aatctcatga ccaaaatccc ttaacgtgag     120
ttttcgttcc actgagcgtc agaccccgta gaaaagatca aggatcttc ttgagatcct      180
ttttttctgc gcgtaatctg ctgcttgcaa acaaaaaaac caccgctacc agcggtggtt     240
tgtttgccgg atcaagagct accaactctt tttccgaagg taactggctt cagcagagcg     300
cagataccaa atactgtcct tctagtgtag ccgtagttag gccaccactt caagaactct     360
gtagcaccgc ctacataccct cgctctgcta atcctgttac cagtggctgc tgccagtggc    420
gataagtcgt gtcttaccgg gttggactca agacgatagt taccggataa ggcgcagcgg    480
tcgggctgaa cggggggttc gtgcacacag cccagcttgg agcgaacgac ctacaccgaa    540
ctgagatacc tacagcgtga gctatgagaa agcgccacgc ttcccgaagg gagaaaggcg    600
gacaggtatc cggtaagcgg cagggtcgga acaggagagc gcacgaggga gcttccaggg    660
ggaaacgcct ggtatcttta tagtcctgtc gggtttcgcc acctctgact tgagcgtcga    720
```

```
tttttgtgat gctcgtcagg ggggcggagc ctatggaaaa acgccagcaa cgcggccttt     780
ttacggttcc tggcctttg ctggccttt gctcacatgt tctttcctgc gttatccct       840 gattctgtgg ataaccgtat taccgccttt gagtgagctg ataccgctcg ccgcagccga    900
acgaccgagc gcagcgagtc agtgagcgag gaagcggaag agcgcccaat acgcaaaccg    960
cctctccccg cgcgttggcc gattcattaa tgcagctggc acgacaggtt cccgactgg    1020 aaagcgggca gtgagcgcaa cgcaattaat gtgagttagc tcactcatta ggcaccccag   1080
gctttacact ttatgcttcc ggctcgtatg ttgtgtggaa ttgtgagcgg ataacaattt    1140
cacacaggaa acagctatga ccatgattac gccaagcgcg caattaaccc tcactaaagg    1200
gaacaaaagc tggagctgca agcttggcca ttgcatacgt tgtatccata tcataatatg    1260
tacatttata ttggctcatg tccaacatta ccgccatgtt gacattgatt attgactagt    1320
tattaatagt aatcaattac ggggtcatta gttcatagcc catatatgga gttccgcgtt    1380
acataactta cggtaaatgg cccgcctggc tgaccgccca acgacccccg cccattgacg    1440
tcaataatga cgtatgttcc catagtaacg ccaatagggac ctttccattg acgtcaatgg   1500
gtggagtatt tacggtaaac tgcccacttg gcagtacatc aagtgtatca tatgccaagt    1560
acgcccccta ttgacgtcaa tgacggtaaa tggcccgcct ggcattatgc ccagtacatg    1620 acctttatggg actttcctac ttggcagtac atctacgtat tagtcatcgc tattaccatg   1680
gtgatgcggt tttggcagta catcaatggg cgtggatagc ggtttgactc acggggattt    1740
ccaagtctcc accccattga cgtcaatggg agtttgtttt ggcaccaaaa tcaacgggac    1800
tttccaaaat gtcgtaacaa ctccgcccca ttgacgcaaa tgggcggtag gcgtgtacgg    1860
tgggaggtct atataagcag agctcgttta gtgaaccggg gtctctctgg ttagaccaga    1920
tctgagcctg ggagctctct ggctaactag gaacccact gcttaagcct caataaagct     1980
tgccttgagt gcttcaagta gtgtgtgccc gtctgttgtg tgactctggt aactagagat    2040
ccctcagacc cttttagtca gtgtggaaaa tctctagcag tggcgcccga acagggacct    2100
gaaagcgaaa gggaaaccag agctctctcg acgcaggact cggcttgctg aagcgcgcac    2160
ggcaagaggc gaggggcggc gactggtgag tacgccaaaa atttttgacta gcggaggcta    2220 gaaggagaga gatgggtgcg agagcgtcag tattaagcgg gggagaatta gatcgcgatg    2280
ggaaaaaatt cggttaaggc cagggggaaa gaaaaaatat aaattaaaac atatagtatg    2340
ggcaagcagg gagctagaac gattcgcagt taatcctggc ctgttagaaa catcagaagg    2400
ctgtagacaa atactgggac agctacaacc atcccttcag acaggatcag aagaacttag    2460
atcattatat aatacagtag caaccctcta ttgtgtgcat caaaggatag agataaaaga    2520
caccaaggaa gctttagaca agatagagga agagcaaaac aaaagtaaga ccaccgcaca    2580
gcaagcggcc gctgatcttc agacctggag gaggagatat gagggacaat tggagaagtg    2640
aattatataa atataaagta gtaaaaattg aaccattagg agtagcaccc accaaggcaa    2700
agagaagagt ggtgcagaga gaaaaaagag cagtgggaat aggagctttg ttccttgggt    2760
tcttgggagc agcaggaagc actatgggcg cagcctcaat gacgctgacg gtacaggcca    2820
gacaattatt gtctggtata gtgcagcagc agaacaattt gctgagggct attgaggcgc    2880
aacagcatct gttgcaactc acagtctggg gcatcaagca gctccaggca agaatcctgg    2940
ctgtggaaag atacctaaag gatcaacagc tcctggggat ttggggttgc tctggaaaac    3000
tcatttgcac cactgctgtg ccttggaatg ctagttggag taataaatct ctggaacaga    3060
```

| | |
|---|---|
| tttggaatca cacgacctgg atggagtggg acagagaaat taacaattac acaagcttaa | 3120 |
| tacactcctt aattgaagaa tcgcaaaacc agcaagaaaa gaatgaacaa gaattattgg | 3180 |
| aattagataa atgggcaagt tgtggaatt ggtttaacat aacaaattgg ctgtggtata | 3240 |
| taaaattatt cataatgata gtaggaggct tggtaggttt aagaatagtt tttgctgtac | 3300 |
| tttctatagt gaatagagtt aggcagggat attcaccatt atcgtttcag acccacctcc | 3360 |
| caaccccgag gggaccccgac aggcccgaag gaatagaaga agaaggtgga gagagagaca | 3420 |
| gagacagatc cattcgatta gtgaacggat ctcgacggta tcggttaact tttaaaagaa | 3480 |
| aaggggggat tggggggtac agtgcagggg aaagaatagt agacataata gcaacagaca | 3540 |
| tacaaactaa agaattacaa aaacaaatta caaaaattca aaattttatc gataagcttg | 3600 |
| ggagttccgc gtgttggggg tggaccatcc tctaggtatt gaataagaaa aatgaagtta | 3660 |
| aggtggttga tggtaacact atgctaataa ctgcagagcc agaagcacca taagggacat | 3720 |
| gataagggag ccagcagacc tctgatctct cctgaatgc taatcttaaa catcctgagg | 3780 |
| aagaatggga cttccatttg gggtgggcct atgatagggt aataagacag tagtgaatat | 3840 |
| caagctacaa aaagcccct ttcaaattct tctcagtcct aacttttcat actaagccca | 3900 |
| gtccttccaa agcagactgt gaaagagtga tagttccggg agactagcac tgcagattcc | 3960 |
| gggtcactgt gagtggggga ggcagggaag aagggctcac aggacagtca aaccatgccc | 4020 |
| cctgtttttc cttcttcaag tagacctcta taagacaaca gagacaacta aggctgagtg | 4080 |
| gccaggcgag gagaaaccat ctcgccgtaa acatggaag gaacacttca ggggaaaggt | 4140 |
| ggtatctcta agcaagagaa ctgagtggag tcaaggctga gagatgcagg ataagcaaat | 4200 |
| gggtagtgaa aagacattca tgaggacagc taaaacaata agtaatgtaa aatacagcat | 4260 |
| agcaaaactt taacctccaa atcaagcctc tacttgaatc cttttctgag ggatgaataa | 4320 |
| ggcataggca tcaggggctg ttgccaatgt gcattagctg tttgcagcct caccttcttt | 4380 |
| catggagttt aagatatagt gtattttccc aaggtttgaa ctagctcttc atttcttat | 4440 |
| gttttaaatg cactgacctc ccacattccc tttttagtaa aatattcaga ataatttaa | 4500 |
| atacatcaag cgcttgctgc ccactcagac tttattcaaa gaccaggaag ggccggtgca | 4560 |
| aggaggggag gagggcccgt tgggaggccc agcgggcagg aggaacggct accgaggctc | 4620 |
| cagcttaccg gtacttgctt gtcagcacgg tggacacgct ggccagaaac ttgtccagag | 4680 |
| aggcgtgcac tgcaggtgtg aactctgctg gcaggtgtgc tgccagggtc accagcaggc | 4740 |
| agtggctcag cagctgtgca gagaagaggg tcagtcggc ccaggcccgc agccgccgcc | 4800 |
| tgcgctacac ctcccgcaac ccgcgtgatc ctctgccctg agaggaaggc gccatctcgc | 4860 |
| ccctcgaccc agatcgctcc cggcccgccg ctcaccttga agttgaccgg gtccacccga | 4920 |
| agcttgtgcg cgtgcaggtc gctcagggcg gacagcgcgt tgggcatgtc gtccacgtgc | 4980 |
| gccacggcgt tggtcagcgc gtcggccacc ttcttgccgt ggcccttaac ctgggcagag | 5040 |
| ccgtggctca ggtcgaagtg cgggaagtag gtcttggtgg tggggaagga caggaacatc | 5100 |
| ctgcggggag aagcagagtg aggggtgggg tttgggtccg gggccaggac ggttgagggt | 5160 |
| ggcctgtggg tccgggcggg cgaggagccc ggtcggagc aggggaggga gcctcacctc | 5220 |
| tccagggcct cggcgccata ctcgccagcg tgcgcgccga ccttacccca gcggcccttg | 5280 |
| acgttggtct tgtcggcagg agacagcacc atggtgggtt ctctctgagt ctgtggggac | 5340 |
| cagaagagta agcaatagat ggctctgccc tgacttttat gccagccct ggctcctgcc | 5400 |
| ctccctgctc ctgggagtag attggccaac cctagggtgt ggctccacag ggtgaggtct | 5460 |

```
aagtgatgac agccgtacct gtccttggct cttctggcac tggcttagga gttggacttc   5520
aaaccctcag ccctccctct aagatatatc tcttggcccc ataccatcag tacaaattgc   5580
tactaaaaac atcctccttt gcaagtgtat ttacgtagta tacctcaagc ctcattcaga   5640
cactagtgtc accagtctcc tcatatacct attgtatttt cttcttcttg ctggtttagt   5700
catgttttct gggagcttag gggcttattt tattttgttt tgttttctaa tcaacagaga   5760
tgggcaaacc cattattttt ttctttagac ttgggatggt gatagctggg cagcgtcaga   5820
aactgtgtgt ggatatagat aagagctcag gactatgctg agctgtgatg agggaggggc   5880
ctagctaaag gcagtgagag tcagaatgct cctgctattg ccttctcagt ccccacgctt   5940
ggtttctaca caagtagata catagaaaag gctataggtt agtgtttgag agtcctgcat   6000
gattagttgc tcagaaatgc ccgataaata tgttatgtgt gtttatgtat atatatgttt   6060
tatatatata tatgtgtgtg tgtgtgtgtg tgtgtgtgtt gtgtttacaa atatgtgatt   6120
atcatcaaaa cgtgagggct aaagtgacca gataacttgc aagtcctagg ataccaggaa   6180
agtctagaat atgtcacatt ctgtctcagg catccatttt ctttatgatg ccgtttgagg   6240
tggagtttta gtcaggtggt cagcttctcc ttttttttgc catctgccct gtaagcatcc   6300
tgctggggac ccagatagga gtcatcactc taggctgaga acatctgggc acacaccta   6360 agcctcagca tgactcatca tgactcagca ttgctgtgct tgagccagaa ggtttgctta   6420
gaaggttaca cagaaccaga aggcgggggt ggggcactga ccccgacagg ggcctggcca   6480
gaactgctca tgcttggact atgggaggtc actaatggag acacacagaa atgtaacagg   6540
aactaaggaa aaactgaagc ttatttaatc agagatgaga tgctggaagg gatagaggga   6600
gctgagcttg taaaaagtat agtaatcatt cagcaaatgg ttttgaagca cctgctggat   6660
gctaaacact attttcagtg cttgaatcat aaataagaat aaaacatgta tcttattccc   6720
cacaagagtc caagtaaaaa ataacagtta attataatgt gctctgtccc ccaggctgga   6780
gtgcagtggc acgatctcag ctcactgcaa cctccgcctc ccgggcagct ggttagaagg   6840
ttctactgga ggagggtccc agcccattgc taaattaaca tcaggctctg agactggcag   6900
tatatctcta acagtggttg atgctatctt ctggaacttg cctgctacat tgagaccact   6960
gacccataca taggaagccc atagctctgt cctgaactgt taggccactg gtccagagag   7020
tgtgcatctc ctttgatcct cataataacc ctatgagata gacacaatta ttactcttac   7080
tttatagatg atgatcctga aaacatagga gtcaaggcac ttgcccctag ctgggggtat   7140
aggggagcag tccatgtag tagtagaatg aaaaatgctg ctatgctgtg cctcccccac   7200 cttcccatg tctgccctct actcatggtc tatctctcct ggctcctggg agtcatggac   7260 tccaccagc accaccaacc tgacctaacc acctatctga gcctgccagc ctataaccca   7320
tctgggccct gatagctggt ggccagccct gaccccaccc caccctccct ggaacctctg   7380
atagacacat ctggcacacc agctcgcaaa gtcaccgtga gggtcttgtg tttgctgagt   7440
caaaattcct tgaaatccaa gtccttagag actcctgctc ccaaatttac agtcatagac   7500
ttcttcatgg ctgtctcctt tatccacaga atgattcctt tgcttcattg ccccatccat   7560
ctgatcctcc tcatcagtgc agcacagggc ccatgagcag tagctgcaga gtctcacata   7620
ggtctggcac tgcctctgac atgtccgacc ttaggcaaat gcttgactct tctgagctca   7680
ccggtactag tgcatgcaaa tctgacactc agtgggcctg ggtgaaggtg agaattttat   7740
tgctgaatga gagcctctgg ggacatcttg ccagtcaatg agtctcaggt tcaatttcct   7800
```

```
tctcagtctt ggagtaacag aagctcatgc atttaataaa cggaaatttt gtattgaaat    7860
gagagccatt ggaaatcatt tactccagac tcctacttat aaaaagagaa actgaggctc    7920
agagaagggt ggggactttc tcagtatgac atggaaatga tcaggcttgg attcaaagct    7980
cctgactttc tgtctagtgt atgtgcagtg agccccttt cctctaactg aaagaaggaa     8040 aaaaaatgg aacccaaaat attctacata gtttccatgt cacagccagg ctgggcagt      8100 ctcctgttat ttcttttaaa ataaatatat catttaaatg cataaataag caaaccctgc    8160
tcgggaatgg gagggagagt ctctggagtc cacccttct cggccctggc tctgcagata     8220
gtgctatcaa agccctgaca gagccctgcc cattgctggg ccttggagtg agtcagccta    8280
gtagagaggc agggcaagcc atctcatagc tgctgagtgg gagagagaaa agggctcatt    8340
gtctataaac tcaggtcatg gctattctta ttctcacact aagaaaaaga atgagatgtc    8400
tacatatacc ctgcgtcccc tcttgtgtac tggggtcccc aagagctctc taaaagtgat    8460
ggcaaagtca ttgcgctaga tgccatccca tctattataa acctgcattt gtctccacac    8520
accagtcatg gacaataacc ctcctcccag gtccacgtgc ttgtctttgt ataatactca    8580
agtaatttcg gaaaatgtat tctttcaatc ttgttctgtt attcctgttt caatggctta    8640
gtagaaaaag tacatacttg ttttcccata aattgacaat agacaatttc acatcaatgt    8700
ctatatgggt cgttgtgttt gctgtgtttg caaaaactca caataacttt atattgttac    8760
tactctaaga aagttacaac atggtgaata caagagaaag ctattacaag tccagaaaat    8820
aaaagttatc atcttgaggc ctcctgcagg gtacctttaa gaccaatgac ttacaaggca    8880
gctgtagatc ttagccactt tttaaaagaa aaggggggac tggaagggct aattcactcc    8940
caacgaagac aagatctgct ttttgctgtg cgggccaggc cccgagggc cttatcggcc     9000 ccagaggcgc ttgctgtcgg gccgggcgct cccggcacgg gcgggcgag gggtggcgcc     9060 cgcctgggga ccgcagatta caagagcacc tcctccccca accccaggag gccccgctcc    9120
ccaggcctcg gccggcgcgg acccctggtt gccccggact gggtctctct ggttagacca    9180
gatctgagcc tgggagctct ctggctaact agggaaccca ctgcttaagc ctcaataaag    9240
cttgccttga gtgcttcaag tagtgtgtgc ccgtctgttg tgtgactctg gtaactagag    9300
atccctcaga cccttttagt cagtgtggaa aatctctagc aggctagcaa acaaaagacg    9360
tacgagctat gctttaatta aagctatgct gtcgacaatc aacctctgga ttacaaaatt    9420
tgtgaaagat tgactggtat tcttaactat gttgctcctt ttacgctatg tggatacgct    9480
gctttaatgc ctttgtatca tgctattgct tcccgtatgg ctttcatttt ctcctccttg    9540
tataaatcct ggttgctgtc tctttatgag gagttgtggc ccgttgtcag gcaacgtggc    9600
gtggtgtgca ctgtgtttgc tgacgcaacc cccactggtt ggggcattgc caccacctgt    9660
cagctccttt ccgggacttt cgctttcccc ctccctattg ccacggcgga actcatcgcc    9720
gcctgccttg cccgctgctg gacagggct cggctgttgg gcactgacaa ttccgtggtg    9780
ttgtcgggga agctgacgtc cttcatggc tgctcgcct gtgttgccac ctggattctg     9840
cgcgggacgt ccttctgcta cgtcccttcg gccctcaatc cagcggacct ccttcccgc    9900 ggcctgctgc cggctctgcg gcctcttccg cgtcttcgcc ttcgccctca gacgagtcgg    9960
atctcccttt gggccgcctc cccgcctgga attcgagctc ggtacctgat cagcctcgac   10020
tgtgccttct agttgccagc catctgttgt ttgcccctcc ccgtgccttt ccttgaccct   10080
ggaaggtgcc actcccactg tccttttccta ataaaatgag gaaattgcat cgcattgtct   10140
gagtaggtgt cattctattc tggggggtgg ggtggggcag gacagcaagg gggaggattg   10200
```

```
ggaagacaat agcaggcatg ctggggatgc ggtgggctct atggcttctg aggaaagaac    10260 cagctgggc tcgagatcca ctagttctag cctcgaggct agagcggccg ccaccgcggt     10320
agtagttcat gtcatcttat tattcagtat ttataacttg caaagaaatg aatatcagag    10380
agtgagagga acttgtttat tgcagcttat aatggttaca aataaagcaa tagcatcaca    10440
aatttcacaa ataaagcatt ttttcactg cattctagtt gtggtttgtc caaactcatc     10500
aatgtatctt atcatgtctg gctctagcta tcccgcccct aactccgccc agttccgccc    10560
attctccgcc ccatggctga ctaatttttt ttatttatgc agaggccgag gccgcctcgg    10620
cctctgagct attccagaag tagtgaggag gcttttttgg aggcctaggc ttttgcgtcg    10680
agacgtaccc aattcgccct atagtgagtc gtattacgcg cgctcactgg ccgtcgtttt    10740
acaacgtcgt gactgggaaa accctggcgt tacccaactt aatcgccttg cagcacatcc    10800 cccttcgcc agctggcgta atagcgaaga ggcccgcacc gatcgccctt cccaacagtt     10860
gcgcagcctg aatggcgaat ggcgcgacgc gccctgtagc ggcgcattaa gcgcggcggg    10920
tgtggtggtt acgcgcagcg tgaccgctac acttgccagc gccctagcgc ccgctccttt    10980
cgctttcttc ccttcctttc tcgccacgtt cgccggcttt cccgtcaag ctctaaatcg     11040 ggggctccct ttagggttcc gatttagtgc tttacggcac ctcgacccca aaaaacttga    11100
ttagggtgat ggttcacgta gtgggccatc gccctgatag acggttttc gccctttgac     11160 gttggagtcc acgttcttta atagtggact cttgttccaa actggaacaa cactcaaccc    11220
tatctcggtc tattcttttg atttataagg gattttgccg atttcggcct attggttaaa    11280
aaatgagctg atttaacaaa aatttaacgc gaattttaac aaaatattaa cgtttacaat    11340
ttcccaggtg cacttttcg gggaaatgtg cgcggaaccc ctatttgttt attttttctaa    11400 atacattcaa atatgtatcc gctcatgaga caataaccct gataaatgct tcaataatat    11460
tgaaaaagga agagtatgag tattcaacat ttccgtgtcg cccttattcc cttttttgcg    11520
gcattttgcc ttcctgtttt tgctcaccca gaaacgctgg tgaaagtaaa agatgctgaa    11580
gatcagttgg gtgcacgagt gggttacatc gaactggatc tcaacagcgg taagatcctt    11640
gagagttttc gccccgaaga acgttttcca atgatgagca cttttaaagt tctgctatgt    11700
ggcgcggtat tatcccgtat tgacgccggg caagagcaac tcggtcgccg catacactat    11760
tctcagaatg acttggttga gtactcacca gtcacagaaa agcatcttac ggatggcatg    11820
acagtaagag aattatgcag tgctgccata accatgagtg ataacactgc ggccaactta    11880
cttctgacaa cgatcggagg accgaaggag ctaaccgctt ttttgcacaa catgggggat    11940
catgtaactc gccttgatcg ttgggaaccg gagctgaatg aagccatacc aaacgacgag    12000
cgtgacacca cgatgcctgt agcaatggca acaacgttgc gcaaactatt aactggcgaa    12060
ctacttactc tagcttcccg gcaacaatta atagactgga tggaggcgga taaagttgca    12120
ggaccacttc tgcgctcggc ccttccggct ggctggttta ttgctgataa atctggagcc    12180
ggtgagcgtg ggtctcgcgg tatcattgca gcactggggc cagatggtaa gccctcccgt    12240
atcgtagtta tctacacgac ggggagtcag gcaactatgg atgaacgaaa tagacagatc    12300
gctgagatag gtgcctcact gattaagcat tggtaa                              12336
```

COMPOSITIONS AND METHODS FOR HEMOGLOBIN PRODUCTION

This application is a § 371 application of PCT/US2019/051258, filed Sep. 16, 2019, which claims priority under 35 U.S.C. § 119(e) to U.S. Provisional Patent Application No. 62/731,508, filed Sep. 14, 2018. The foregoing applications are incorporated by reference herein.

FIELD OF THE INVENTION

The present invention relates to the field of hematology. More specifically, the invention provides compositions and methods for the production of hemoglobin.

BACKGROUND OF THE INVENTION

Several publications and patent documents are cited throughout the specification in order to describe the state of the art to which this invention pertains. Each of these citations is incorporated herein by reference as though set forth in full.

Alpha-thalassemia is an inherited condition affecting up to 5% of the world's population and resulting from insufficient production of alpha globin ($\alpha$-globin). However, unlike more well-known hemoglobinopathies such as beta-thalassemia and sickle cell disease (SCD), research into the detailed physiological disease characteristics and potential therapeutic options for $\alpha$-thalassemia has lagged behind.

In individuals with $\alpha$-thalassemia, mutations in the $\alpha$-globin genes or regulatory elements result in the production of fewer $\alpha$-globin chains, leading to decreased hemoglobin tetramer formation. Normal humans have four functional copies of $\alpha$-globin, while individuals with insufficient $\alpha$-globin production at 3 or 4 $\alpha$-globin loci suffer from Hemoglobin H disease (HbH) or Hb Bart's Hydrops Fetalis Syndrome, respectively. Treatment options typically include blood transfusions or in severe cases hematopoietic stem cell transplantation (HSCT). While offering the possibility of transfusion independence, HSCT requires a matched donor and can still result in immune rejection. Thus, there is an ongoing and unmet need for improved compositions and methods for treating $\alpha$-thalassemia.

SUMMARY OF THE INVENTION

In accordance with one aspect of the instant invention, vectors, particularly viral vectors such as lentiviral vectors, are provided. In a particular embodiment, the vector comprises a nucleic acid molecule comprising any one or more of: i) a 5' long terminal repeat (LTR) and a 3' LTR (e.g., at least one of the LTR may be self-inactivating); ii) at least one polyadenylation signal; iii) at least one promoter; iv) a globin gene locus control region (LCR); v) an ankyrin insulator element (Ank); vi) a Woodchuck Post-Regulatory Element (WPRE) (e.g., wherein the WPRE is 3' of the 3'LTR); vii) beta globin 3' enhancer; viii) a Rev response element (RRE) (e.g., from HIV); and/or ix) a sequence encoding human alpha globin. The instant invention also encompasses cells (e.g., hematopoietic stem cells, erythroid progenitor cells, or erythroid cells) comprising the vector (e.g., lentiviral vector) of the instant invention. Compositions comprising the vector (e.g., lentiviral vector) are also encompassed by the instant invention. The compositions may further comprise a pharmaceutically acceptable carrier.

In accordance with another aspect of the instant invention, methods of inhibiting, treating, and/or preventing alpha-thalassemia in a subject are provided. In a particular embodiment, the method comprises administering a viral vector of the instant invention to a subject in need thereof. In a particular embodiment, the method comprises an ex vivo therapy utilizing a viral vector of the instant invention. The viral vector may be in a composition with a pharmaceutically acceptable carrier.

BRIEF DESCRIPTIONS OF THE DRAWINGS

Figure 1B:
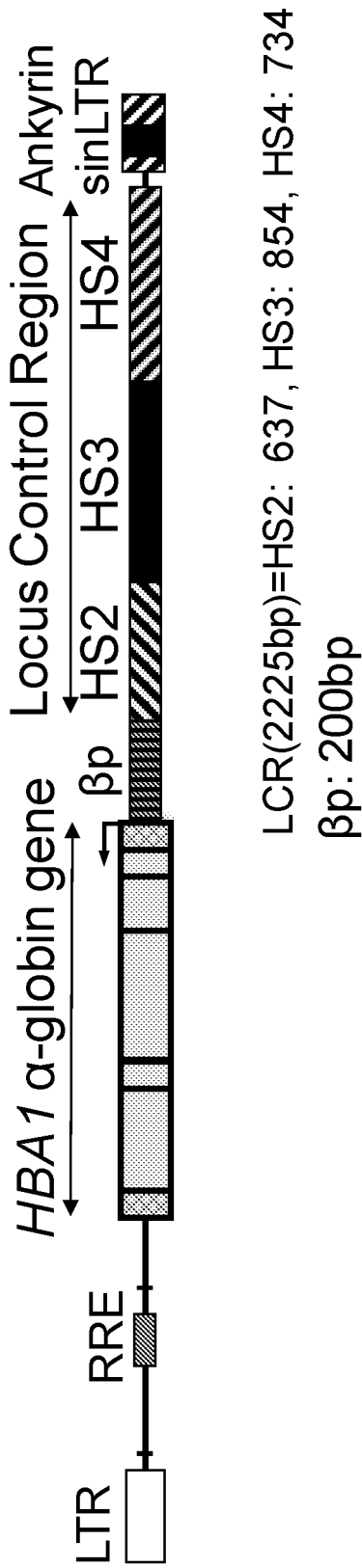

FIG. 1A provides a schematic of the Alpha1/AA305 vector. Alpha1/AA305 contains the alpha globin gene along with a subset of the human beta globin locus control region (LCR). FIG. 1B provides a detailed schematic of the region of the Alpha1/AA305 vector between the two viral LTRs. The lengths of the locus control region and hypersensitivity (HS) sites are provided.

Figure 2A:
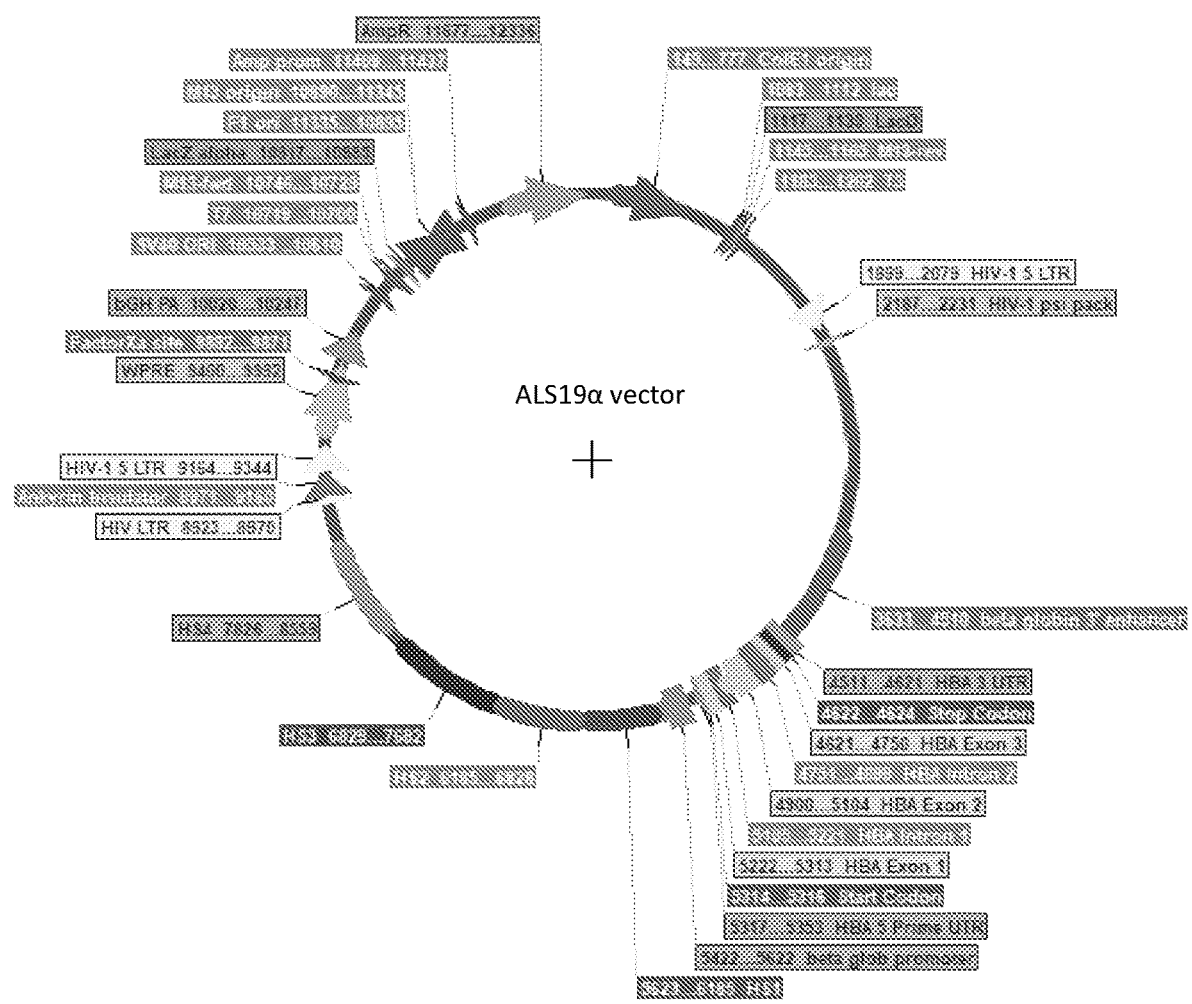
Figure 2B:
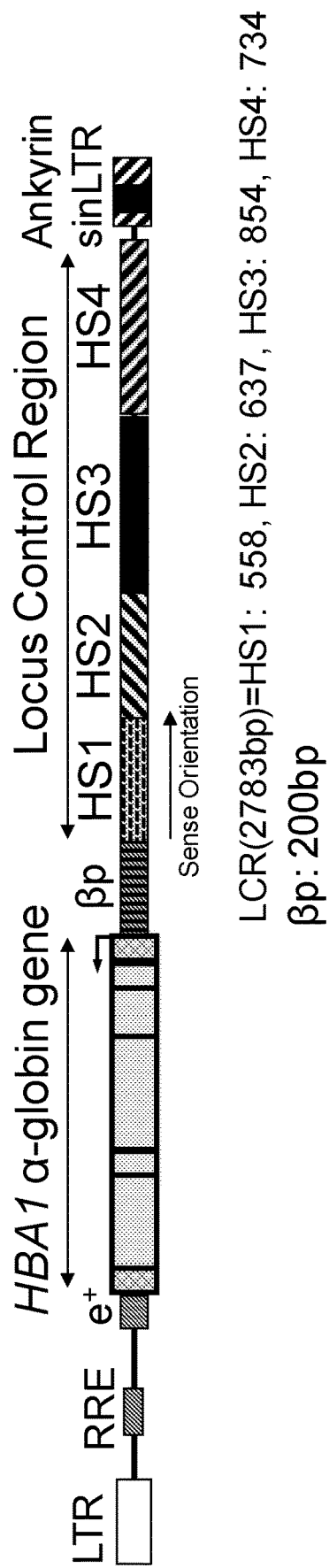

FIG. 2A provides a schematic of the ALS19$\alpha$ vector. ALS19$\alpha$ contains the human alpha globin gene along with a larger subset of the human Beta Globin LCR, as well as the 3' human beta globin enhancer. FIG. 2B provides a detailed schematic of the region of the ALS19$\alpha$ vector between the two viral LTRs. The lengths of the locus control region and HS sites are provided.

Figure 3A:
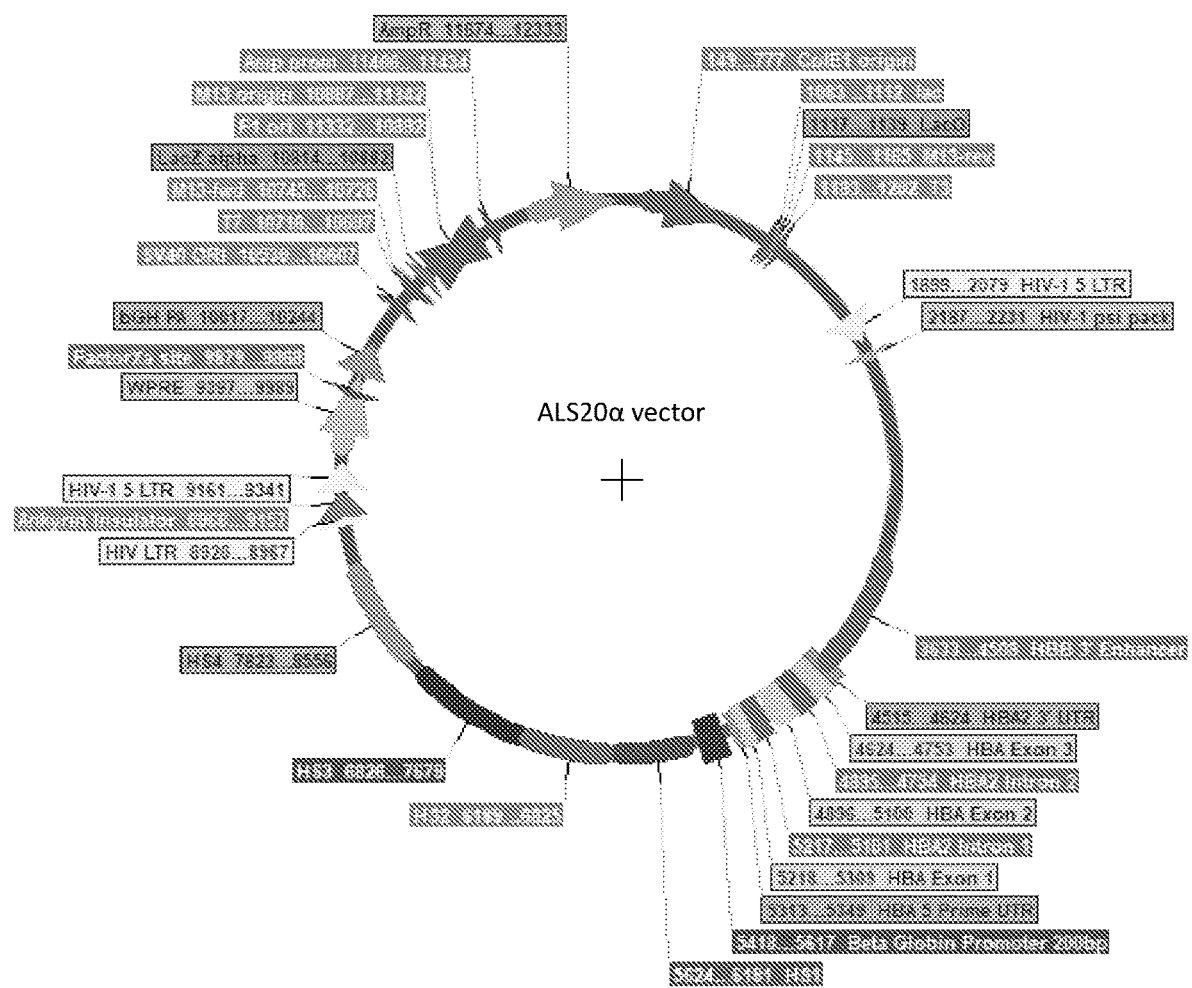
Figure 3B:
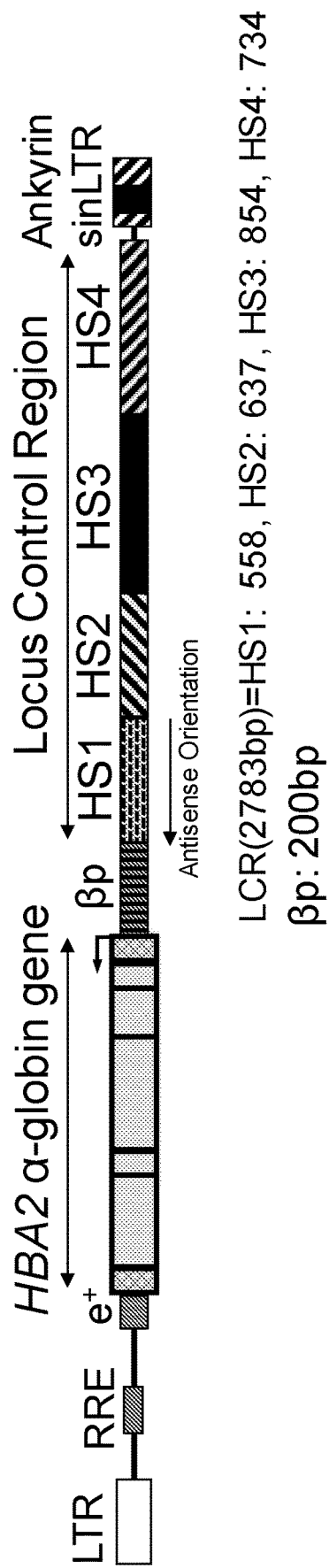

FIG. 3A provides a schematic of the ALS20$\alpha$ vector. ALS20$\alpha$ contains a different subset of the beta globin LCR relative to ALS19$\alpha$. FIG. 3B provides a detailed schematic of the region of the ALS20$\alpha$ vector between the two viral LTRs. The lengths of the locus control region and HS sites are provided.

Figure 4A:
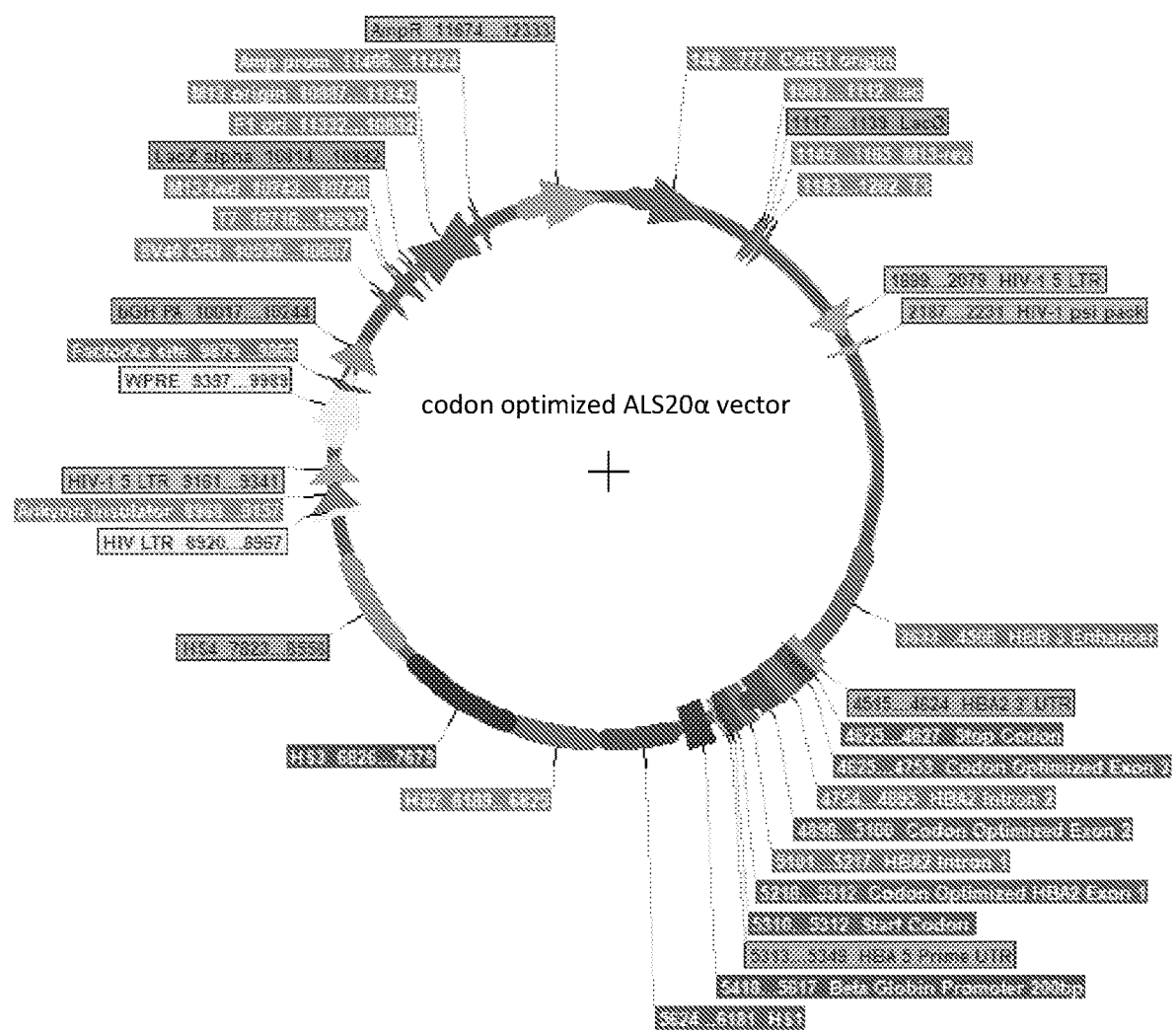
Figure 4B:
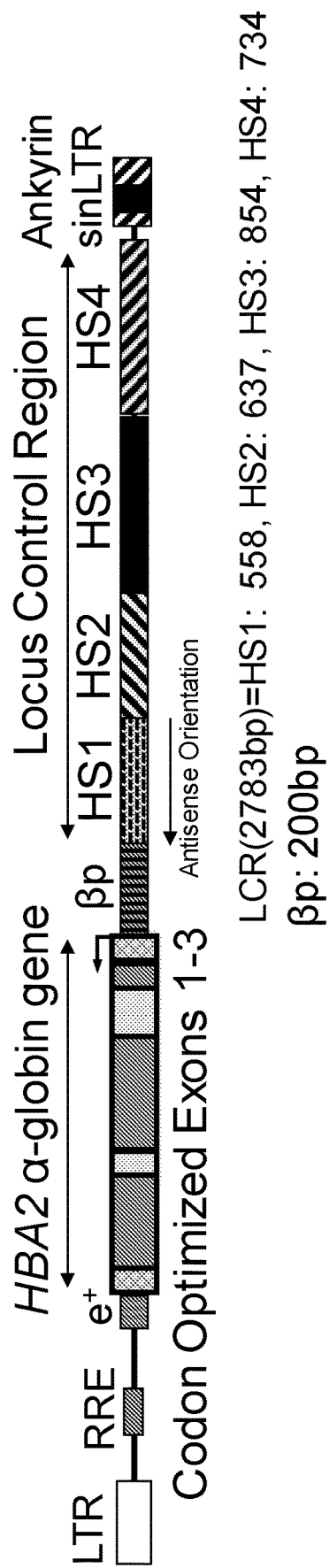

FIG. 4A provides a schematic of the codon optimized ALS20$\alpha$ vector. Codon optimized ALS20$\alpha$ is identical to ALS20$\alpha$ with the exception that portions of the alpha globin gene have been codon optimized for increased expression in humans. FIG. 4B provides a detailed schematic of the region of the codon optimized ALS20$\alpha$ vector between the two viral LTRs. The lengths of the locus control region and HS sites are provided.

Figure 5A:
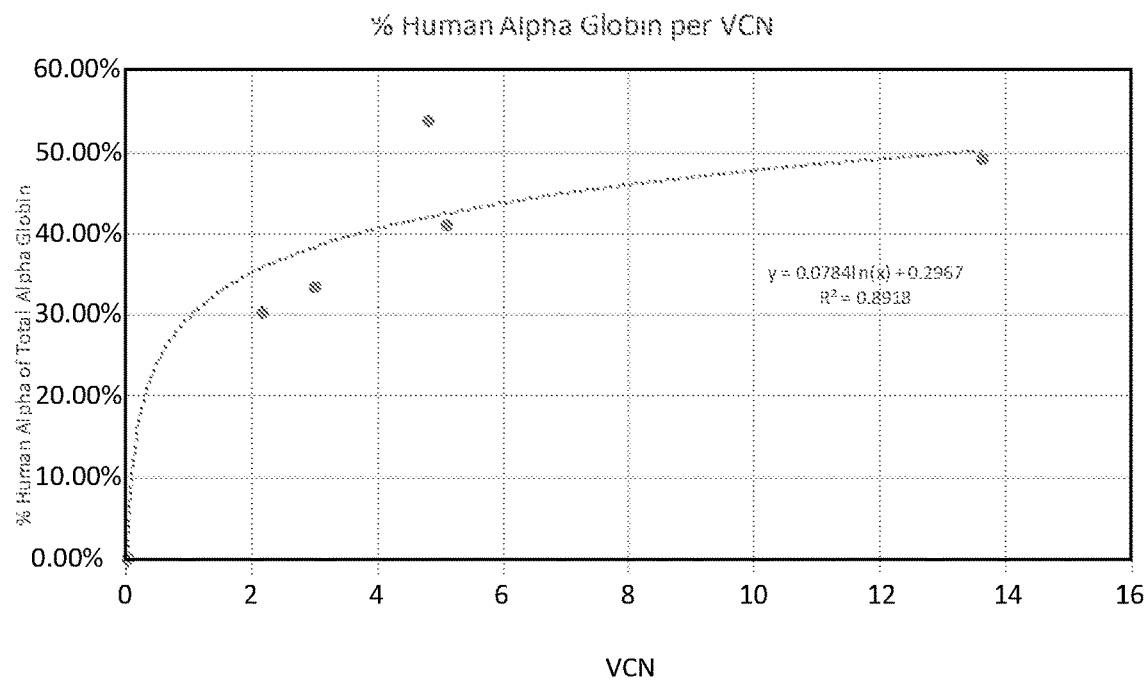
Figure 5B:
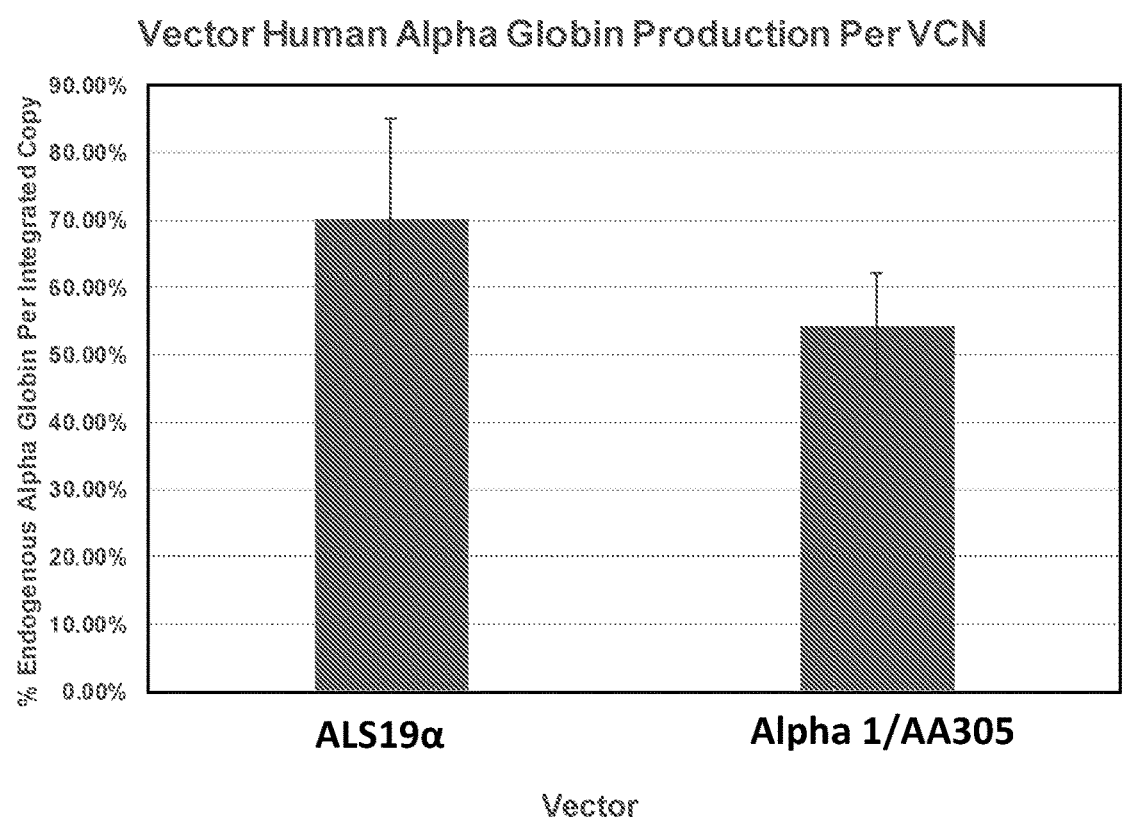
Figure 5C:
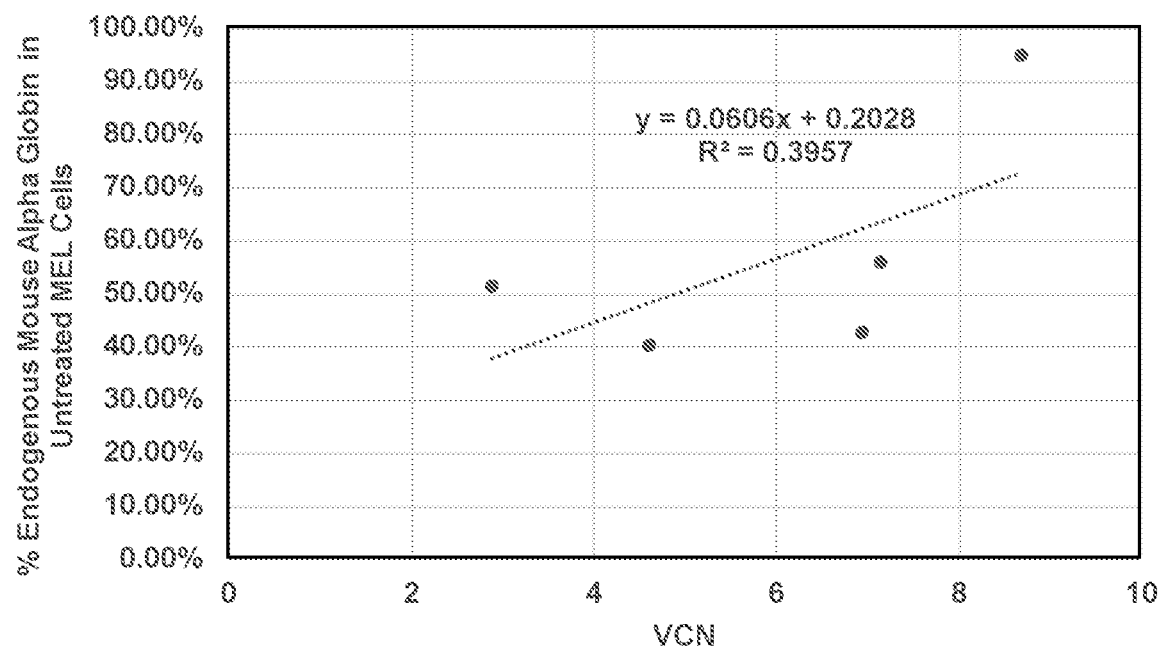

FIG. 5A provides a scatter plot of the percentage of human alpha globin produced of the total alpha globin per vector copy number (VCN) of the Alpha 1/AA305 vector. FIG. 5B provides a graph of the percent endogenous alpha globin produced per integrated copy of the indicated viral vector. FIG. 5C provides a plot of the ratio of human alpha-globin protein over the baseline level of the mouse alpha-globin protein over VCN by the vector ALS19$\alpha$.

Figure 6A:
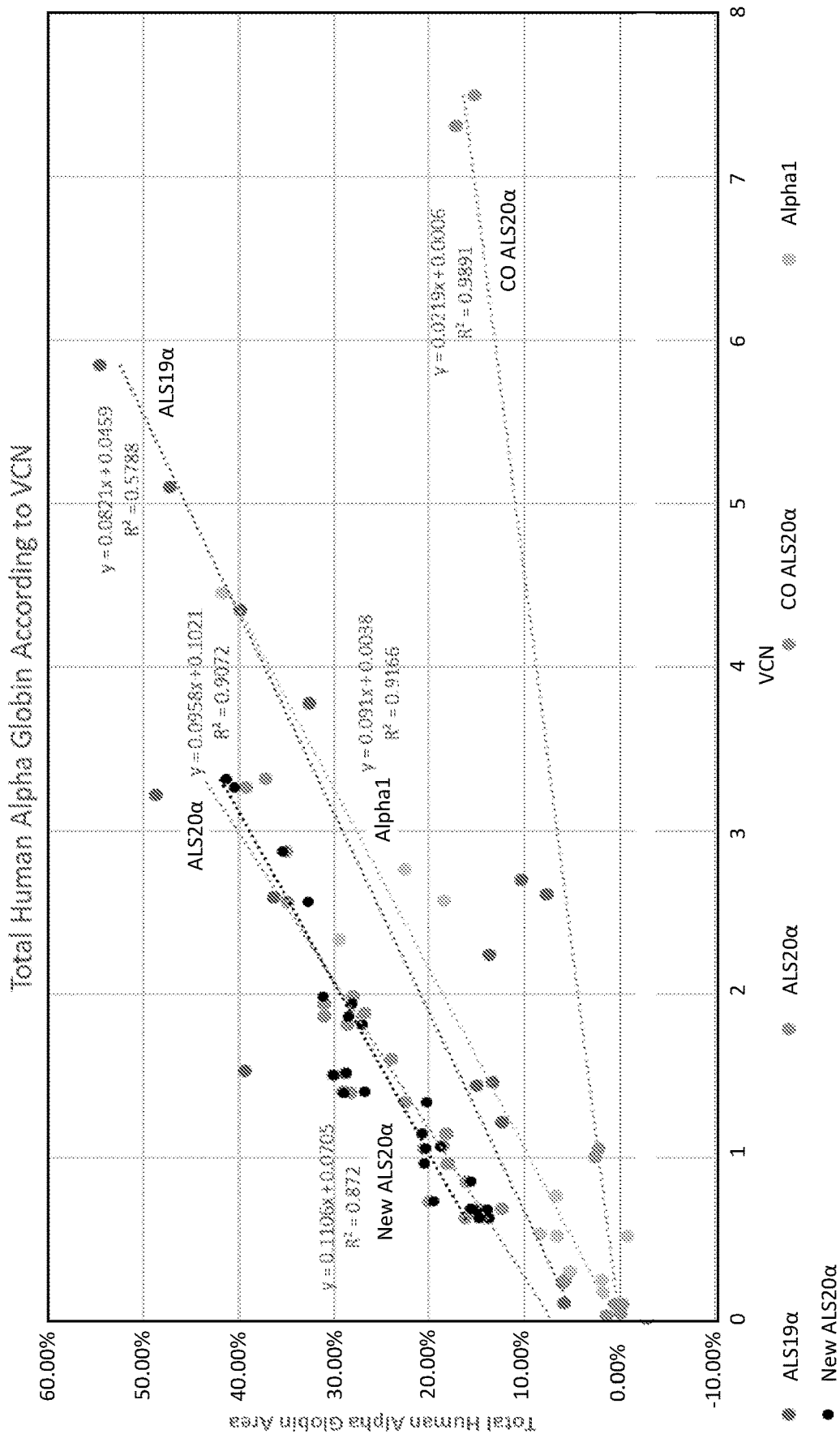
Figure 6B:
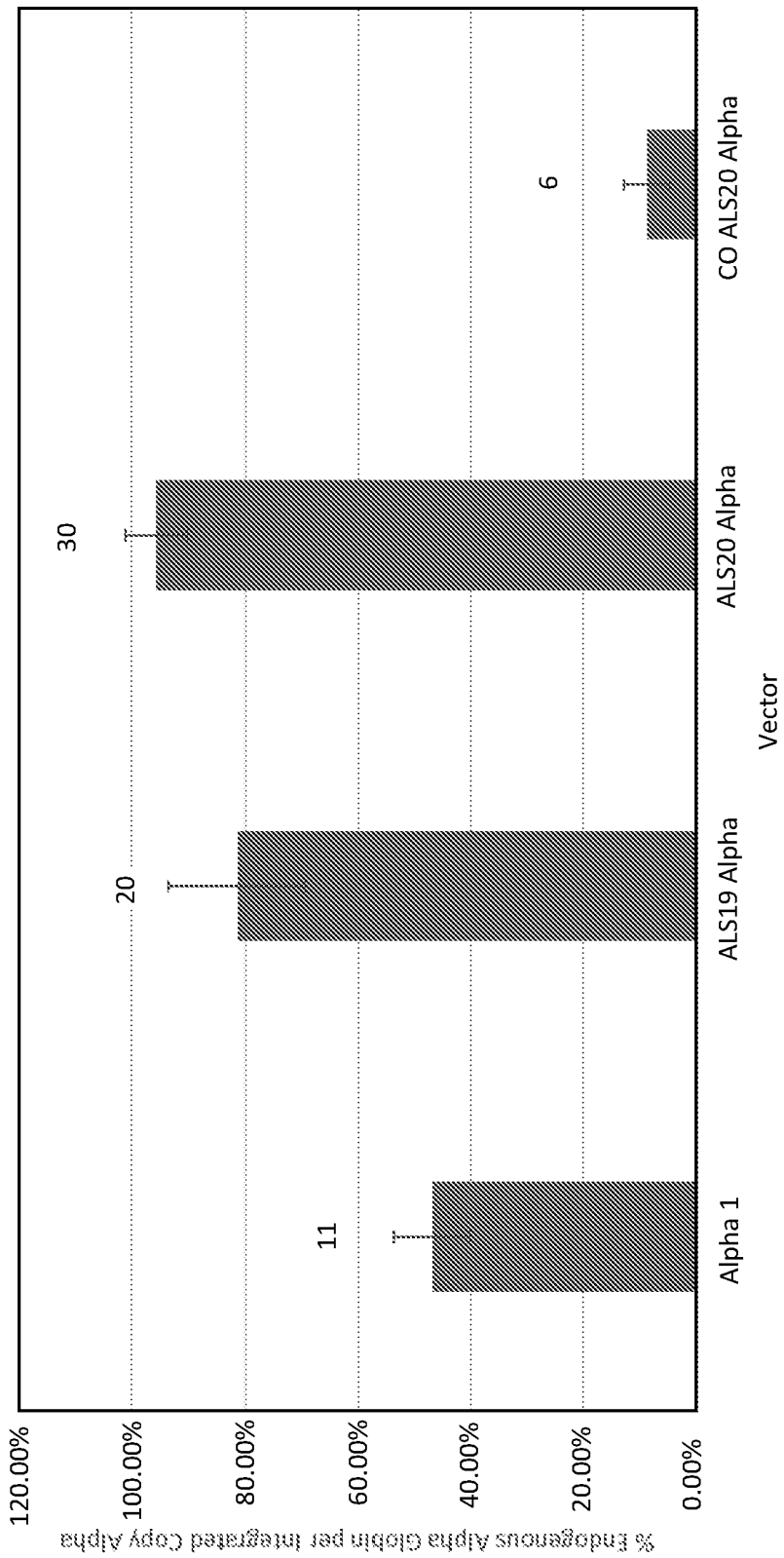

FIG. 6A provides a scatter plot of the percentage of human alpha globin produced of the total alpha globin per VCN of the Alpha 1/AA305 vector, ALS19$\alpha$ vector, ALS20$\alpha$ vector, and the codon-optimized ALS20$\alpha$ vector. FIG. 6B provides a graph of the percent endogenous alpha globin produced per integrated copy of the indicated viral vector. Error bars indicate the standard error of the mean.

Figure 7:
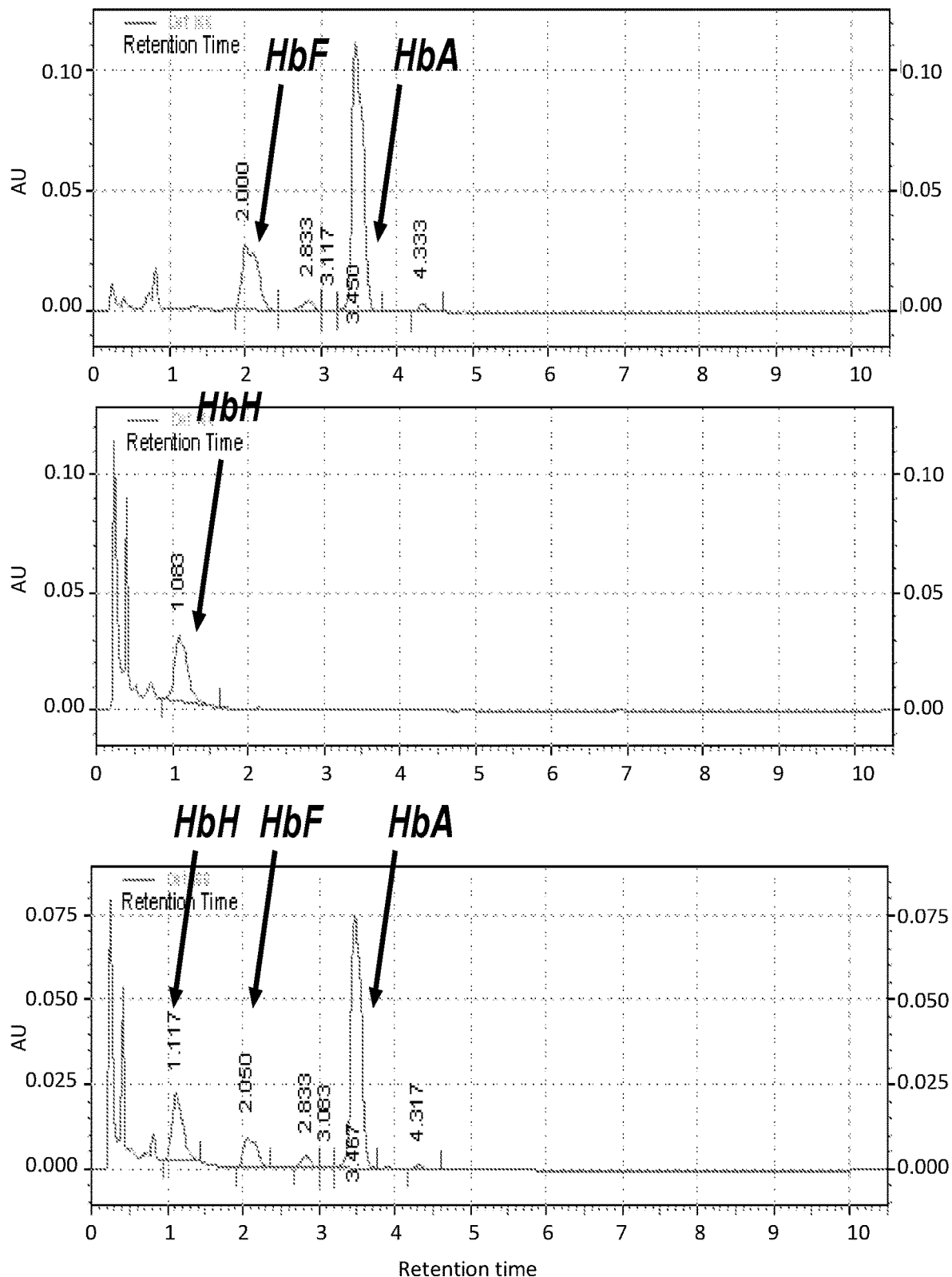

FIG. 7 provides RP-HPLC chromatograms of differentiated normal HUDEP cells (top), differentiated non-transduced alpha globin knockout HUDEPs (HUDEP 2 HBA1/2 KO Clone 7) (middle), and differentiated alpha globin knockout HUDEPs transduced with an alpha globin expressing lentiviral vector (bottom). The peaks corresponding to the level of fetal hemoglobin (HbF), adult hemoglobin (HbA), and hemoglobin H (HbH) are indicated.

Figure 8B:
Figure 8C:
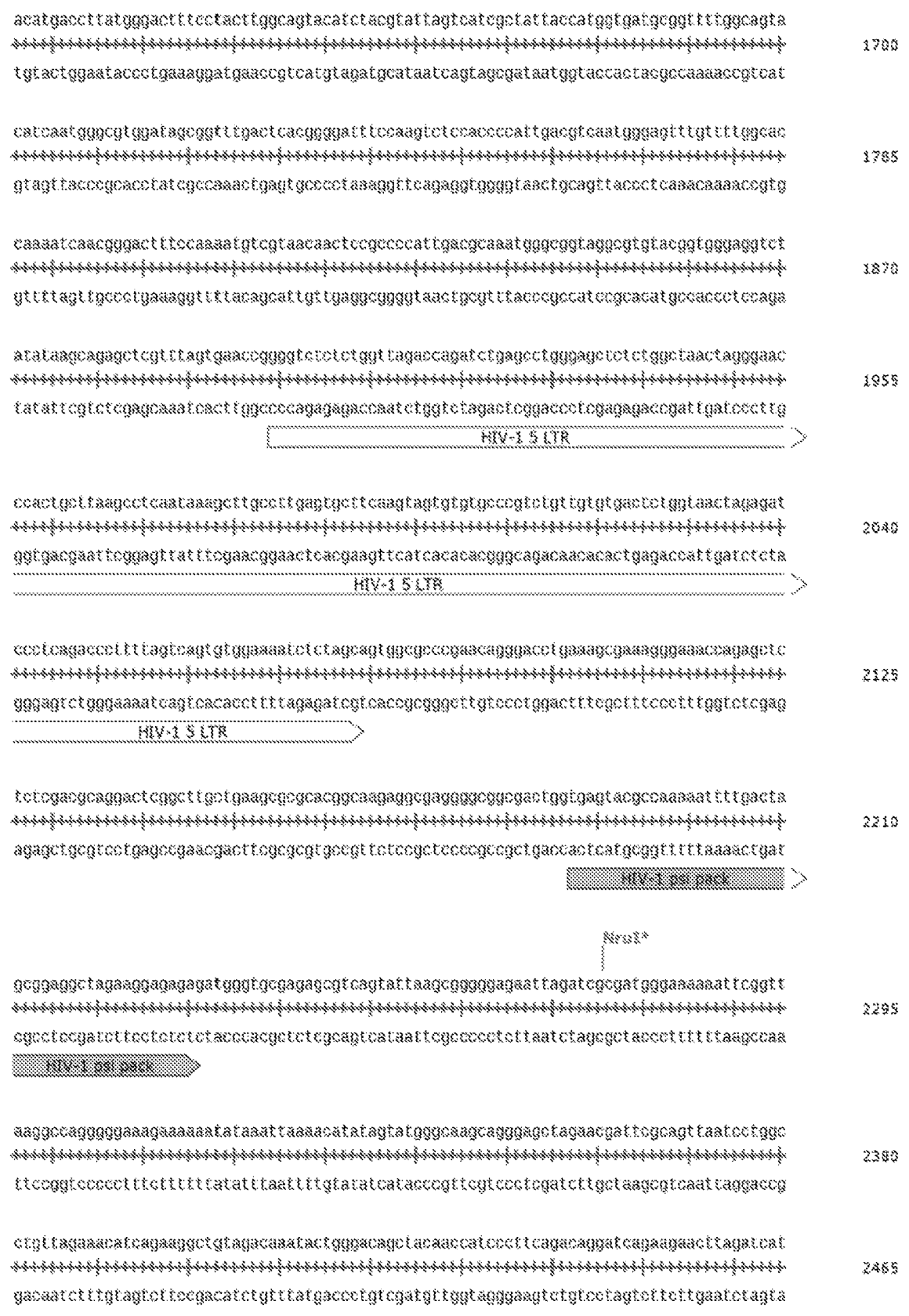
Figure 8F:
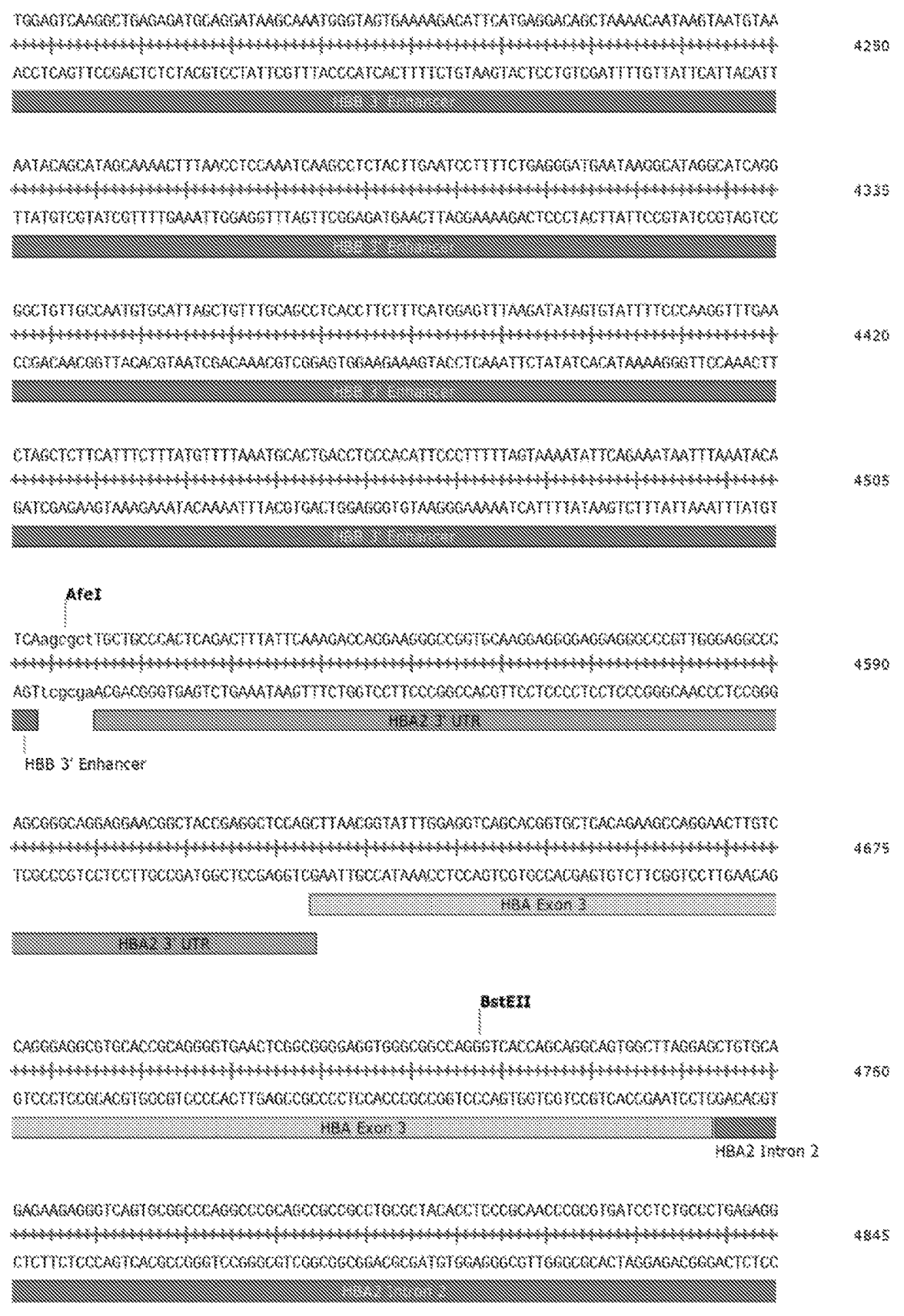
Figure 8I:
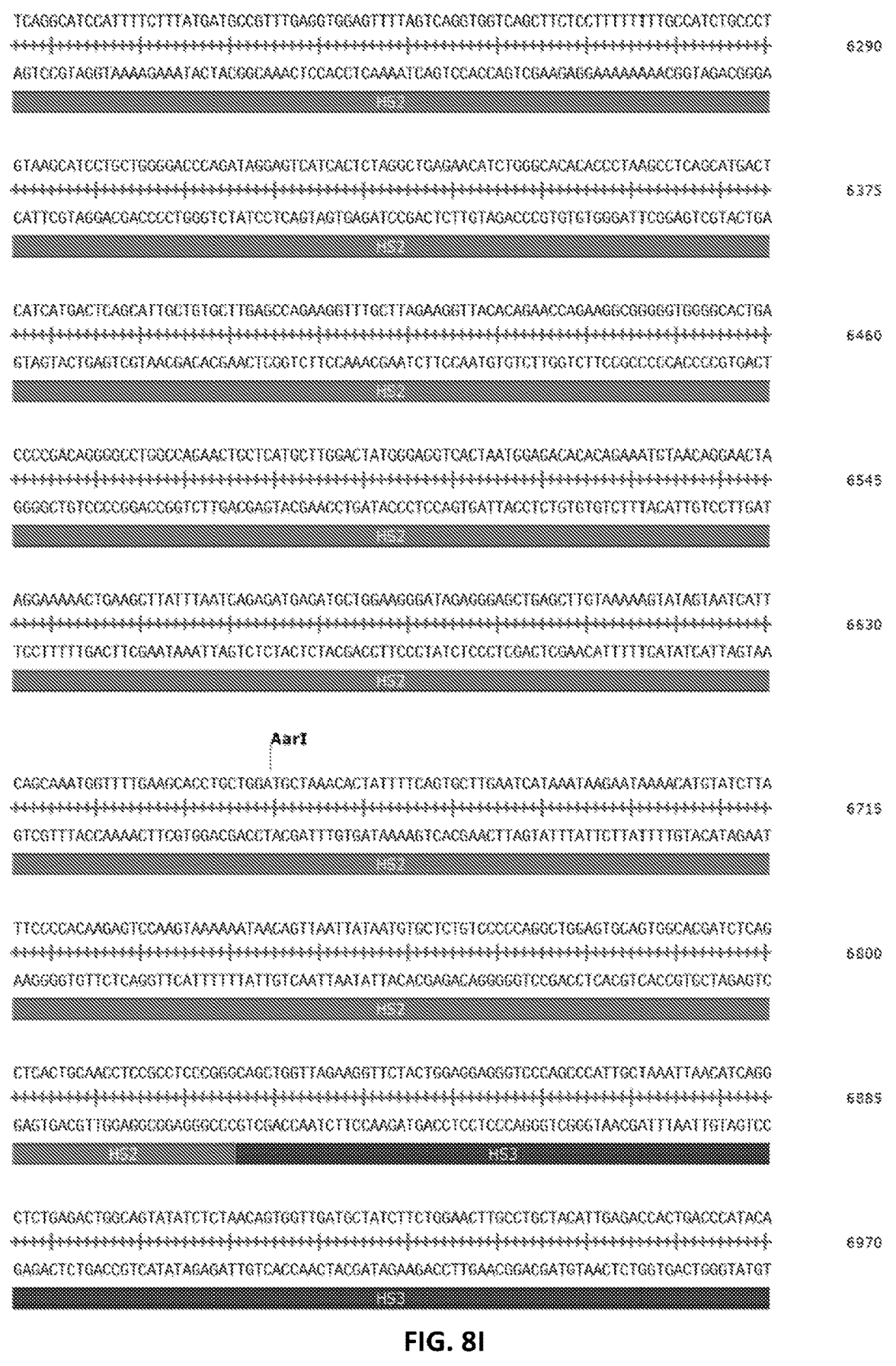
Figure 8L:
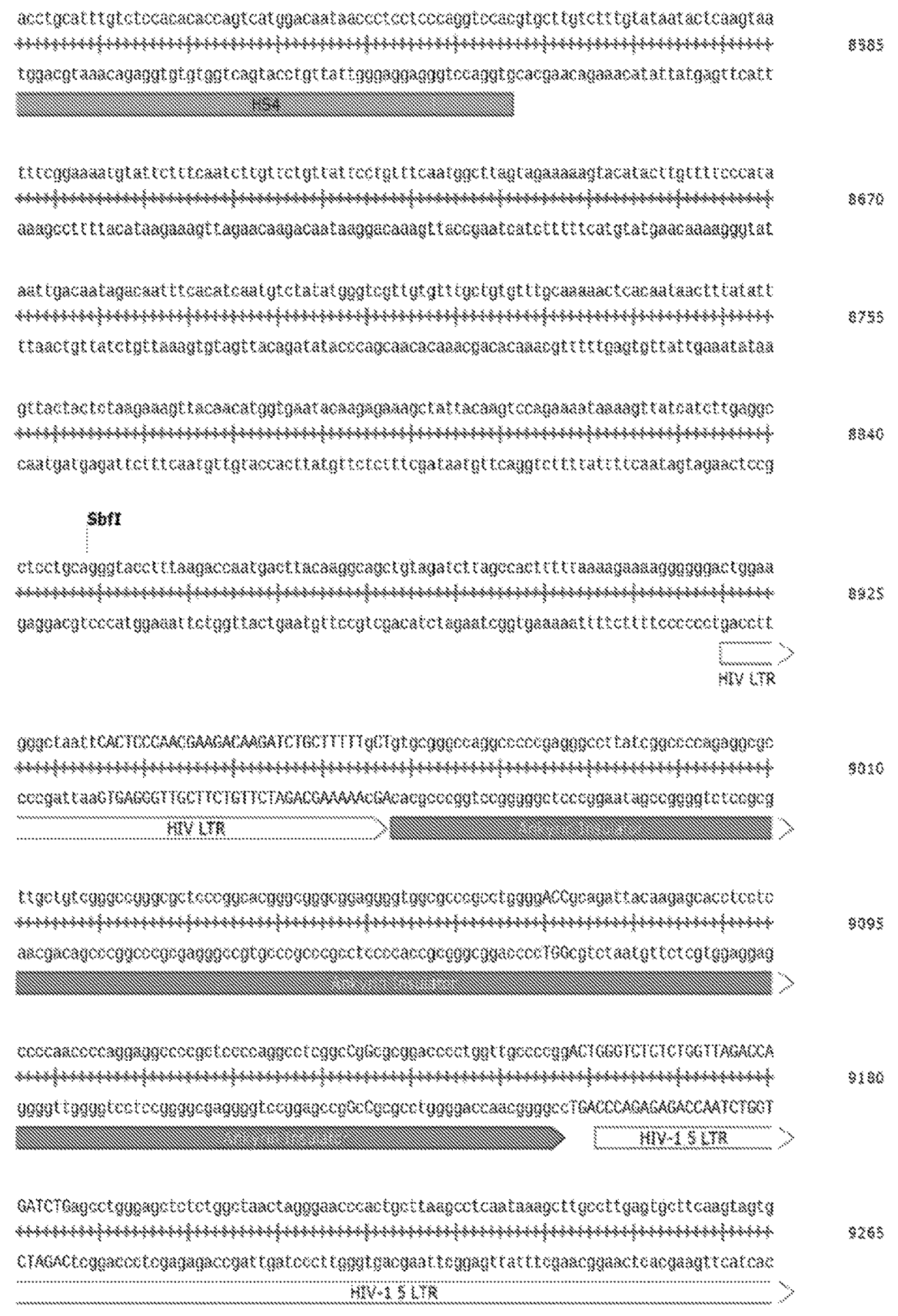
Figure 8N:
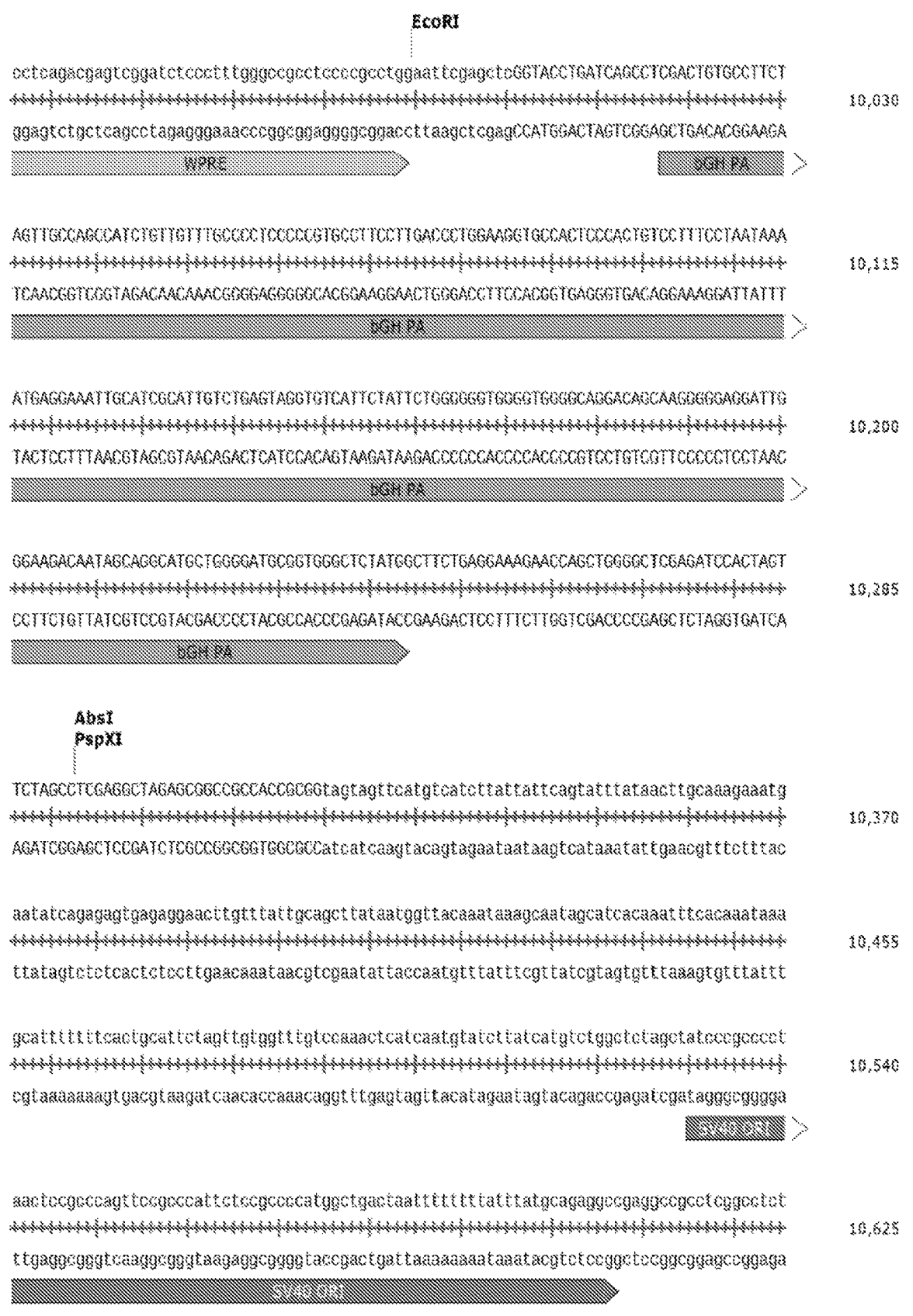
Figure 8P:
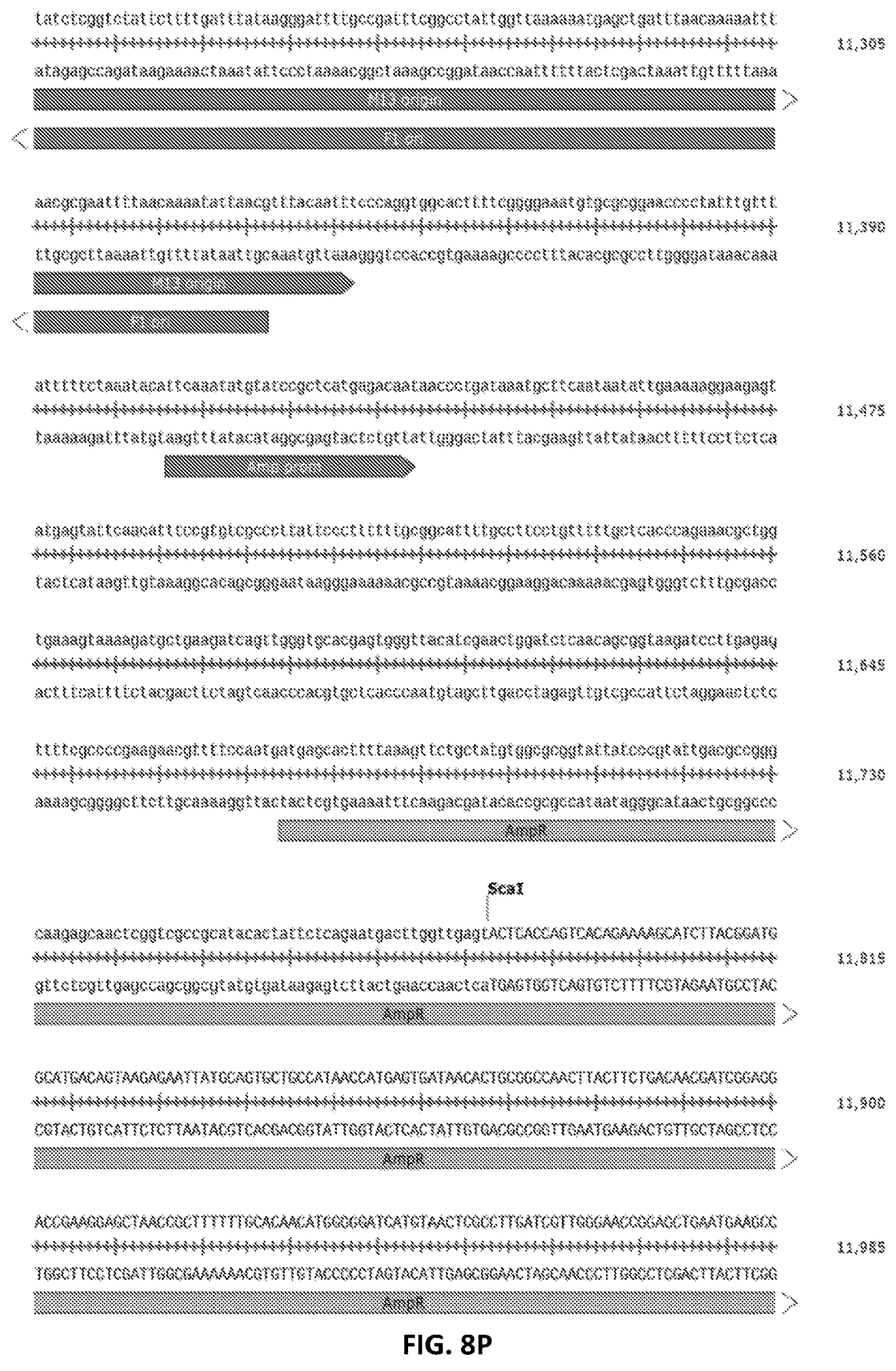

FIGS. 8A-8Q provide an annotated nucleotide sequence of vector ALS20$\alpha$. The sequence provided in FIGS. 8A-8Q is SEQ ID NO: 1 (double stranded representation).

Figure 9B:
Figure 9C:
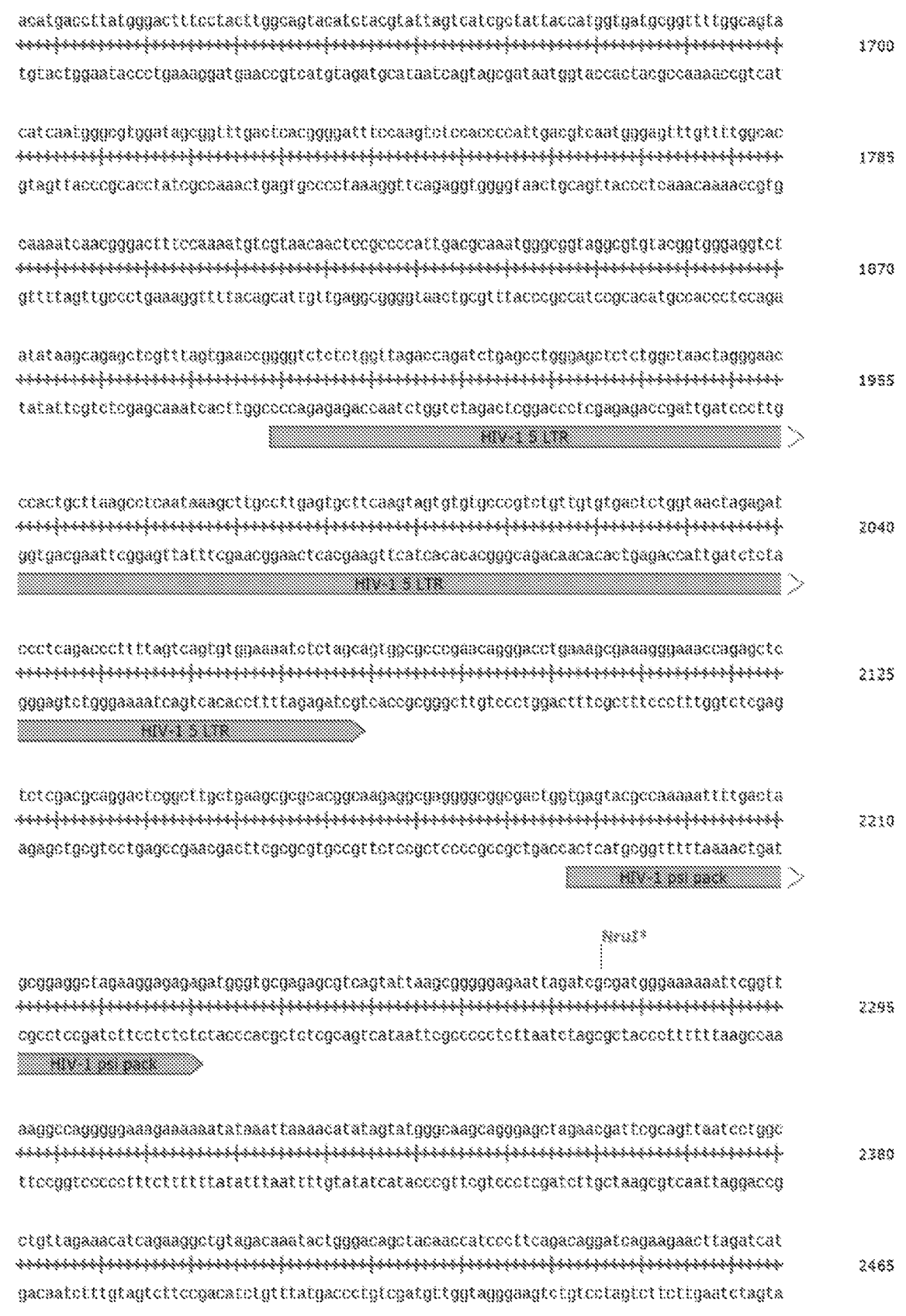
Figure 9J:
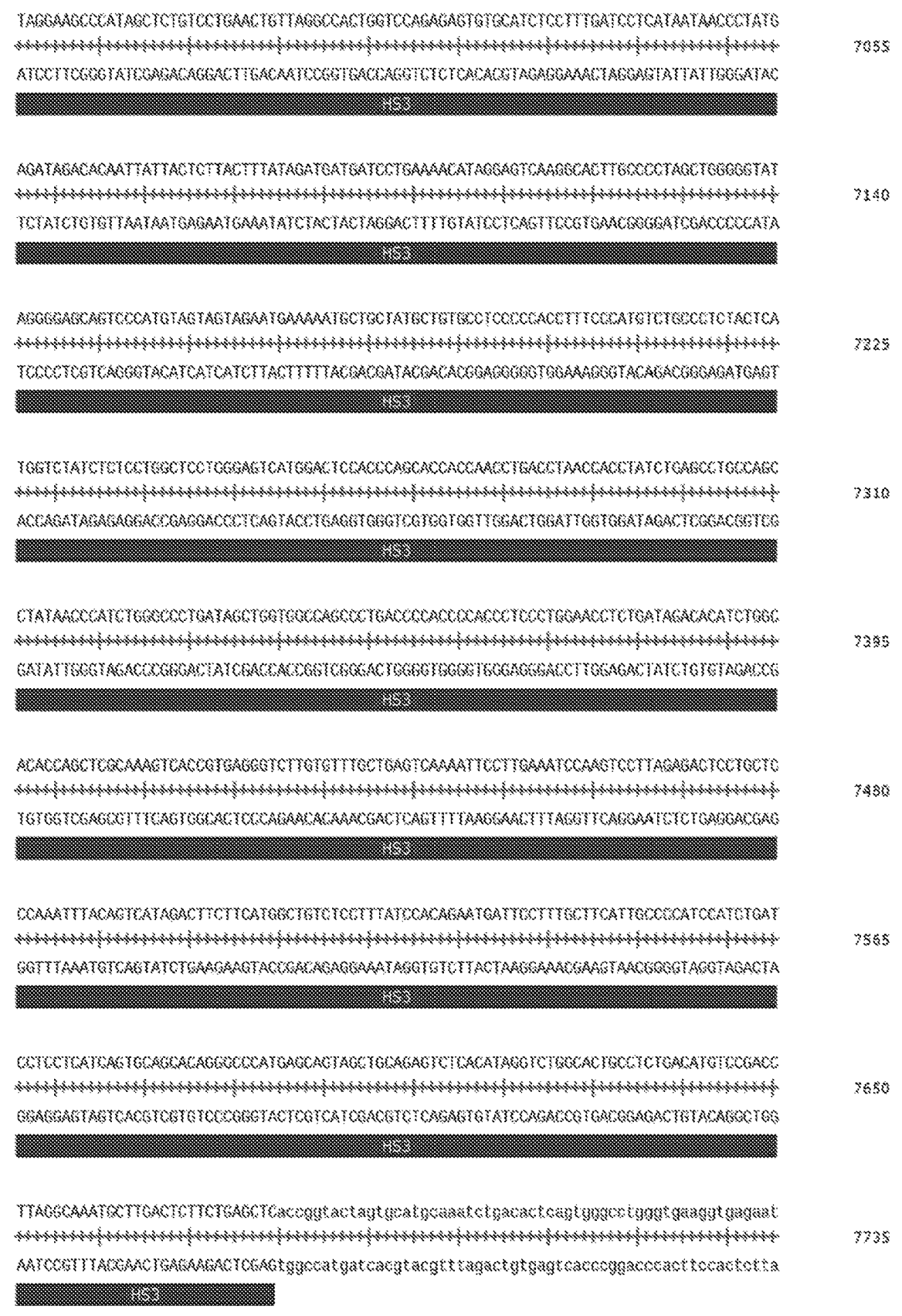
Figure 9L:
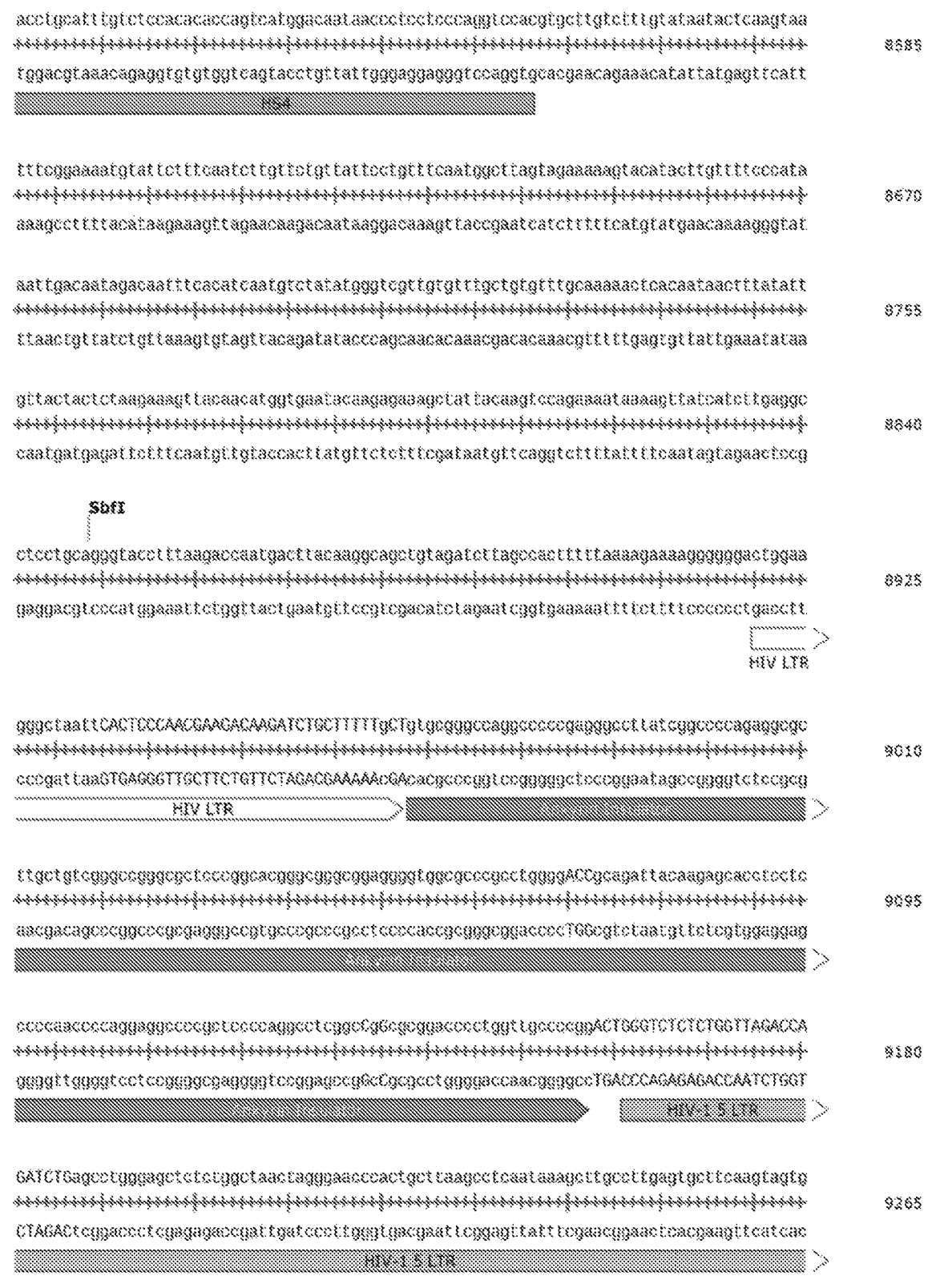
Figure 9P:
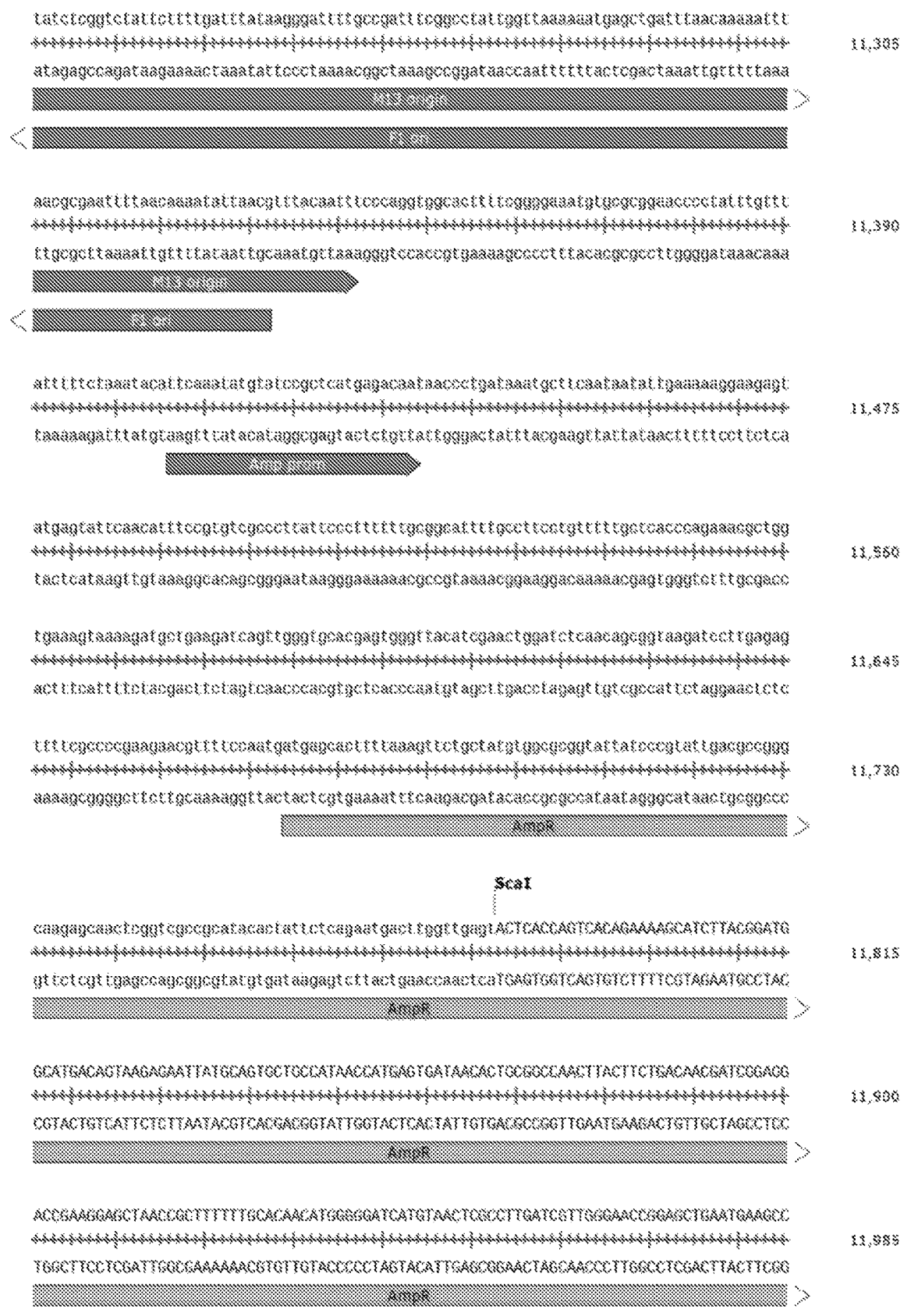

FIGS. 9A-9Q provide an annotated nucleotide sequence of vector ALS20$\alpha$ comprising a codon optimized alpha globin. The sequence provided in FIGS. 9A-9Q is SEQ ID NO: 2 (double stranded representation).

DETAILED DESCRIPTION OF THE INVENTION

Alpha-thalassemia is characterized by impaired production of alpha chains from 1, 2, 3, or all 4 of the alpha globin genes. This can lead to a relative excess of beta globin chains. Current treatment options include blood transfusions or hematopoietic stem cell transplantation (HSCT). However, HSCT requires a matched donor and can still result in immune rejection. The use of virus-treated (e.g., lentivirus treated) autologous hematopoietic stem cells (HSCs) offers a solution to these problems. Using autologous HSCs transduced with a vector expressing α-globin eliminates the need to locate a donor while simultaneously limiting the chance of graft vs. host disease.

Treatment of α-thalassemia via lentiviral vector treated HSCT requires not only strong, but tissue-specific alpha globin expression. Herein, alpha globin expressing vectors for the treatment of α-thalassemia are provided. In a particular embodiment, the vector comprises an alpha globin gene of alpha globin mRNA. In a particular embodiment, the vector comprises the Ankyrin insulator included with the HIV 3' self-inactivating (SIN) LTR and/or a WPRE included outside of the 3' LTR. In a particular embodiment, the integrating region of the vector is included in an antisense orientation. In a particular embodiment, the vector comprises various components of the β-globin regulatory machinery including, without limitation: HS1-HS4 of the β-globin locus control region (LCR), the β-globin promoter, and/or the β-globin 3' enhancer. In a particular embodiment, the alpha globin expressing vector is ALS19α or ALS20α. In a particular embodiment, the vectors of the instant invention (e.g., ALS19α, ALS20α) are codon optimized (e.g., to further increase synthesis of the alpha globin gene).

As demonstrated hereinbelow, the capacity for these vectors to produce human alpha globin was determined by transducing mouse erythroleukemia (MEL) cells and stimulating their differentiation. Following differentiation, red blood cell (RBC) lysates were analyzed via high-performance liquid chromatography (HPLC) to detect production of human alpha globin and differences between transduced and untransduced MEL cells. The data indicates that 1 copy of the vector of the instant invention can generate enough alpha globin chains to improve and/or correct alpha-thalassemia. Further experiments were performed that show that the vectors produce human alpha globin in human cells.

Figure 9F:

In accordance with the instant invention, vectors, particularly viral vectors such as lentiviral vectors, are provided. In a particular embodiment, the vector (e.g., lentiviral vector) comprises a nucleic acid molecule comprising any one or more of the following elements.

i) a 5' long terminal repeat (LTR) and a 3' LTR. In a particular embodiment, at least one of the LTR is self-inactivating. In a particular embodiment, at least the 3'LTR is self-inactivating. In a particular embodiment, the 5'LTR and/or 3'LTR are from HIV, particularly HIV-1. A self-inactivating LTR comprises a deletion or mutation relative to its native sequence that results in it being replication incompetent.

ii) at least one polyadenylation signal. It has been demonstrated that a strong bovine growth hormone polyA tail (e.g., inserted after the WPRE region) increases lentiviral titers (Zaiss, et al. (2002) J. Virol., 76(14): 7209-19).

iii) at least one promoter. In a particular embodiment, the promoter is a beta globin promoter. In a particular embodiment, the promoter is the 200 bp beta globin promoter. In a particular embodiment, the promoter is in antisense orientation. In a particular embodiment, the promoter controls the expression of human alpha globin (e.g., the promoter is operably linked to the sequence encoding human alpha globin).

iv) a globin gene locus control region (LCR). In a particular embodiment, the globin gene locus control region is a beta-globin gene locus control region. In a particular embodiment, the globin gene locus control region is operably linked to the promoter and/or sequence encoding human alpha globin. In a particular embodiment, the LCR comprises at least two, at least three, or all four of HS1, HS2, HS3, and HS4. In a particular embodiment, the LCR comprises HS2, HS3, and HS4. In a particular embodiment, the LCR comprises HS1, HS2, HS3, and HS4. In a particular embodiment, the LCR is in antisense orientation. In a particular embodiment, only HS2, HS3, and HS4 of the LCR are in antisense orientation.

v) an ankyrin insulator element (Ank). In a particular embodiment, the Ank is within the 3' LTR. The ankyrin element has been shown to increase the expression of the beta-globin gene (Breda, et al. (2012) PloS One, 7(3):e32345).

vi) a Woodchuck Post-Regulatory Element (WPRE). In a particular embodiment, the WPRE is 3' of the 3'LTR. The WPRE increases the titer of the lentivirus, but it can undergo chromosomal rearrangement upon integration. In order to preserve the ability of WPRE to increase viral titers without having this viral element in the integrating sequence, the WPRE is not placed in the integrating portion, but rather is added outside of the LTRs (e.g., after the 3' LTR).

vii) beta globin 3' enhancer. In a particular embodiment, the beta globin enhancer is in antisense orientation.

viii) a Rev response element (RRE). In a particular embodiment, the RRE is from HIV. In a particular embodiment, the RRE is located near the 3'LTR (e.g., between the 5' LTR and the sequence encoding the alpha globin or the beta globin enhancer). The Rev response element (RRE) of HIV facilitates nucleocytoplasmic export of viral mRNAs (Sherpa et al. (2015) Nucleic Acids Res., 43(9):4676-86; incorporated by reference herein).

and ix) a sequence encoding human alpha globin. In a particular embodiment, the human alpha globin is HBA1 (e.g., Gene ID: 3039; GenBank Accession No. NM_000558.5 or NP_000549.1) or HBA2 (e.g., Gene ID: 3040; GenBank Accession No. NM_000517.6 or NP_000508.1). In a particular embodiment, the human alpha globin sequence comprises exons (e.g., exons 1, 2, and 3), introns (e.g., introns 1 and 2), 5' UTR, and/or 3' UTR of the alpha globin gene. In a particular embodiment, the sequence encoding human alpha globin is codon optimized. FIG. 9 provides an example of a codon optimized nucleotide sequence of alpha globin. In a particular embodiment, the human alpha globin sequence is in antisense orientation.

In a particular embodiment, the vector comprises at least 4, at least 5, at least 6, at least 7, at least 8, or all 9 elements set forth above. In a particular embodiment, the above elements are organized in the nucleic acid molecule as depicted in FIGS. 1-4, particularly FIG. 1B, 2B, 3B, or 4B. Example of nucleotide sequences of the above elements are presented in FIGS. 8 and 9.

U.S. Patent Application Publication 2018/0008725, incorporated by reference herein, provides viral vectors for the inhibition or treatment of hemoglobinopathies. ALS-10 is depicted schematically in FIG. 11 of U.S. Patent Application Publication 2018/0008725 and FIG. 14 of U.S. Patent Application Publication 2018/0008725 provides SEQ ID NO: 3 which is the nucleic acid sequence of the ALS-10 vector (incorporated by reference herein). ALS-10 provides examples of nucleic acid sequences of certain of the above elements. Notably, the ankyrin element in the 3'LTR of the ALS10 vector of U.S. Patent Application Publication 2018/0008725 was cloned from a bacterial plasmid and contains additional plasmid DNA. In a particular embodiment, the bacterial plasmid DNA is removed from the ankyrin element reducing the size of the 3' LTR from 528 basepairs to 411 basepairs. Additionally, the HS4 in ALS10 was truncated. In a particular embodiment, the vector of the instant invention comprises a complete HS4.

In a particular embodiment, the vector comprises a nucleic acid molecule comprising: i) a 5' long terminal repeat (LTR) and a 3' LTR (e.g., wherein the 3' LTR is self-inactivating); ii) at least one promoter (e.g., the 200 bp beta globin promoter); iii) a beta globin gene locus control region (LCR) comprising HS2-HS4 or HS1-HS4; iv) an ankyrin insulator element (Ank) (e.g., within the 3' LTR); v) beta globin 3' enhancer; vi) a Rev response element (RRE) (e.g., from HIV; e.g., between the 5' LTR and the sequence encoding the alpha globin); and/or vii) a sequence encoding human alpha globin (e.g., comprising exons, introns, 5' UTR, and/or 3' UTR). In a particular embodiment, the enhancer, LCR, promoter, and sequence encoding human alpha globin are in antisense orientation or reverse complement. In a particular embodiment, the nucleic acid molecule further comprises a Woodchuck Post-Regulatory Element (WPRE) (e.g., wherein the WPRE is not between the two LTRs (e.g., 3' of the 3' LTR).

In a particular embodiment, the vector comprises a nucleic acid molecule comprising: i) a 5' long terminal repeat (LTR) and a 3' LTR (e.g., wherein the 3' LTR is self-inactivating); ii) at least one promoter (e.g., the 200 bp beta globin promoter); iii) a beta globin gene locus control region (LCR) comprising HS2-HS4; iv) an ankyrin insulator element (Ank) (e.g., within the 3' LTR); v) beta globin 3' enhancer (optionally); vi) a Rev response element (RRE) (e.g., from HIV; e.g., between the 5' LTR and the sequence encoding the alpha globin); and/or vii) the HBA1 or HBA2 alpha globin gene comprising exons 1, 2, and 3, introns 1 and 2, 5' UTR, and 3' UTR. In a particular embodiment, the enhancer, LCR, promoter, and HBA1 or HBA2 alpha globin gene are in antisense orientation or reverse complement. In a particular embodiment, the nucleic acid molecule further comprises a Woodchuck Post-Regulatory Element (WPRE) (e.g., wherein the WPRE is not between the two LTRs (e.g., 3' of the 3' LTR). In a particular embodiment, the HBA1 or HBA2 alpha globin gene is codon optimized.

In a particular embodiment, the vector comprises a nucleic acid molecule comprising: i) a 5' long terminal repeat (LTR) and a 3' LTR (e.g., wherein the 3' LTR is self-inactivating); ii) at least one promoter (e.g., the 200 bp beta globin promoter); iii) a beta globin gene locus control region (LCR) comprising HS1-HS4; iv) an ankyrin insulator element (Ank) (e.g., within the 3' LTR); v) beta globin 3' enhancer; vi) a Rev response element (RRE) (e.g., from HIV; e.g., between the 5' LTR and the sequence encoding the alpha globin); and/or vii) the HBA1 or HBA2 alpha globin gene comprising exons 1, 2, and 3, introns 1 and 2, 5' UTR, and 3' UTR. In a particular embodiment, the enhancer, HS2-HS4 of the LCR (but not HS1), promoter, and HBA1 or HBA2 alpha globin gene are in antisense orientation or reverse complement. In a particular embodiment, the nucleic acid molecule further comprises a Woodchuck Post-Regulatory Element (WPRE) (e.g., wherein the WPRE is not between the two LTRs (e.g., 3' of the 3' LTR). In a particular embodiment, the HBA1 or HBA2 alpha globin gene is codon optimized.

In a particular embodiment, the vector comprises a nucleic acid molecule comprising: i) a 5' long terminal repeat (LTR) and a 3' LTR (e.g., wherein the 3' LTR is self-inactivating); ii) at least one promoter (e.g., the 200 bp beta globin promoter); iii) a beta globin gene locus control region (LCR) comprising HS1-HS4; iv) an ankyrin insulator element (Ank) (e.g., within the 3' LTR); v) beta globin 3' enhancer; vi) a Rev response element (RRE) (e.g., from HIV; e.g., between the 5' LTR and the sequence encoding the alpha globin); and/or vii) the HBA1 or HBA2 alpha globin gene comprising exons 1, 2, and 3, introns 1 and 2, 5' UTR, and 3' UTR. In a particular embodiment, the enhancer, the LCR, promoter, and HBA1 or HBA2 alpha globin gene are in antisense orientation or reverse complement. In a particular embodiment, the nucleic acid molecule further comprises a Woodchuck Post-Regulatory Element (WPRE) (e.g., wherein the WPRE is not between the two LTRs (e.g., 3' of the 3' LTR). In a particular embodiment, the HBA1 or HBA2 alpha globin gene is codon optimized.

In certain embodiment, the viral vector of the instant invention has a nucleotide sequence identical to those presented herein or they can have at least 80, 81, 82, 83, 84, 85, 86, 87, 88, 89, 90, 91, 92, 93, 94, 95, 96, 97, 98, or 99% identity to the nucleotide sequence of a viral vector disclosed herein or to an element (or the reverse complement thereof) of a nucleotide sequence of a viral vector disclosed herein. In certain embodiment, the viral vector has a nucleotide sequence identical to those presented herein or they can have at least 80, 81, 82, 83, 84, 85, 86, 87, 88, 89, 90, 91, 92, 93, 94, 95, 96, 97, 98, or 99% identity to ALS20α or ALS20α codon optimized, as shown in FIGS. 8 and 9, respectively. In certain embodiments, the lentiviral vector of the instant invention is selected from the group consisting of Alpha 1/AA305, ALS19α, and ALS20α. In certain embodiments, the lentiviral vector of the instant invention is ALS19α or ALS20α. In certain embodiment, the viral vector has a nucleotide sequence having at least 80, 81, 82, 83, 84, 85, 86, 87, 88, 89, 90, 91, 92, 93, 94, 95, 96, 97, 98, 99, or 100% identity to SEQ ID NO: 1 or SEQ ID NO: 2.

In certain embodiments, the 5' LTR comprises a nucleotide sequence having at least 80, 81, 82, 83, 84, 85, 86, 87, 88, 89, 90, 91, 92, 93, 94, 95, 96, 97, 98, 99, or 100% identity to nucleotides 1899-2079 of FIG. 8 or 9 or SEQ ID NO: 1 or 2. In certain embodiments, the 5' LTR comprises or consists of nucleotides 1899-2079 of FIG. 8 or 9 or SEQ ID NO: 1 or 2.

In certain embodiments, the polyadenylation signal comprises a nucleotide sequence having at least 80, 81, 82, 83, 84, 85, 86, 87, 88, 89, 90, 91, 92, 93, 94, 95, 96, 97, 98, 99, or 100% identity to nucleotides 10017-10244 of FIG. 8 or 9 or SEQ ID NO: 1 or 2. In certain embodiments, the polyadenylation signal comprises or consists of nucleotides 10017-10244 of FIG. 8 or 9 or SEQ ID NO: 1 or 2.

In certain embodiments, the promoter comprises a nucleotide sequence having at least 80, 81, 82, 83, 84, 85, 86, 87, 88, 89, 90, 91, 92, 93, 94, 95, 96, 97, 98, 99, or 100% identity to nucleotides 5617-5418 of FIG. 8 or 9 or the reverse complement of nucleotides 5418-5617 of SEQ ID NO: 1 or 2. In certain embodiments, the promoter comprises or consists of nucleotides 5617-5418 of FIG. 8 or 9 or the reverse complement of nucleotides 5418-5617 of SEQ ID NO: 1 or 2.

In certain embodiments, exon 1 of human alpha globin gene comprises a nucleotide sequence having at least 80, 81, 82, 83, 84, 85, 86, 87, 88, 89, 90, 91, 92, 93, 94, 95, 96, 97, 98, 99, or 100% identity to nucleotides 5312-5218 of FIG. 8 or 9 or the reverse complement of nucleotides 5218-5312 of SEQ ID NO: 1 or 2. In certain embodiments, exon 1 of human alpha globin gene comprises or consists of nucleotides 5312-5218 of FIG. 8 or 9 (particularly FIG. 9) or the reverse complement of nucleotides 5218-5312 of SEQ ID NO: 1 or 2, particularly SEQ ID NO: 2.

In certain embodiments, intron 1 of human alpha globin gene comprises a nucleotide sequence having at least 80, 81, 82, 83, 84, 85, 86, 87, 88, 89, 90, 91, 92, 93, 94, 95, 96, 97, 98, 99, or 100% identity to nucleotides 5217-5101 of FIG. 8 or 9 or the reverse complement of nucleotides 5101-5217 of SEQ ID NO: 1 or 2. In certain embodiments, intron 1 of human alpha globin gene comprises or consists of nucleotides 5217-5101 of FIG. 8 or 9 or the reverse complement of nucleotides 5101-5217 of SEQ ID NO: 1 or 2.

In certain embodiments, exon 2 of human alpha globin gene comprises a nucleotide sequence having at least 80, 81, 82, 83, 84, 85, 86, 87, 88, 89, 90, 91, 92, 93, 94, 95, 96, 97, 98, 99, or 100% identity to nucleotides 5100-4896 of FIG. 8 or 9 or the reverse complement of nucleotides 4896-5100 of SEQ ID NO: 1 or 2. In certain embodiments, exon 2 of human alpha globin gene comprises or consists of nucleotides 5100-4896 of FIG. 8 or 9 (particularly FIG. 9) or the reverse complement of nucleotides 4896-5100 of SEQ ID NO: 1 or 2, particularly SEQ ID NO: 2.

In certain embodiments, intron 2 of human alpha globin gene comprises a nucleotide sequence having at least 80, 81, 82, 83, 84, 85, 86, 87, 88, 89, 90, 91, 92, 93, 94, 95, 96, 97, 98, 99, or 100% identity to nucleotides 4895-4754 of FIG. 8 or 9 or the reverse complement of nucleotides 4754-4895 of SEQ ID NO: 1 or 2. In certain embodiments, intron 2 of human alpha globin gene comprises or consists of nucleotides 4895-4754 of FIG. 8 or 9 or the reverse complement of nucleotides 4754-4895 of SEQ ID NO: 1 or 2.

In certain embodiments, exon 3 of human alpha globin gene comprises a nucleotide sequence having at least 80, 81, 82, 83, 84, 85, 86, 87, 88, 89, 90, 91, 92, 93, 94, 95, 96, 97, 98, 99, or 100% identity to nucleotides 4753-4625 of FIG. 8 or 9 or the reverse complement of nucleotides 4625-4753 of SEQ ID NO: 1 or 2. In certain embodiments, exon 3 of human alpha globin gene comprises or consists of nucleotides 4753-4625 of FIG. 8 or 9 (particularly FIG. 9) or the reverse complement of nucleotides 4625-4753 of SEQ ID NO: 1 or 2, particularly SEQ ID NO: 2.

In certain embodiments, the beta globin 3' enhancer comprises a nucleotide sequence having at least 80, 81, 82, 83, 84, 85, 86, 87, 88, 89, 90, 91, 92, 93, 94, 95, 96, 97, 98, 99, or 100% identity to nucleotides 4508-3633 of FIG. 8 or 9 or the reverse complement of nucleotides 3633-4508 of SEQ ID NO: 1 or 2. In certain embodiments, beta globin 3' enhancer comprises or consists of nucleotides 4508-3633 of FIG. 8 or 9 or the reverse complement of nucleotides 3633-4508 of SEQ ID NO: 1 or 2.

In certain embodiments, the Woodchuck Post-Regulatory Element (WPRE) comprises a nucleotide sequence having at least 80, 81, 82, 83, 84, 85, 86, 87, 88, 89, 90, 91, 92, 93, 94, 95, 96, 97, 98, 99, or 100% identity to nucleotides 9397-9989 of FIG. 8 or 9 or SEQ ID NO: 1 or 2. In certain embodiments, WPRE comprises or consists of nucleotides 9397-9989 of FIG. 8 or 9 or SEQ ID NO: 1 or 2.

In certain embodiments, the ankyrin insulator element (Ank) comprises a nucleotide sequence having at least 80, 81, 82, 83, 84, 85, 86, 87, 88, 89, 90, 91, 92, 93, 94, 95, 96, 97, 98, 99, or 100% identity to nucleotides 8968-9157 of FIG. 8 or 9 or SEQ ID NO: 1 or 2. In certain embodiments, Ank comprises or consists of nucleotides 8968-9157 of FIG. 8 or 9 or SEQ ID NO: 1 or 2.

In certain embodiments, the LTR comprising an ankyrin insulator element (Ank) comprises a nucleotide sequence having at least 80, 81, 82, 83, 84, 85, 86, 87, 88, 89, 90, 91, 92, 93, 94, 95, 96, 97, 98, 99, or 100% identity to nucleotides 8920-9341 of FIG. 8 or 9 or SEQ ID NO: 1 or 2. In certain embodiments, the LTR comprising an Ank comprises or consists of nucleotides 8920-9341 of FIG. 8 or 9 or SEQ ID NO: 1 or 2.

In certain embodiments, the globin gene locus control region (LCR) comprises a nucleotide sequence having at least 80, 81, 82, 83, 84, 85, 86, 87, 88, 89, 90, 91, 92, 93, 94, 95, 96, 97, 98, 99, or 100% identity to nucleotides 5624-8556 of FIG. 8 or 9 or SEQ ID NO: 1 or 2. In certain embodiments, the LCR comprises or consists of nucleotides 5624-8556 of FIG. 8 or 9 or SEQ ID NO: 1 or 2.

The present disclosure provides compositions and methods for the inhibition, prevention, and/or treatment of alpha-thalassemia. In particular, the present disclosure provides novel vectors, particularly viral vectors, for the inhibition, prevention, and/or treatment of alpha-thalassemia. Viral vectors include, for example, retroviruses and lentiviruses. In a particular embodiment, the viral vector is a lentivral vector.

In accordance with the instant invention, compositions and methods are provided for increasing alpha globin production in a cell or subject. The method comprises administering a viral vector of the instant invention to the cell, particularly a hematopoietic stem cell, an erythroid precursor cell or erythroid cell (e.g., CD34+ cell), or subject. In a particular embodiment, the subject has alpha-thalassemia. In a particular embodiment, the cells are obtained from a subject with alpha-thalassemia who is to be treated with the transduced cells. The viral vector may be administered in a composition further comprising at least one pharmaceutically acceptable carrier.

In accordance with another aspect of the instant invention, compositions and methods for inhibiting (e.g., reducing or slowing), treating, and/or preventing alpha-thalassemia in a subject in need thereof are provided. In a particular embodiment, the subject has Hemoglobin H disease (HbH) or Hb Bart's Hydrops Fetalis Syndrome. In a particular embodiment, the methods comprise administering to a subject in need thereof a viral vector of the instant invention. The viral vector may be administered in a composition further comprising at least one pharmaceutically acceptable carrier. The viral vector may be administered via methods wherein the viral vector is delivered to/transduced into a cell, particularly a hematopoietic stem cell, an erythroid precursor cell or erythroid cell (e.g., CD34+ cell)—particularly autologous cells—and then the cells are administered to the subject. In a particular embodiment, the methods of the instant invention are ex vivo therapies. In a particular embodiment, the method further comprises isolating hematopoietic cells (e.g., hematopoietic stem cells or erythroid precursor cells) or erythroid cells from a subject, delivering a viral vector of the instant invention to the cells (e.g., transducing the cells), and administering the treated cells to the subject (optionally after myleoblation of the subject). In a particular embodiment, the hematopoietic cells are transduced with the viral vector using LentiBOOST™ (SIRION Biotech; Germany) or LentiBlast™ (OZ Biosciences, San Diego, CA). The methods of the instant invention may further comprise monitoring the disease or disorder in the subject after administration of the composition(s) of the instant invention to monitor the efficacy of the method. For example, the subject may be monitored for characteristics of low alpha globin of the alpha globin levels of the subject may be monitored in the blood.

As explained hereinabove, the compositions of the instant invention are useful for increasing hemoglobin production and for treating alpha-thalassemia. A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The compositions of the present invention can be administered by any suitable route, for example, by injection (e.g., for local (direct) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered directly to the blood stream (e.g., intravenously). In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, Pa. Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed. Pharmaceutical preparations for injection are known in the art. If injection is selected as a method for administering the therapy, steps should be taken to ensure that sufficient amounts of the molecules reach their target cells to exert a biological effect.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice, and the minimal and maximal dosages may be determined based on the therapeutic results and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient suffering from a disease or disorder, including improvement in the condition of the patient (e.g., in one or more symptoms), delay in the progression of the condition, etc.

As used herein, the term "prevent" refers to the prophylactic treatment of a subject who is at risk of developing a condition and/or sustaining a disease or disorder, resulting in a decrease in the probability that the subject will develop conditions associated with the thalassemia.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated with a thalassemia.

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. A vector may comprise expression operons or elements such as, without limitation, transcriptional and translational control sequences, such as promoters, enhancers, translational start signals, polyadenylation signals, terminators, and the like, and which facilitate the expression of a polynucleotide or a polypeptide coding sequence in a host cell or organism.

Generally, the term "operably linked" means that the regulatory sequences necessary for expression of a coding sequence are placed in the nucleic acid molecule in the appropriate positions relative to the coding sequence so as to effect expression of the coding sequence. This same definition is sometimes applied to the arrangement of coding sequences and transcription control elements (e.g. locus control regions, promoters, enhancers, termination elements, etc.) in an expression vector.

The following examples are provided to illustrate various embodiments of the present invention. They are not intended to limit the invention in any way.

Example 1

FIG. 1A provides a schematic of the Alpha1/AA305 vector. The vector is based on a pCCL plasmid backbone. Located between the HIV-1 long terminal repeats (LTRs) are hypersensitive sites 2-4 (HS2-HS4) of the beta globin locus control region (LCR) as well as the full alpha globin (HBA1) gene, including the HBA1 5' and 3' UTRs, exons 1-3, and introns 1-2. The alpha globin gene is driven by the 200 bp beta globin promoter. The construct from the 3' HBA UTR to the HS4 element are in the antisense orientation.

FIG. 1B provides a detailed schematic of the region of the Alpha1/AA305 vector between the two viral LTRs. The figure depicts the Ankyrin insulator within the 3' LTR and the hypersensitive sites 2-4 of the beta globin LTR. FIG. 1B also shows the full HBA1 alpha globin gene with complete 5' and 3' UTRs, all 3 exons, and both introns. FIG. 1B also shows the promoter.

FIG. 2A provides a schematic of the ALS19α vector. The vector is based on a pCCL plasmid backbone. Located between the long terminal repeats are HS1-HS4 of the beta globin locus control region (LCR) as well as the full alpha globin (HBA1) gene, including the HBA1 5' and 3' UTRs. This construct also contains the 3' enhancer of the beta globin gene (HBB) following the alpha globin 3' UTR. The alpha globin gene is driven by the 200 bp beta globin promoter. With the exception of HS1, which is in the sense orientation, the construct from the HBB 3' enhancer to the HS4 element are in antisense orientation. Additionally, ALS19α contains a barrier insulator isolated from the human ankyrin gene incorporated into the 3' HIV LTR.

FIG. 2B provides a detailed schematic of the region of the ALS19α vector between the two viral LTRs. The figure depicts the Ankyrin insulator within the 3' LTR and hypersensitive sites 1-4 of the beta globin LTR. HS1 is in the sense orientation, which is opposite to the remainder of the vector between the LTRs, which is in the antisense orientation. FIG. 2B also shows the full HBA1 alpha globin gene with complete 5' and 3' UTRs, all 3 exons, and both introns. FIG. 2B also shows the 3' beta globin enhancer and promoter.

FIG. 3A provides a schematic of the ALS20α vector. The vector is based on a pCCL plasmid backbone. Located between the long terminal repeats are HS1-HS4 of the beta globin locus control region (LCR) as well as the full alpha globin (HBA2) gene, including the HBA2 5' and 3' UTRs. This construct also contains the 3' enhancer of the beta globin gene following the alpha globin 3' UTR. The alpha globin gene is driven by the 200 bp beta globin promoter. The construct from the HBB 3' enhancer to the HS4 element is in antisense orientation. Additionally, ALS19α contains a barrier insulator isolated from the human ankyrin gene incorporated into the 3' LTR.

FIG. 3B provides a detailed schematic of the region of the ALS20α vector between the two viral LTRs. The figure depicts the Ankyrin insulator within the 3' LTR and hypersensitive sites 1-4 of the beta globin LTR. HS1 is in the antisense orientation. FIG. 3B also shows the full HBA2 alpha globin gene with complete 5' and 3' UTRs, all 3 exons, and both introns. FIG. 3B also shows the 3' beta globin enhancer and promoter.

FIG. 4A provides a schematic of the codon optimized ALS20α vector. The vector is based on a pCCL plasmid backbone. Located between the long terminal repeats there are HS1-HS4 of the beta globin locus control region (LCR) as well as the full alpha globin (HBA2) gene, including the HBA2 5' and 3' UTRs. Portions of exons 1-3 of the HBA2 gene have been codon optimized to increase gene expression using an optimization algorithm from GenScript (Piscataway, NJ). This construct also contains the 3' enhancer of the beta globin gene following the alpha globin 3' UTR. The alpha globin gene is driven by the 200 bp beta globin promoter. The construct from the HBB 3' enhancer to the HS4 element is in antisense orientation. Additionally, ALS20α contains a barrier insulator isolated from the human ankyrin gene incorporated into the 3' LTR.

FIG. 4B provides a detailed schematic of the region of the codon optimized ALS20α vector between the two viral LTRs. The figure depicts the Ankyrin insulator within the 3' LTR and hypersensitive sites 1-4 of the beta globin LTR. HS1 is in the antisense orientation. FIG. 4B shows the full HBA2 alpha globin gene with complete 5' and 3' UTRs wherein the exons have been modified to be codon optimized using an algorithm from GenScript. FIG. 4B also shows the 3' beta globin enhancer and promoter.

Mouse erythroleukemia (MEL) cells are an immortalized mouse cell line capable of differentiation into erythroid like cells which successfully produce hemoglobin tetramers. MEL cells can be differentiated by contacting the cells with hexamethylene bisacetamide (HMBA). Using high performance liquid chromatography (HPLC), the relative production of hemoglobin tetramers can be analyzed. Differentiated MEL cells display two major peaks corresponding to the formation of mouse hemoglobin major and mouse hemoglobin minor (Lee et al., Biochim. Biophys. Acta Gene Regul. Mech. (2017) 160:393-404). Thus, MEL cells produce two separate beta globin proteins that form hemoglobin tetramers that can be discriminated using HPLC. Mouse hemoglobin major consists of hemoglobin using beta globin major and mouse alpha globin, while mouse hemoglobin minor consists of hemoglobin using beta globin minor and mouse alpha globin.

MEL cells were transduced with the Alpha 1/AA305 vector and differentiated. The number of vector integrations (vector copy number—VCN) was measured using qPCR and determined to be 2.77 based on comparison to standard samples. HPLC analysis reveals that mouse hemoglobin major (73.56%) and mouse hemoglobin minor peaks (13.49%) are still visible. However, there is an additional peak at 4.550 (12.96%), representing the formation of a chimeric human alpha/mouse beta hemoglobin tetramer. In conjunction with the formation of the chimeric Hb peak there is a decrease in the mouse hemoglobin minor peak.

Western Blot assays were also performed on cell lysates with a human alpha globin specific antibody. Human alpha globin was undetectable in mock transduced MEL cells. However, increasing amounts of human alpha globin was observed with increasing amounts of vector transduced into MEL cells. These results demonstrate the availability of a human alpha globin specific antibody as well as a dose dependent response between the alpha globin expressing vector and human alpha globin protein production.

In additional experiments, MEL cells were also transduced with the Alpha 1/AA305 vector such that a VCN of 5.10 was achieved. HPLC analysis reveals that mouse hemoglobin major (56.56%) and mouse hemoglobin minor (10.44%) are present as well as the chimeric hemoglobin (25.67%). Thus, the normal mouse hemoglobin minor peak is dramatically reduced compared to the data with a VCN of 2.77 and there is a dramatic increase in the formation of the chimeric hemoglobin compared to the data with a VCN of 2.77.

In additional experiments, MEL cells were also transduced with the Alpha 1/AA305 vector such that a VCN of 13.86 was achieved. HPLC analysis reveals that mouse hemoglobin major (53.41%) and mouse hemoglobin minor (3.93%) are present as well as the chimeric hemoglobin (37.73%). This extreme VCN represents allows for observation of the limit of alpha globin expression possible using this vector. The chimeric peak is greatly increased and the mouse hemoglobin minor peak is dramatically decreased relative to un-transduced cells.

MEL cells were also transduced with the ALS19α vector. The VCN for this experiment was found to be 2.81. HPLC analysis reveals that mouse hemoglobin major (76.83%) and mouse hemoglobin minor (19.29%) are present as well as the chimeric hemoglobin (3.89%). In additional experiments, MEL cells were also transduced with the ALS19α vector such that a VCN of 3.65 was achieved. HPLC analysis reveals that mouse hemoglobin major (60.44%) and mouse hemoglobin minor (10.68%) are present as well as the chimeric hemoglobin (23.73%). In additional experiments, MEL cells were also transduced with the ALS19α vector such that a VCN of 6.63 was achieved. HPLC analysis reveals that mouse hemoglobin major (56.59%) and mouse hemoglobin minor (3.94%) are present as well as the chimeric hemoglobin (35.47%). In additional experiments, MEL cells were also transduced with the ALS19α vector such that a VCN of 8.53 was achieved. HPLC analysis reveals that mouse hemoglobin major (54.61%) and mouse hemoglobin minor (4.20%) are present as well as the chimeric hemoglobin (36.56%). Thus, the normal mouse hemoglobin minor peak is reduced as VCN increases and the formation of the chimeric hemoglobin increases as VCN increases.

Reverse phase high performance liquid chromatography was used to resolve the relative amounts of globin subunits in differentiated MEL cells. Mouse alpha globin, mouse minor beta globin, and mouse major beta globin were identified on the chromatogram. The relative percentages of mouse alpha globin, mouse minor beta globin, mouse major beta globin, and human alpha globin were determined as well as the percentage of mouse alpha globin and human alpha globin from the total alpha globin.

For untransduced MEL cells, the relative percentages were determined to be: mouse alpha globin: 46.47%, mouse major beta globin: 40.79%, mouse minor beta globin: 12.74%, and human alpha globin: 0.00%. Obviously, mouse alpha globin was 100% of the total alpha globin.

For MEL cells transduced with the Alpha 1/AA305 vector with a VCN of 5.10, the relative percentages were determined to be: mouse alpha globin: 30.65%, mouse major beta globin: 34.42%, mouse minor beta globin: 13.77%, and human alpha globin: 21.15%. Mouse alpha globin was 59.17% of the total alpha globin and human alpha globin was 40.83% of the total alpha globin.

For MEL cells transduced with the Alpha 1/AA305 vector with a VCN of 13.63, the relative percentages were determined to be: mouse alpha globin: 25.64%, mouse major beta globin: 35.25%, mouse minor beta globin: 14.38%, and human alpha globin: 24.73%. Mouse alpha globin was 50.89% of the total alpha globin and human alpha globin was 49.11% of the total alpha globin.

FIG. 5A provides a scatter plot of the percentage of human alpha globin produced of the total alpha globin per vector copy number (VCN) of the Alpha 1/AA305 vector. The points were then fit to a logarithmic curve. From this curve, it can be calculated that a single vector integration would lead to the production of roughly 29.67% of the total alpha globin. In further experiments, the Alpha 1/AA305 vector and ALS19α were compared. As seen in FIG. 5B, the Alpha 1/AA305 and ALS19α vectors produces, respectively, between 55% and 70% (on average) of the endogenous mouse alpha globin gene per vector copy number (VCN). In other words, 1 copy of each vector produces between 55% and 70% of a single mouse alpha-globin gene, respectively. These results show that the ALS19α vector yields statistically significant more alpha globin than the Alpha 1/AA305 vector. Additionally, FIG. 5C provides a plot of the ratio of human alpha-globin protein over the baseline level of the mouse alpha-globin protein over VCN by the vector ALS19α using MEL cells. As MEL cells harbor four copies of the mouse alpha-globin gene, ideally, 4 copies of ALS19α should make 50% of the total alpha-globin proteins (mouse+human). These results indicate that ALS19α is able to make high levels of human alpha-globin protein in MEL cells. Indeed, on average, 1 copy of ALS19α makes 70% of 1 mouse alpha-globin gene.

Notably, these experiments involve the expression of a human gene in mouse cells. The expression of this human gene in human cells will produce higher levels of human alpha-globin protein.

In view of foregoing, transduction with an alpha globin expressing vector results in an increase of the percentage of chimeric human alpha globin/mouse beta globin hemoglobin tetramers. The transduction with an alpha globin expressing vector also results in the production of human alpha globin and an associated decrease in mouse alpha globin. Further, it is demonstrated that the instant vectors can express high levels of the human alpha globin gene, particularly in therapeutic ranges for the treatment or cure of alpha-thalassemia.

FIG. 6A provides a scatter plot demonstrating the relationship between the vector copy number (VCN) and human alpha globin production. On the X-axis is the VCN calculated via qPCR, while on the y-axis is the total human alpha globin as measured by HPLC. The total human alpha globin percentage was calculated by taking the sum of the area of the mouse beta major:human alpha tetramer and an estimate of the mouse beta minor:human alpha area. Thus, the "Total Human Alpha Globin Area" on the graph corresponds to the percentage of hemoglobin tetramers in the sample that contains the human alpha globin. Furthermore, each vector is provided with an associated linear regression and $R^2$ value. For these samples, the total human alpha globin was calculated based on estimating the area of the mouse beta minor:human alpha tetramer, as this peak was not clearly visible for much of the collection of this data. When this peak was successfully resolved the total human alpha globin area was calculated through direct addition of the two peaks (represented by the New data). As can be seen, the data calculated based on our previous estimations for ALS20α almost completely overlap with the data measured directly (New). As a result of this comparison, it is clear that the previous method of estimation gave an accurate indication of the level of human alpha globin produced.

The data in FIG. 6A clearly indicates that there is a general linear relationship between the VCN and the amount of hemoglobin produced. When compared between vectors, ALS20α clearly demonstrates the highest level of human alpha globin production per vector integration, in addition to offering more stable results compared to ALS19α.

Based on the data in FIG. 6A, the production of human alpha globin from the lentiviral vector was compared to the production of mouse alpha globin from the endogenous mouse genes. The data collected was used to calculate the percentage total hemoglobin produced per VCN. This data was in turn compared to the remaining mouse alpha globin used in hemoglobin tetramers. By definition, the tetramers containing mouse alpha globin represent the production of the four endogenous mouse alpha globin genes. Thus, the percentage of mouse alpha containing areas was divided by four, generating the total amount of mouse alpha globin produced per gene. The amount of mouse alpha globin per gene and the amount of human alpha globin per VCN were compared. FIG. 6B shows the human alpha globin production per VCN as it relates to the endogenous mouse alpha globin per gene. A measure of ~50% (such as the Alpha 1 vector) indicates that, on average, cells transduced with the Alpha1 vector produced ~50% of the alpha globin that an endogenous mouse alpha globin gene produces. As can be seen in FIG. 6B, the ALS20α vector yields statistically significant higher levels of alpha globin than the other vectors. Indeed, the ALS20α vector surprisingly produces almost 100% of the alpha globin that is produced by a single endogenous mouse alpha globin gene. Inasmuch as the codon optimized ALS20α vector was optimized for production in human cells, it was not expected to yield significant production in these assays in mouse cells.

Example 2

Alpha globin knockout human umbilical cord derived erythroid progenitor cells (HUDEPs) were generated. HUDEPs are immortalized human erythroid progenitor cells that differentiate into red blood cell-like cells upon stimulation (Kurita et al. (2013) PLoS ONE 8(3):e59890). To test the efficacy of the alpha globin expressing vectors in human cells, HUDEPs were selected as an appropriate model. However, given that HUDEP cells express normal levels of alpha globin, a separate cell line was created in which the two genes contributing to alpha globin expression (HBA2 and HBA1) had been knocked out.

Briefly, the alpha globin knockout HUDEPs were synthesized as follows. First, normal, healthy HUDEP cells were obtained and placed into culture. Second, the alpha globin genes were then knocked out using CRISPR technology. Specifically, the HUDEP cells were then transfected with Cas9 as well as a specific guide RNA corresponding to the sequence for HBA. HBA1 and HBA2 are highly homologous so only a single guide was required.

This resulted in the creation of a pool of HUDEP cells in which some cells had been successfully transfected and had HBA1/2 knocked out and some cells in which the transfection and/or knockout was unsuccessful. Furthermore, given that there are two copies of each alpha globin gene (for a total of 4 alpha globin genes), the efficacy of the knockout could vary between the successful knockout of between 0 and 4 copies. Accordingly, this pool of HUDEP cells was subjected to a limiting dilution intended to isolate a single cell into a single well. These isolated cells were then propagated for several weeks to increase their numbers. Each well would then theoretically be genetically identical, having been derived from a single ancestral clone. These clones were then taken and stimulated to differentiate. Following differentiation, the cells were collected, lysed, and analyzed via Reverse Phase High Performance Liquid Chromatography (RP-HPLC) to screen for clones that did not express any alpha globin protein—thereby identifying the desired alpha globin knockout HUDEPs.

Following identification of HUDEP clones expressing no alpha globin, the cells were transduced with varying concentrations of alpha globin expressing vector. After several days, the HUDEP clones were stimulated to differentiate. Following differentiation, cells were collected, lysed, and analyzed via RP-HPLC. FIG. 7 provides three separate chromatograms from three separate conditions. The first (top) chromatogram shows the normal profile from the differentiation of normal HUDEP cells. The peaks corresponding to the level of fetal hemoglobin (HbF) and the level of normal adult hemoglobin (HbA) are identified. The second (middle) chromatogram was obtained from the differentiation of non-transduced alpha globin knockout HUDEPs (HUDEP 2 HBA1/2 KO Clone 7). As can be seen, the fetal globin and adult hemoglobin peaks observed in the normal HUDEP cells are not observed in Clone 7. Instead, Clone 7 demonstrates an alternative peak corresponding to HbH, a tetramer of four beta globin chains that is frequently observed in patients suffering from alpha thalassemia. The third (bottom) chromatogram was obtained from the differentiation of the alpha globin knockout HUDEPs (HUDEP 2 HBA1/2 KO Clone 7) transduced with alpha globin expressing lentiviral vector. This sample was measured to have a VCN of 2.7. As can be seen, while the HbH peak is still present, its area is reduced. Additionally, treatment with the alpha globin expressing vector results in the return of significant HbF and HbA peaks, demonstrating that successful production of alpha globin restores, at least in part, the production of normal hemoglobin in a model simulating clinically relevant alpha thalassemia (such as HbH disease).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A viral vector comprising a nucleic acid molecule comprising:
   i) a 5' long terminal repeat (LTR) and a 3' LTR, wherein one of said LTRs is self-inactivating;
   ii) at least one promoter;
   iii) a beta globin gene locus control region (LCR), wherein said LCR comprises HS1, HS2, HS3, and HS4, wherein said HS1 is in sense orientation and said HS2, HS3, and HS4 are in antisense orientation;
   iv) an ankyrin insulator element (Ank);
   v) a beta globin 3' enhancer; and
   vi) a sequence encoding human alpha globin.

2. The viral vector of claim 1, further comprising a Woodchuck Post-Regulatory Element (WPRE).

3. The viral vector of claim 2, wherein said WPRE is not between the 5' LTR and 3' LTR.

4. The viral vector of claim 1, further comprising a Rev response element (RRE).

5. The viral vector of claim 4, wherein said RRE is located between the 5' LTR and the beta globin 3' enhancer.

6. The viral vector of claim 1, wherein said promoter is the beta globin promoter.

7. The viral vector of claim 1, wherein said sequence encoding human alpha globin is the HBA1 or HBA2 gene.

8. The viral vector of claim 7, wherein said sequence encoding human alpha globin comprises exons 1, 2, and 3, introns 1 and 2, 5' UTR, and 3' UTR.

9. The viral vector of claim 7, wherein said sequence encoding human alpha globin is codon optimized.

10. The viral vector of claim 1, wherein the beta globin 3' enhancer, the promoter, the sequence encoding human alpha globin, and the beta globin gene locus control region are in antisense orientation.

11. The viral vector of claim 1, wherein the viral vector is a lentiviral vector.

12. Isolated CD34+ cells comprising the viral vector of claim 1.

13. The isolated CD34+ cells of claim 12, wherein the CD34+ cells have been isolated from an individual who has alpha-thalassemia.

14. A composition comprising the viral vector of claim 1 and a pharmaceutically acceptable carrier.

15. A composition comprising viral particles, wherein the viral particles are synthesized from the viral vector of claim 1.

16. A method for inducing expression of human alpha globin in cells comprising introducing into said cells a viral vector of claim 1.

17. The method of claim 16, wherein said method is in vitro.

18. A method of inhibiting and/or treating alpha-thalassemia in a subject in need thereof, said method comprising introducing the viral vector of claim 1 into cells and delivering the cells to said subject.

19. The method of claim 18, wherein the cells are isolated from the subject to be treated.

20. A viral vector comprising a nucleic acid molecule comprising:
   i) a 5' long terminal repeat (LTR) and a 3' LTR, wherein one of said LTRs is self-inactivating;
   ii) at least one promoter;
   iii) a beta globin gene locus control region (LCR);
   iv) an ankyrin insulator element (Ank);
   v) a beta globin 3' enhancer; and
   vi) a sequence encoding human alpha globin, wherein said viral vector is selected from the group consisting of Alpha 1/AA305, ALS19α, and ALS20α.

21. Isolated CD34+ cells comprising the viral vector of claim 20.

22. The isolated CD34+ cells of claim 21, wherein the CD34+ cells have been isolated from an individual who has alpha-thalassemia.

23. A composition comprising the viral vector of claim 20 and a pharmaceutically acceptable carrier.

24. A composition comprising viral particles, wherein the viral particles are synthesized from the viral vector of claim 20.

25. A method for inducing expression of human alpha globin in cells comprising introducing into said cells a viral vector of claim 20.

26. A method of inhibiting and/or treating alpha-thalassemia in a subject in need thereof, said method comprising introducing the viral vector of claim 20 into cells and delivering the cells to said subject.

27. The method of claim 26, wherein the cells are isolated from the subject to be treated.

28. A viral vector comprising a nucleic acid molecule comprising:
   i) a 5' long terminal repeat (LTR) and a 3' LTR, wherein one of said LTRs is self-inactivating;
   ii) at least one promoter;
   iii) a beta globin gene locus control region (LCR);
   iv) an ankyrin insulator element (Ank);
   v) a beta globin 3' enhancer; and
   vi) a sequence encoding human alpha globin, wherein said nucleic acid molecule has a nucleotide sequence having at least 95% identity with SEQ ID NO: 1 or SEQ ID NO: 2.

29. The viral vector of claim 28, wherein said nucleic acid molecule comprises SEQ ID NO: 1.

30. The viral vector of claim 28, wherein said nucleic acid molecule has a nucleotide sequence having at least 95% identity with SEQ ID NO: 2.

31. The viral vector of claim 30, wherein said nucleic acid molecule comprises SEQ ID NO: 2.

32. The viral vector of claim 28, wherein said nucleic acid molecule has a nucleotide sequence having at least 95% identity with SEQ ID NO: 1.

33. Isolated CD34+ cells comprising the viral vector of claim 28.

34. The isolated CD34+ cells of claim 33, wherein the CD34+ cells have been isolated from an individual who has alpha-thalassemia.

35. A composition comprising the viral vector of claim 28 and a pharmaceutically acceptable carrier.

36. A composition comprising viral particles, wherein the viral particles are synthesized from the viral vector of claim 28.

37. A method for inducing expression of human alpha globin in cells comprising introducing into said cells a viral vector of claim 28.

38. A method of inhibiting and/or treating alpha-thalassemia in a subject in need thereof, said method comprising introducing the viral vector of claim 28 into cells and delivering the cells to said subject.

39. The method of claim 38, wherein the cells are isolated from the subject to be treated.

* * * * *